United States Patent
Abe et al.

(10) Patent No.: US 11,147,796 B2
(45) Date of Patent: Oct. 19, 2021

(54) AGENT FOR PREVENTING OR AMELIORATING HEARING IMPAIRMENT

(71) Applicants: Tohoku University, Miyagi (JP); Kake Educational Institution, Okayama (JP)

(72) Inventors: Takaaki Abe, Miyagi (JP); Yukio Katori, Miyagi (JP); Yohei Honkura, Miyagi (JP); Fumika Nanto, Miyagi (JP); Kenichiro Hayashi, Okayama (JP)

(73) Assignees: TOHOKU UNIVERSITY, Miyagi (JP); KAKE EDUCATIONAL INSTITUTION, Okayama (JP)

( * ) Notice: Subject to any disclaimer, the term of this patent is extended or adjusted under 35 U.S.C. 154(b) by 0 days.

(21) Appl. No.: 16/229,595

(22) Filed: Dec. 21, 2018

(65) Prior Publication Data
US 2019/0224165 A1    Jul. 25, 2019

(30) Foreign Application Priority Data
Dec. 27, 2017    (JP) .............................. JP2017-252016

(51) Int. Cl.
A61K 31/405    (2006.01)
A61P 27/16    (2006.01)

(52) U.S. Cl.
CPC ............ A61K 31/405 (2013.01); A61P 27/16 (2018.01)

(58) Field of Classification Search
USPC ........................................................ 546/236
See application file for complete search history.

(56) References Cited

FOREIGN PATENT DOCUMENTS

| JP | 2004-99537 | 4/2004 |
| JP | 2011-37738 | 2/2011 |
| JP | 2012-148995 | 9/2012 |
| JP | 2015-189670 A | 11/2015 |
| WO | 2014/080640 | 1/2017 |

OTHER PUBLICATIONS

Suzuki et al. (Mitochonic Acid 5 (MA-5), a Derivative of the Plant Hormone Indole-3-Acetic Acid, Improves Survival of Fibroblasts from Patients with Mitochondrial Diseases. Tohoku J. Exp. Med., 2015, 236, 225-232).*

Gonzalez-Gonzalez (The role of mitochondrial oxidative stress in hearing loss. Neurological Disorders and Therapeutics. vol. 1(4): 1-5. 2017).*

Website of "2017 UMDF Mitochondrial Medicine: Washington DC" http://umdf.org/symposium.

Abstracts of Academic Conference Mitochondrial Medicine 2017 (Cover, Guide map page, Presentation title and Abstract of "#2017 PA-0320").

Poster presentation at "2017 UMDF Mitochondrial Medicine: Washington DC".

* cited by examiner

Primary Examiner — Layla Soroush
(74) Attorney, Agent, or Firm — Edwin S. Flores; Daniel J. Chalker; Chalker Flores, LLP

(57) ABSTRACT

It is to provide an agent for preventing or improving hearing loss, which comprises a low molecular compound which can be produced relatively easily and inexpensively as an active ingredient. One or more compounds selected from the group consisting of compounds represented by the following formulas $(I_0)$, (II), and (III) and a pharmaceutically acceptable salt of the compounds when $R^3$ is OH are used as an agent for preventing or improving hearing loss.

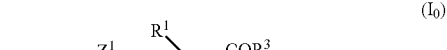

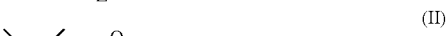

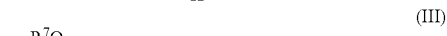

1 Claim, 10 Drawing Sheets
Specification includes a Sequence Listing.

AGENT FOR PREVENTING OR AMELIORATING HEARING IMPAIRMENT

TECHNICAL FIELD

The present invention relates to an agent for preventing or improving hearing loss.

BACKGROUND ART

Sound passes through the ear canal, and vibrates the tympanic membrane and the sound is transmitted as a physical vibration until the vibration reaches the inner ear via the ossicular bone. After that, for the hair cells of the inner ear, the vibration of the sound is replaced by the excitation of the nerve, and then it is transmitted as an impulse of the nerve via the auditory nerve, the brain stem, the mid brain, and is perceived as a sound in the cerebral cortex. Hearing loss is a state in which the sensed level of the sound generated in the cerebral cortex is lowered comparing with the normal state.

Hearing loss is a disease affecting 65 years old and over in 1 person in 3 people, and its overcoming is an important issue related to the quality of life of the people in the aging society. Hearing loss includes various factors such as noise, side effects of drug administration, heredity, and lifestyle habits in addition to aging.

As a component having a prophylactic or therapeutic effect on deafness, a calibrinogenase (Patent Document 1) that is a circulatory disorder ameliorating agent, a substance that increases the expression of endothelin receptor B (Patent Document 2), a methyl group donor and a histone deacetyl compounding agent with an enzyme inhibitor (Patent Document 3) have been reported.

On the other hand, the inventors of the present invention have reported that the compound group of the present invention, which will be described later, has an effect of enhancing expression of erythropoietin and a therapeutic effect of mitochondrial disease (Patent Document 4) and an effect of suppressing organ fibrosis (Patent Document 5). However, it has not been known so far that the compound group of the present invention has the effect of preventing or improving hearing loss.

PRIOR ART DOCUMENTS

Patent Documents

Patent Document 1: Japanese unexamined Patent Application Publication No. 2004-99537
Patent Document 2: Japanese unexamined Patent Application Publication No. 2011-37738
Patent Document 3: Japanese unexamined Patent Application Publication No. 2012-148995
Patent Document 4: WO 2014/080640
Patent Document 5: Japanese unexamined Patent Application Publication No. 2015-189670

SUMMARY OF THE INVENTION

Object to be Solved by the Invention

An object of the present invention is to provide an agent for preventing or improving hearing loss which comprises a low molecular weight compound which can be produced relatively easily and at low cost as an active ingredient.

Means to Solve the Object

The present inventors are continuing diligent studies to solve the object. In the process, the present inventors found that the compound group described below has an effect of effectively preventing or improving the symptoms of hearing loss, and have completed the present invention.

Specifically, the present invention is as follows:

[1] An agent for preventing or improving hearing loss comprising one or more compounds selected from the group consisting of compounds represented by the following formula ($I_0$):

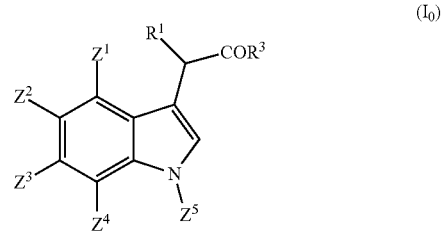

[wherein $R^1$ represents a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group- or cyclopentyl group-substituted methylene or ethylene; wherein the phenyl group is optionally further substituted by one or more phenyl groups, $Z^1$, $Z^2$, $Z^3$ and $Z^4$ are the same or different and each represents a hydrogen atom, a halogen atom, a C1 to C6 alkyl group, a C2 to C6 alkenyl group, a C2 to C6 alkynyl group, an organic oxy group represented by $OR^8$, $R^8$ represents a C1 to C7 alkyl group, a C2 to C6 alkenyl group or a C2 to C6 alkynyl group, $Z^5$ represents a hydrogen atom or a C1 to C6 alkyl group, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms], compounds represented by the following formula (II):

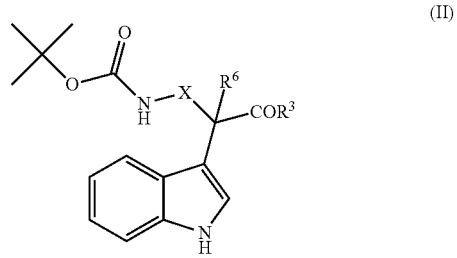

[wherein $R^6$ represents hydrogen or a methyl group, X represents an alkylene group having 4 to 6 carbon atoms or an ether group having 4 carbon atoms, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms], and compounds represented by the following formula (III):

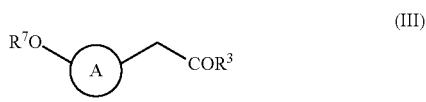

[wherein A represents indole or naphthalene, and when A is indole, positions 3 and 5 of the indole are substituted by an acetic acid group and $R^7O$, respectively, and when A is naphthalene, positions 1 and 7 of the naphthalene are substituted by an acetic acid group and $R^7O$, respectively, $R^7$ represents an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms], and pharmaceutically acceptable salts of the compounds when $R^3$ is OH (hereinafter, these compounds and salts are also collectively referred to as "compound group of the present invention").
[2] The agent according to [1], wherein the hearing loss is a hearing loss caused by one or more factors selected from decreased function of the inner ear; decreased function of the nerve on the central side from the inner ear; drug administration; noise; aging; and oxidative stress.
[3] The agent according to [1] or [2], wherein the compound is a compound represented by the following formula (I-2) or a pharmaceutically acceptable salt thereof:
Formula (I-2):

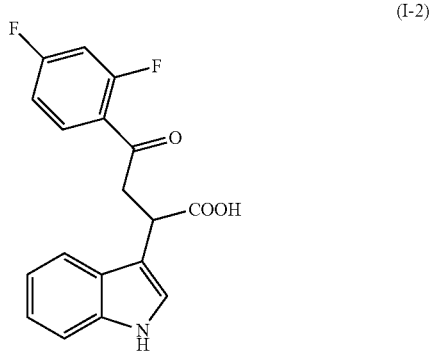 [SMILES: O=C(CC(C(=O)O)c1c[nH]c2ccccc12)c1ccc(F)cc1F]

An alternative embodiment of the present invention can include, for example, a method for preventing or improving (treating) hearing loss, comprising the step of administering, to a subject in need of prevention or improvement (treatment) of hearing loss one or more compounds selected from the compound group of the present invention; one or more compounds selected from the compound group of the present invention for use as an agent for preventing or improving (treating) the hearing loss; one or more compounds selected from the compound group of the present invention for use in preventing or improving (treating) hearing loss, and use of one or more compounds selected from the compound group of the present invention for producing an agent for preventing or improving (treating) hearing loss.

Effect of the Invention

The compound group of the present invention has an effect of improving the symptoms of hearing loss, specifically, those that effectively improve the hearing (hearing ability) level. Also, as specifically shown in Examples described later, the compound group of the present invention is particularly useful for hearing loss caused by one or more factor selected from inner ear hearing loss, drug-induced hearing loss, hereditary diseases, noise-induced hearing loss, age-related hearing loss, and oxidative stress. Moreover, the compound group of the present invention is superior at the point that a low molecular weight compound which can be produced relatively easily and in high yield and useful as an active ingredient for prevention or improvement of hearing loss, can be produced relatively easily and inexpensively.

BRIEF DESCRIPTION OF DRAWINGS

FIG. 8A shows the ABR threshold at 28 days of age just before Compound #5 administration.

FIG. 8B shows the ABR threshold at 60 days of age following Compound #5 administration.

FIG. 8C shows the difference (ABR threshold variation) between the ABR threshold value at the 60 day old age and the ABR threshold value at the 28 day old age. "*" in the figure indicates that there is a statistically significant difference ($p<0.05$).

FIG. 9A shows the ABR threshold at 28 days of age just before Compound #5 administration.

FIG. 9B shows the ABR threshold at 64 days of age following Compound #5 administration.

FIG. 9C shows the difference (ABR threshold variation) between the ABR threshold value at the 64 day old age and the ABR threshold value at the 28 day old age. "*" in the figure indicates that there is a statistically significant difference ($p<0.05$).

FIG. 10A shows the ABR threshold before strong acoustic exposure.

FIG. 10B shows the ABR threshold after 4 hours of strong acoustic exposure.

FIG. 10C shows the difference (ABR threshold variation) between the ABR threshold value 4 hours after the above-mentioned strong acoustic exposure and the ABR threshold value before the strong acoustic exposure. "*" and "**" in the figure indicate statistically significant differences ($p<0.05$ and $p<0.01$), respectively.

MODE OF CARRYING OUT THE INVENTION

Figures 1A, 1B:
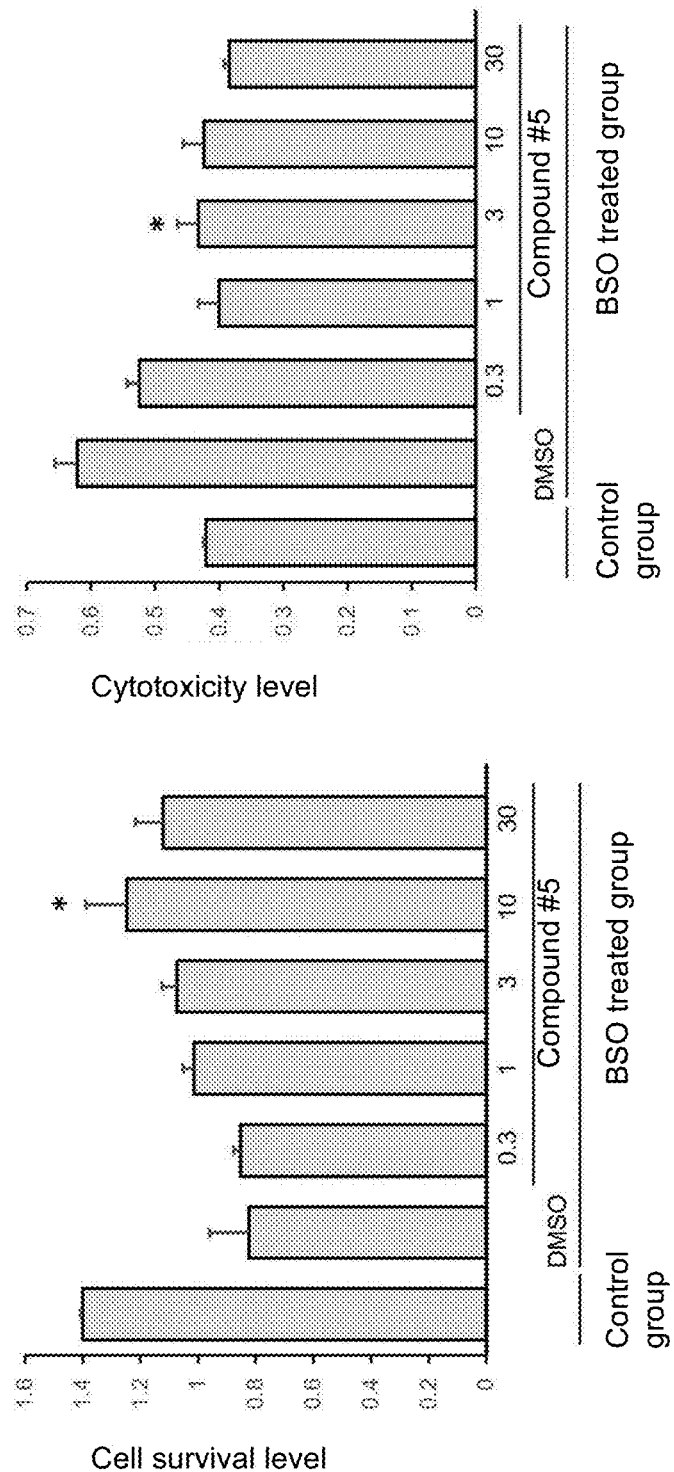
FIGS. 1A and 1B are diagrams showing the results of "m.1555A>G mutant" cells in various BSO-treated groups and control groups analyzing the cell survival level (FIG. 1A) and the cytotoxicity level (FIG. 1B). "*" in the figure represents that there is a statistically significant difference ($p<0.05$) vs. BSO-treated group in the absence of compound #5 ("DMSO" in the figure).

The agent for preventing or improving hearing loss of the present invention is an agent containing one or more compounds selected from the compound group of the present invention as an active ingredient for limited use that is "for preventing or improving hearing loss" (hereinafter, it is sometimes referred to as "preventive/improving agent of the present invention"), where prevention of hearing loss includes prevention of the development of hearing loss and prevention of deterioration of hearing loss symptoms. The compound group of the present invention which is an active ingredient in the preventive/improving agent of the present invention may be used alone as a food or drink or a medicine (preparation), or may be mixed with an additive to form a composition (food and beverage composition or pharmaceutical composition). Examples of such foods and beverages can include health foods (functional foods, nutritional supplements, health supplements, nutritionally enhanced foods, nutritionally adjusted foods, supplements, etc.), and health function foods (foods for specified health use, nutritional functional foods, functional display food etc.).

In this specification, "hearing loss" refers to a state in which the minimum audible value (auditory threshold), which is the perceivable minimum sound pressure level, is lowered compared to the normal auditory threshold (usually about 25 [dB HL] or less). The hearing threshold in hearing loss is usually 26 (dB HL), preferably 41 (dB HL), more preferably 61 (dB HL), still more preferably 81 (dB HL). "Prevention or amelioration of hearing loss" means, in other words, suppression of lowering of the hearing threshold or improvement (rise) of the decreased hearing threshold. Factors of hearing loss are not limited to one, and a plurality (two or more) may be present.

In this specification, hearing loss is roughly divided into sound-induced hearing loss and sensorineural hearing loss according to the region of the ear where functional impairment occurs. Here, the sound-induced hearing loss refers to a hearing loss caused by a decrease in the function of the outer ear and/or the middle ear (for example, the external auditory canal, the tympanic membrane, the ossicular bone [tsubi bone, quince bone, abdominal bone]), Specific examples of the sound-induced hearing loss can include hearing loss caused by otitis media, otosclerosis, tympanic membrane damage, ear canal obstruction, external auditory meititis, and ear canal damage. In addition, the above-described sound-sensitive hearing loss is a hearing disorder (inner ear hearing loss) caused by a decrease in the function of the inner ear (for example, the cochlea) and/or a hearing loss caused by deterioration of the nerve on the central side from the inner ear. Specific examples of the sensorineural hearing loss can include hearing loss caused by Meniere's disease, perilymph fistula, decline in function of the cochlea and the like; sudden hearing loss; drug-induced hearing loss; noise-induced hearing loss; and senile hearing loss. In addition, hearing loss is broadly divided into symptomatic hearing loss (congenital diseases found in other symptoms besides hearing loss, such as eyes, skin, etc.) and non-symptomatic hearing loss (hearing loss without symptoms other than hearing loss), or is broadly divided into congenital hearing loss and acquired hearing loss.

As the above-mentioned hearing loss, since the effect is specifically shown in this embodiment, inner ear hearing loss is preferable, and in particular, hearing loss caused by a decline in the function of the cochlea (cochlear hearing loss) is preferable. Such cochlear hearing loss results as a result of cells in the cochlea such as helical ganglion cells, hair cells (inner hair cells or outer hair cells) being damaged by some factor.

The congenital hearing loss may be any hearing loss caused by congenital factors such as genetic diseases associated with auditory strains, viral infection during pregnancy, Alport syndrome, etc. The congenital hearing loss can include congenital hearing loss caused by for example, abnormality of chromosomal genes such as GJB2 gene (a gene encoding connexin 26), POU4F3 gene, SLC26A4 gene, and NDUFS4 gene, and mitochondrial gene abnormality. Here, abnormality of a gene means that one or more nucleotides are added, substituted, deleted, and/or inserted in a normal gene, and as a result, the original function and the expression level of the protein encoded by the gene are abnormality (markedly decreases or improves).

Examples of the congenital hearing loss caused by abnormality of the mitochondrial gene can include congenital hearing loss caused by a mutation in which adenine (A) at position 1555 of the mitochondrial genomic DNA (NCBI Reference Sequence: NC-012920; polynucleotide consisting of the nucleotide sequence of SEQ ID NO: 1) is substituted with guanine (G) (m.1555A>G mutation); a mutation in which A at position 3243 of the mitochondrial genomic DNA is substituted with G (m.3243A>G mutation); and a mutation in which A at position 7445 of the mitochondrial genomic DNA is substituted with G (m.7445A>G mutation).

The acquired hearing impairment may be any hearing loss caused by acquired factors such as idiopathic disease, fatigue, viral infection, drug administration, oxidative stress, head trauma, noise, and age. Since the effect is specifically shown in the present Example, hearing loss due to drug administration (drug-induced hearing loss), hearing loss due to noise (noisy hearing loss), hearing loss due to aging (age-related hearing loss) hearing loss due to oxidative stress (oxidative stress hypothesis) is preferred. Such drug-induced hearing loss refers to hearing loss caused by side effects caused by drug administration. Examples of drugs to be administered can include aminoglycoside antibacterial substances (streptomycin sulfate, kanamycin, gentamicin, havecacin and the like), platinum preparations (cisplatin etc.) salicylic acid agents (aspirin etc.), and loop diuretics (furosemide, trasemide, bumetanide, azosemide etc.). Especially, drug-induced hearing loss caused by the aminoglycoside antimicrobial substance or cisplatin is largely irreversible, and the quality of life of patients suffering from such hearing loss is greatly reduced. Therefore, as a hearing loss to be prevented or improved, the aminoglycoside drug antibacterial substance or cisplatin-induced drug-induced hearing loss is more preferable.

A detailed description of the compounds contained in compound group of the present inventions is given below.

In one aspect of the present invention, $R^1$ in the formula ($I_0$) is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine. Such a "benzene ring having an alkyl group having 1 to 7 carbon atoms, an alkoxyl group having 1 to 7 carbon atoms, or a benzoylmethyl group substituted with fluorine and/or chlorine" means one or more hydrogen atoms that bind to a carbon atom constituting the benzene ring of the benzoylmethyl group are replaced by an alkyl group having 1 to 7 carbon atoms, an alkoxyl group having 1 to 7 carbon atoms, a fluorine atom and/or a chlorine atom. Accordingly, the substituted benzene ring means that 1 to 5 hydrogen atoms of the hydrogen atoms bonded to the carbon atoms constituting the benzene ring are substituted with an alkyl group having 1 to 7 carbon atoms, an alkoxyl group having 1 to 7 carbon atoms, a benzene ring substituted by fluorine and/or chlorine. When the substituted benzene ring has two or more substituents, the substituents is the same or different.

Examples thereof can include a benzene ring substituted with an alkyl group having 1 to 7 carbon atoms with 1 to 5 carbon atoms, a benzene ring substituted with 1 to 7 alkoxyl groups having 1 to 5 carbon atoms, a benzene ring substituted with 1 to 5 fluorine atoms or a benzoylmethyl group having a benzene ring substituted with 1 to 5 chlorine atoms. Further, as other examples, a benzoylmethyl group having a benzene ring substituted with a total of 2 to 5 substituents selected from an alkyl group having 1 to 4 carbon atoms, an alkoxyl group having 1 to 4 carbon atoms, a fluorine atom and a chlorine atom can be mentioned. In this context, examples of the alkyl group having 1 to 7 carbon atoms can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group, and a 1-propylbutyl group.

Examples of the alkoxyl group having 1 to 7 carbon atoms can include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group.

In an alternative aspect of the present invention, $R^1$ in the formula ($I_0$) is an unsubstituted or fluorine-substituted linear or branched alkyl group having 4 to 6 carbon atoms. Examples of the unsubstituted or fluorine-substituted linear or branched alkyl group having 4 to 6 carbon atoms can include a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2- dimethylpropyl group, a 2,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, and fluorinated forms thereof. The unsubstituted or fluorine-substituted linear or branched alkyl group having 4 to 6 carbon atoms is preferably a 1-ethylbutyl group, a 2-ethylbutyl group, a 1-methylpentyl group, a 2-methylpentyl group, a 3-methylpentyl group, a 4-methylpentyl group, a 5-methylpentyl group, a 3,3,4,4,4-pentafluorobutyl group, a 4,4,5,5,5-pentafluoropentyl group, or a 5,5,6,6,6-pentafluorohexyl group, more preferably a 2-ethylbutyl group, a 2-methylpentyl group, a 3-methylpentyl group, or a 4,4,5,5,5-pentafluoropentyl group, most preferably a 4,4,5,5,5-pentafluoropentyl group.

In an alternative aspect of the present invention, $R^1$ in the formula ($I_0$) is phenyl group- or cyclopentyl group-substituted methylene or ethylene. The phenyl group is optionally further substituted by one or more phenyl groups. The phenyl group- or cyclopentyl group-substituted methylene or ethylene is a benzyl group, a 2-phenethyl group, a cyclopentylmethyl group, or a 2-cyclopentylethyl group. Examples of the benzyl group or the 2-phenethyl group substituted by one or more phenyl groups can include a 3-phenylbenzyl group, a 4-phenylbenzyl group, a 3,5-diphenylbenzyl group, a 2-(1,1'-biphenyl-3-yl)-ethyl group, a 2-(1,1'-biphenyl-4-yl)-ethyl group, and a 2-(3,5-diphenylphenyl)-ethyl group. Preferred examples of $R^1$ in the formula (I) can include a 2-phenethyl group, a cyclopentylmethyl group, a 2-cyclopentylethyl group, and a 2-(1,1'-biphenyl-3-yl)-ethyl group.

$Z^1$, $Z^2$, $Z^3$ and $Z^4$ in the formula ($I_0$) is the same or different and each represents a hydrogen atom, a halogen atom, a C1 to C6 alkyl group, a C2 to C6 alkenyl group, a C2 to C6 alkynyl group, an organic oxy group represented by $OR^8$. $R^8$ represents a C1 to C7 alkyl group, a C2 to C6 alkenyl group or a C2 to C6 alkynyl group. $Z^5$ can include a hydrogen atom or a C1 to C6 alkyl group. Examples of the halogen atom can include a fluorine atom, a chlorine atom, a bromine atom, and an iodine atom. Examples of a C1 to C6 alkyl group can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, and a 1-ethyl-2-methylpropyl group. Examples of a C2 to C6 alkenyl group can include an ethenyl group (vinyl group), a 1-propenyl group, a 2-propenyl group (allyl group), a 1-butenyl group, a 2-butenyl group, a 3-butenyl group, an isobutyl group, 1-pentenyl group, 2-pentenyl group, 3-pentenyl group, 4-pentenyl group, 1-hexenyl group, 2-hexenyl group, 3-hexenyl group, 4-hexenyl group, and 5-hexenyl group. Examples of C2 to C6 alkynyl groups can include ethynyl group, 1-propynyl group, 2-propynyl group (propargyl group), 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynl group, and 1,1-dimethyl-2-butynyl group. Examples of a C1 to C7 alkoxyl group (when $R^8$ represents a C1 to C7 alkyl group at an organic oxy group represented by $OR^8$), can include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, 5-methylhexyloxy group, a 1-ethylpentyloxy group, a 2-ethylpentyloxy group, a 3-ethylpentyloxy group, a 4,4-dimethylpentyloxy group, and a 1-propylbutoxy group. $Z^1$, $Z^2$, $Z^3$ and $Z^4$ are the same or different, preferably hydrogen, an ethoxy group, fluorine, or chlorine.

$R^4$ and $R^5$ in the formula ($I_0$) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

An embodiment of the above formula ($I_0$), includes a compound represented by the following formula (I) and preferably a compound represented by the formula (1).

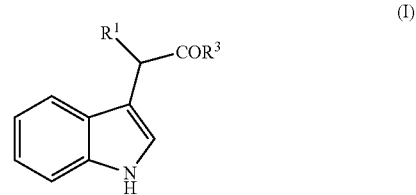

(I)

[wherein R¹ and R³ have the same meanings as defined in the above [1].]

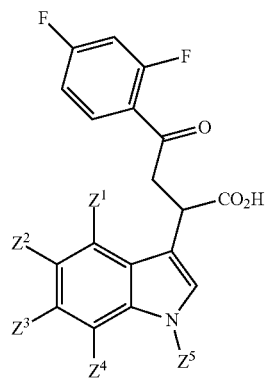

(1)

[wherein $Z^1$, $Z^2$, $Z^3$, $Z^4$ and $Z^5$ have the same meanings as defined in the above [1].]

In the compound of the above formula (1), $Z^1$, $Z^2$, $Z^3$ and $Z^4$ which are the same or different, are a hydrogen atom, a halogen atom, a C1 to C6 alkyl group, a C2 to C6 alkenyl group, a C2 to C6 alkynyl group, or an organic oxy group represented by $OR^8$, $R^8$ represents a C1 to C7 alkyl group, a C2 to C6 alkenyl group, or a C2 to C6 alkynyl group, $Z^5$ represents a hydrogen atom or a C1 to C6 alkyl group.

Examples of the halogen atom in the formula (1) can include a fluorine atom, a chlorine atom, a bromine atom, and an iodine atom.

The C1 to C6 alkyl group in the formula (1) means a linear or branched alkyl group having 1 to 6 carbon atoms which may have a substituent, and specific examples thereof can include methyl, ethyl, n-propyl, isopropyl, n-butyl, isobutyl, sec-butyl, tert-butyl, n-pentyl, isopentyl, neopentyl and n-hexyl groups.

Examples of the substituent of the above-mentioned "optionally have a substituent" can include a halogen atom, a hydroxyl group, a carboxyl group, an alkyl group having 1 to 6 carbon atoms, an alkenyl group having 2 to 6 carbon atoms, an alkynyl group having 2 to 6 carbon atoms and a C6 to C10 aryl group. The alkyl group having 1 to 6 carbon atoms, the alkenyl group having 2 to 6 carbon atoms and the alkynyl group having 2 to 6 carbon atoms are preferably the same as an alkyl group having 1 to 6 carbon atoms, an alkenyl having 2 to 6 carbon atoms group, and alkynyl group having 2 to 6 carbon atoms in the formula (1). Examples of the C6 to C10 aryl groups can include a phenyl group and a naphthyl group.

The C2 to C6 alkenyl group in the formula (1) means a linear or branched alkenyl group having 2 to 6 carbon atoms which optionally have a substituent, and specific examples thereof can include a vinyl group, 1-propenyl group, 2-propenyl group, 1-butenyl group, 2-butenyl group, 3-butenyl group, 1,3-butenyl group, 1-pentenyl group, and 1-hexenyl group.

The C2 to C6 alkynyl group in the formula (1) means a linear or branched alkynyl group having 2 to 6 carbon atoms which optionally have a substituent, and specific examples thereof can include an ethynyl group, 1-propynyl group, 1-butynyl group, 1-pentynyl group, and 1-hexynyl group.

$Z^1$, $Z^2$, $Z^3$ and $Z^4$ are preferably a hydrogen atom, a halogen atom, a C1 to C6 alkyl group, or an organic oxy group represented by OR8, preferably a hydrogen atom, a fluorine atom, a chlorine atom, a methyl group, an ethyl group, more preferably a C1 to C3 alkyl group such as a n-propyl group or an isopropyl group, and an organic oxy group represented by $OR^8$.

$Z^5$ is preferably a hydrogen atom or a C1 to C3 alkyl group, more preferably a hydrogen atom or a methyl group.

$R^8$ is preferably a C1 to C6 alkyl group, more preferably a C1 to C3 alkyl group such as a methyl group, an ethyl group, an n-propyl group or an isopropyl group, or a benzyl group.

Among the compounds represented by the above formula (1), the compounds represented by the following formula (2), formula (3), formula (4), formula (5), and formula (6) or the salts thereof are preferable.

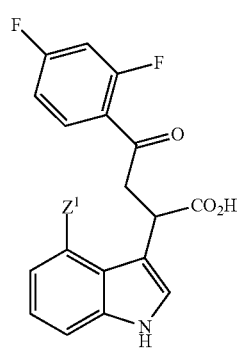

(2)

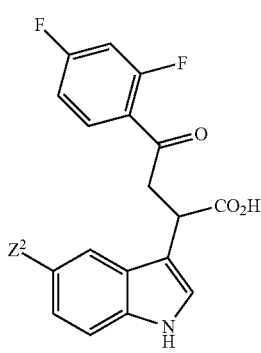

(3)

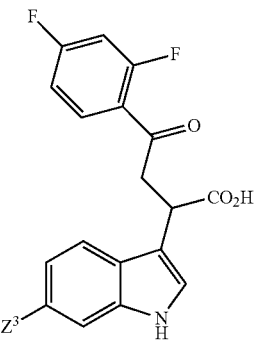

(4)

-continued
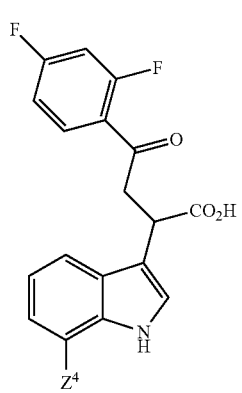
(5)
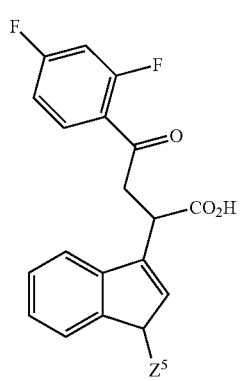
(6)
$Z^1$, $Z^2$, $Z^3$, $Z^4$, $Z^5$ in the above formulas (2), (3), (4), (5) and (6) have the same definitions as $Z^1$, $Z^2$, $Z^3$, $Z^4$, $Z^5$ in the formula (1).
Specifically, examples of the compound represented by the formula (1) can include the following compounds.
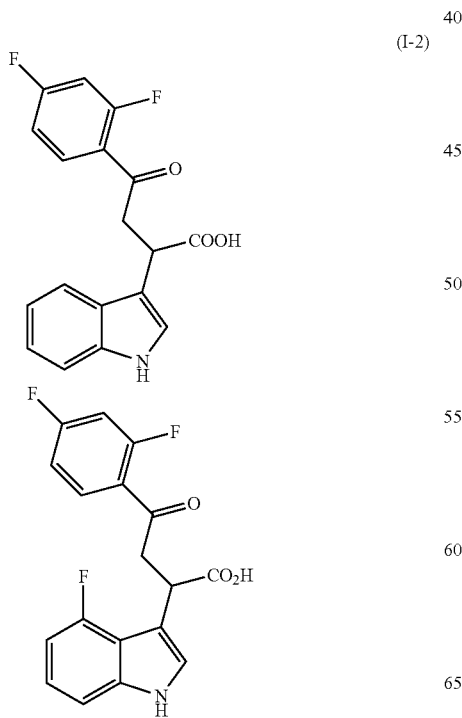
(I-2)
-continued
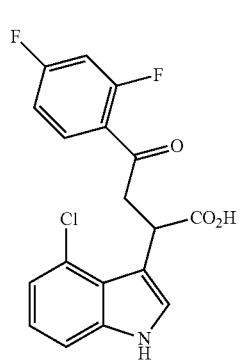
(2-1)
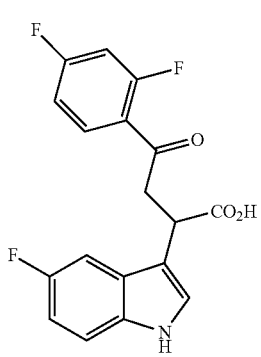
(3-1)
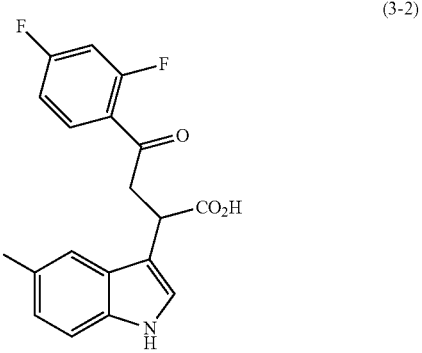
(3-2)
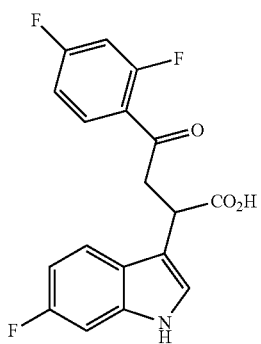
(4-1)

-continued
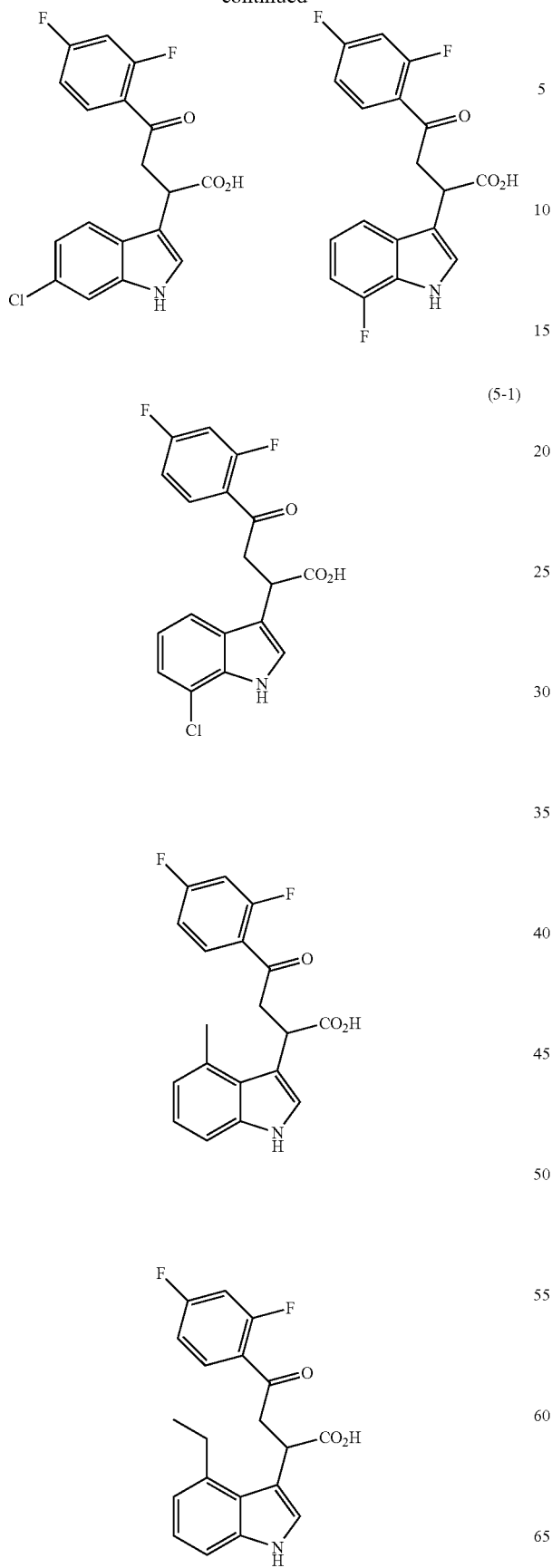
(5-1)
-continued
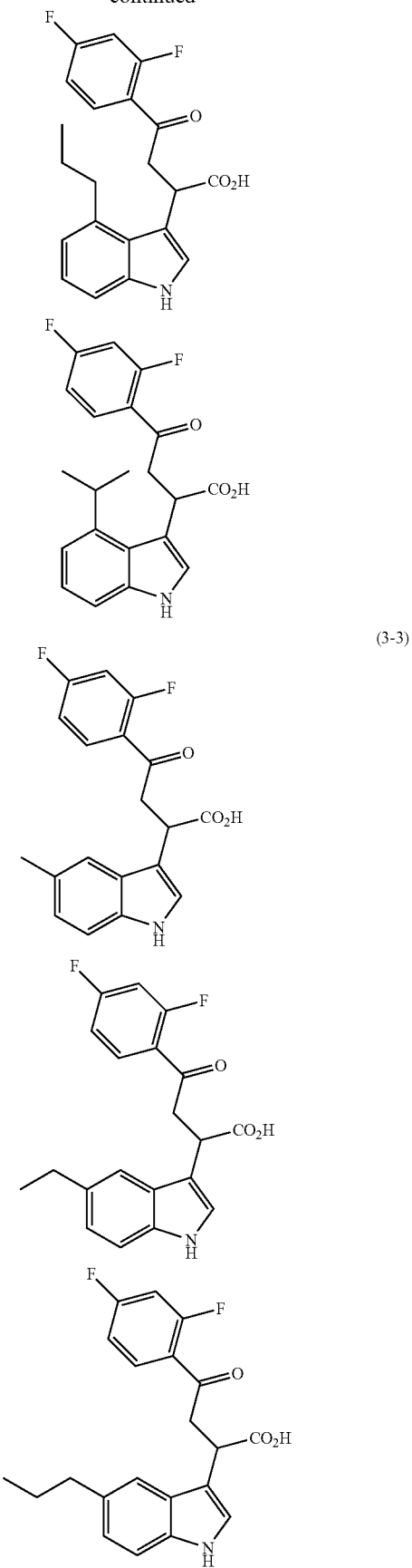
(3-3)

-continued
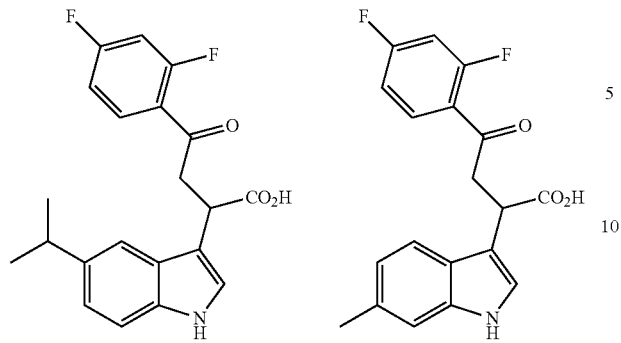
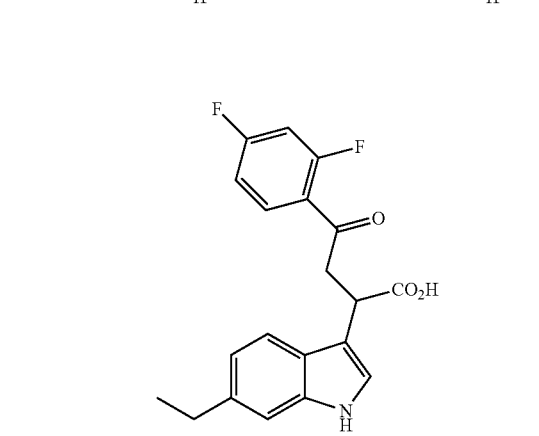
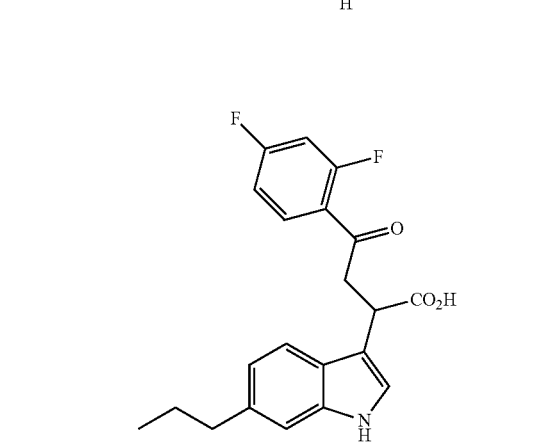
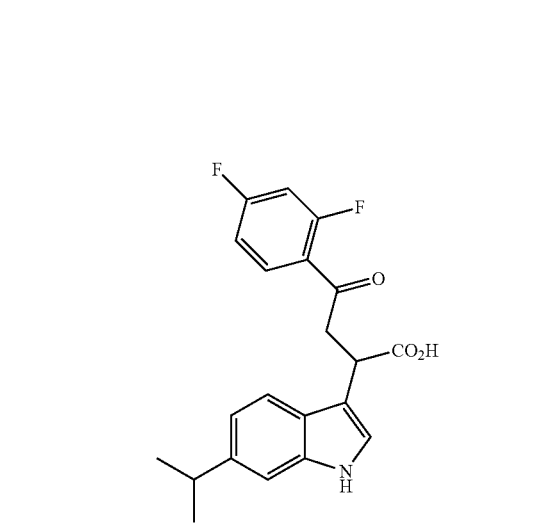
-continued
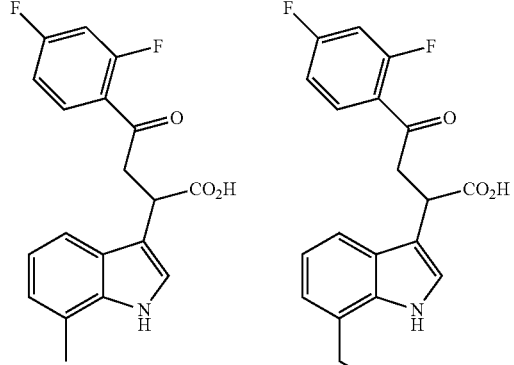
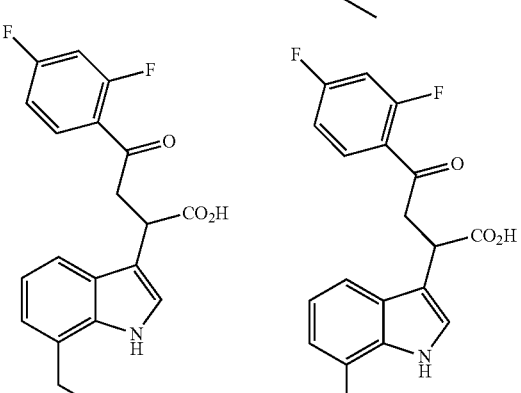
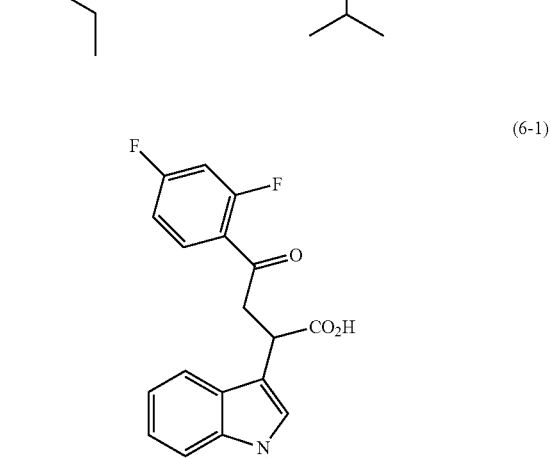
(6-1)
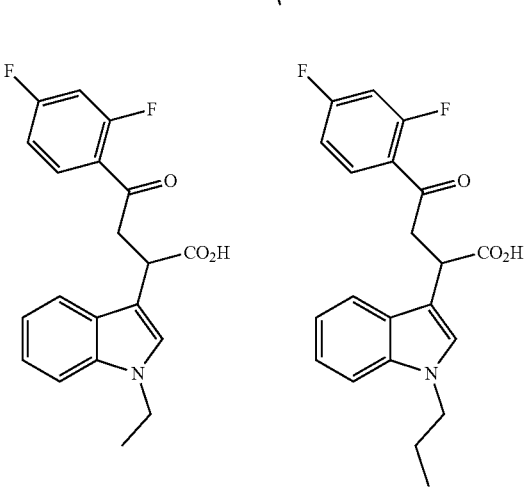

-continued
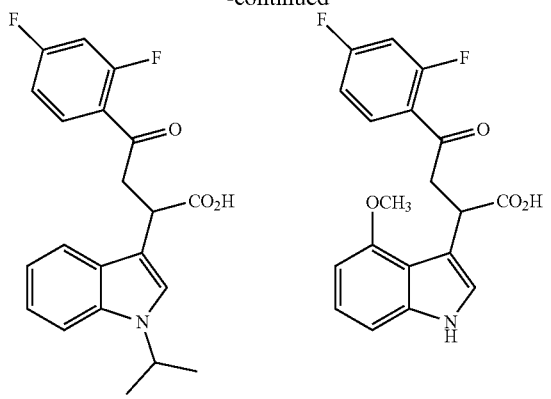
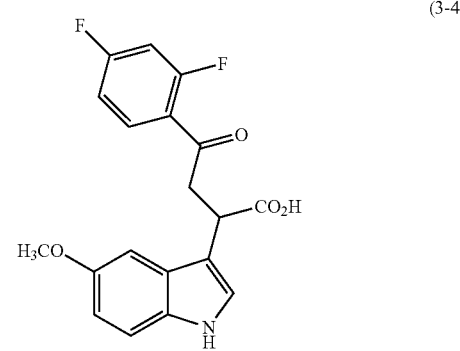
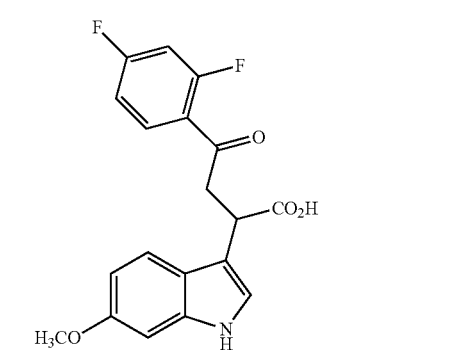
-continued
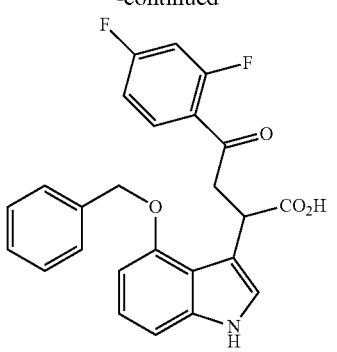
(3-4)
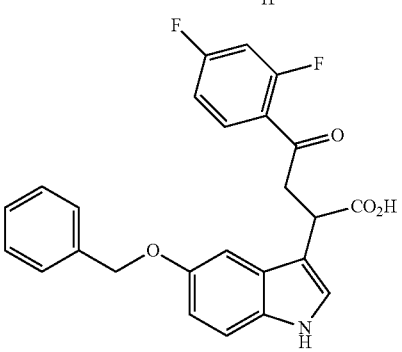
(4-2)
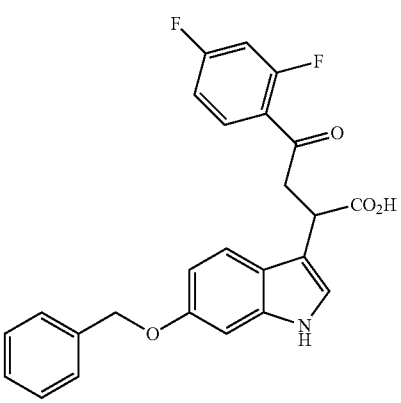
(5-2)
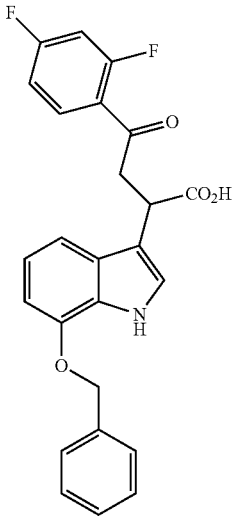
Among the above compounds, the following compounds are preferable.

(I-2)
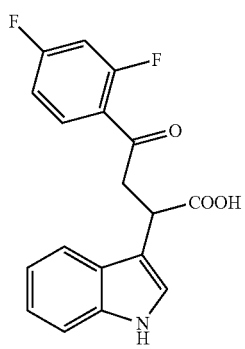
(4-1)
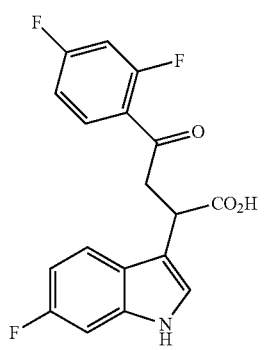
(3-1)
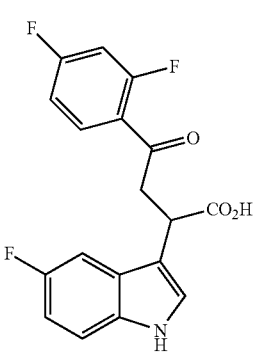
(5-1)
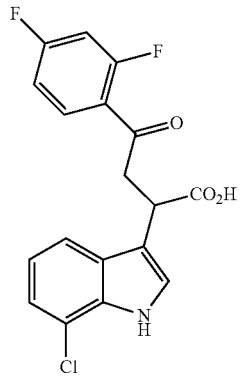
-continued
(3-2)
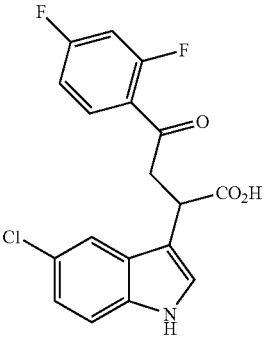
(2-1)
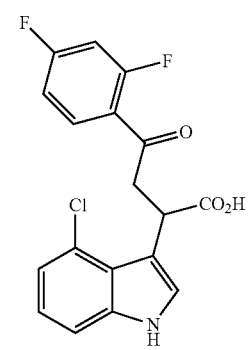
(3-3)
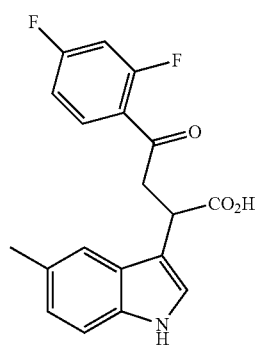
(6-1)
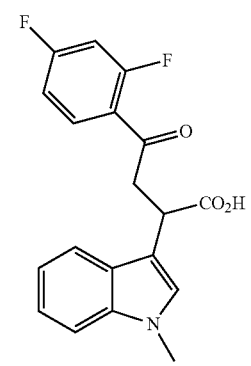

-continued

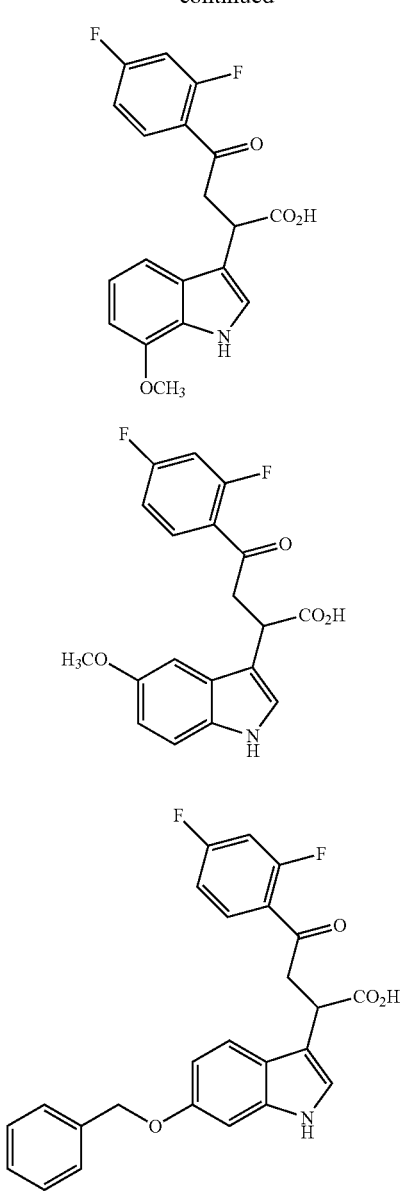

(5-2)

(3-4)

(4-2)

The compound represented by the formula ($I_0$) wherein $R^1$ is a 2,4-difluorobenzoylmethyl group, $Z^1$, $Z^2$, $Z^3$, $Z^4$, and $Z^5$ are hydrogen and $R^3$ is OH, represents compound #5 mentioned later in Examples. The compound represented by the formula ($I_0$) wherein $R^1$ is a 4-fluorobenzoylmethyl group, $Z^1$, $Z^2$, $Z^3$, $Z^4$, and $Z^5$ are hydrogen, and $R^3$ is OH represents compound #4 mentioned later in Examples. The compound represented by the formula ($I_0$) wherein $R^1$ is a 4,4,5,5,5-pentafluoropentyl group, $Z^1$, $Z^2$, $Z^3$, $Z^4$, and $Z^5$ are hydrogen, and $R^3$ is OH represents compound #21 mentioned later in Examples. The compound represented by the formula ($I_0$) wherein $R^1$ is a 2-cyclopentylethyl group, $Z^1$, $Z^2$, $Z^3$, $Z^4$, and $Z^5$ are hydrogen, and $R^3$ is OH represents compound #24 mentioned later in Examples. In addition to these compounds, specific examples of the compound represented by the formula ($I_0$) can include compounds #2, 4, 5, and 20 mentioned later in Examples, compounds #17 to 19 mentioned later in Examples, compounds #22 and 23 mentioned later in Examples, and compound #25 mentioned later in Examples.

X in the formula (II) is a linear alkylene group having 4 to 6 carbon atoms, i.e., butylene —($CH_2$)$_4$—, pentylene —($CH_2$)$_5$—, or hexylene —($CH_2$)$_6$—, or an ether group having 4 carbon atoms. Examples of the ether group having 4 carbon atoms can include a methylene-O-propylene group, an ethylene-O-ethylene group, and a propylene-O-methylene group. X is preferably butylene, hexylene, or an ethylene-O-ethylene group.

$R^4$ and $R^5$ in the formula (II) are the same or different and each represent a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (II) wherein X is butylene, $R^6$ is hydrogen, and $R^3$ is OH represents compound #15 mentioned later in Examples. In addition to the compound #15, specific examples of the compound represented by the formula (I) can include compound #13 mentioned later in Examples and compound #14 mentioned later in Examples.

$R^7$ in the formula (III) is an alkyl group having 1 to 5 carbon atoms or a benzyl group. Examples of the linear or branched alkyl group having 1 to 5 carbon atoms can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, and a 2,2-dimethylpropyl group. The benzene ring of the benzyl group is optionally substituted by one or more alkyl groups having 1 to 3 carbon atoms or alkoxyl groups having 1 to 3 carbon atoms. Examples of the alkyl group having 1 to 3 carbon atoms can include a methyl group, an ethyl group, a n-propyl group, and an isopropyl group. Examples of the alkoxy group having 1 to 3 carbon atoms can include a methoxy group, an ethoxy group, a n-propoxy group, and an isopropoxy group. $R^7$ in the formula (III) is preferably a methyl group, an ethyl group, a propyl group, a n-butyl group, a n-pentyl group, or a 3,5-dimethoxybenzyl group, more preferably a 3,5-dimethoxybenzyl group.

$R^4$ and $R^5$ in the formula (III) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (III) wherein A is indole, $R^7$ is a 3,5-dimethoxybenzyl group, and $R^3$ is OH represents compound #35 mentioned later in Examples. In addition to the compound #35, specific examples of the compound represented by the formula ($I_0$) can include compounds #36 to 38 mentioned later in Examples and compounds #33 and 34 mentioned later in Examples.

When a compound selected from compound group of the present invention has an asymmetric carbon atom and an axial chirality-related asymmetric point, this compound includes all possible optical isomers. These optical isomers can be used at an arbitrary ratio. For example, a certain optically active compound can be used as an enantiomer, a racemate, or an enantiomer mixture at an arbitrary ratio. A compound containing a plurality of asymmetric points can be used as a diastereomer mixture at an arbitrary ratio.

The pharmaceutically acceptable salts of compound group of the present invention include, for example, metal salts formed from aluminum, calcium, lithium, magnesium, potassium, sodium, and zinc, and organic salts formed from N,N'-dibenzylethylenediamine, chloroprocaine, choline, diethanolamine, ethylenediamine, N-methylglucamine, lysine, procaine, and the like.

Exemplary methods for synthesizing each compound selected from compound group of the present invention will be given below. However, the synthesis methods of the present invention are not limited to these methods, and generally known synthesis methods can be used. Compounds shown below can be obtained from Sigma-Aldrich Corp., Tokyo Chemical Industry Co., Ltd., Wako Pure Chemical Industries, Ltd., Kanto Chemical Co., Inc., etc. As for reaction solvents and reaction temperatures, a reaction is carried out using a solvent and a temperature usually used for the reaction, unless otherwise specified. Each reaction is carried out in an argon or nitrogen atmosphere. Each protective group can be used with reference to Green & Wuts, "PROTECTIVE GROUPS in ORGANIC SYNTHESIS" 3rd ed. John Wiley & Sons, Inc.

The compound represented by the formula ($I_0$) can be synthesized with substituted or unsubstituted benzene and substituted or unsubstituted indole as starting materials. First, substituted or unsubstituted benzene and maleic anhydride are used in Friedel-Crafts reaction to synthesize 4-aryl-4-oxo-2-butenoic acid. This Friedel-Crafts reaction is carried out by the action of a catalyst such as Lewis acid, phosphoric acid, or polyphosphoric acid. Aluminum chloride is preferably used as the catalyst. The reaction solvent is preferably a chlorine solvent. Alternatively, the starting material substituted or unsubstituted benzene can also be used as a solvent. The 4-aryl-4-oxo-2-butenoic acid thus obtained and substituted or unsubstituted indole are subjected to Michael reaction to obtain a compound in which the α-position of indoleacetic acid is substituted by a substituted or unsubstituted benzoyloxy group. In this way, the basic skeleton of the compound represented by the formula ($I_0$) can be constructed. In this Michael reaction, the carboxyl group of the 4-aryl-4-oxo-2-butenoic acid can or cannot be protected and, usually, does not have to be protected. When this carboxyl group is protected, examples of the protective group used can include methyl ester, tert-butyl ester, 2,2,2-trichloroethyl ester, and tert-butyldimethylsilyl ester. On the other hand, the nitrogen atom of the indole can or cannot be protected. When this nitrogen atom is protected, a benzyl protective group is preferred. An amide protective group is not preferred because of reducing reactivity. Also, the Michael reaction can proceed by the heating of the reaction system and can be carried out using a catalyst such as Lewis acid. After the obtainment of the skeleton of the compound represented by the formula ($I_0$), the protective group can be removed, if necessary, to synthesize the compound represented by the formula ($I_0$). Then, the carboxylic acid moiety can also be appropriately esterified, amidated, or converted to a pharmaceutically acceptable salt according to the purpose. Specifically, compound #5 mentioned later in Examples can be synthesized from 1,3-difluorobenzene, maleic anhydride, and indole as shown in the following scheme:

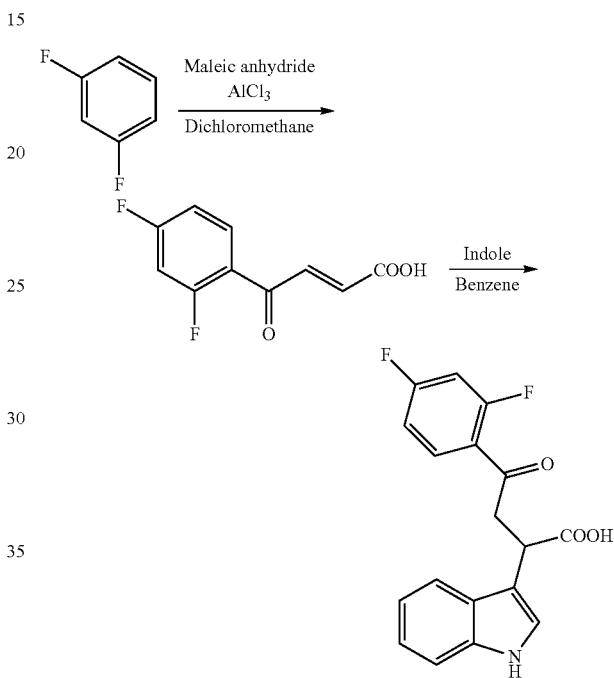

In an alternative aspect, examples of the method for synthesizing the compound represented by the formula ($I_0$) can include a synthesis method using an alcohol and a protected form of indoleacetic acid as starting materials. The hydroxy group of the alcohol can be converted to iodine or bromine either directly or through two-step reaction. Examples of the method involving direct conversion can include, but are not limited to, a method of substituting the alcohol by iodine (I•) by the action of triphenylphosphine, imidazole, and iodine ($I_2$), and a method of substituting the alcohol by bromine by the action of triphenylphosphine and carbon tetrabromide. Examples of the synthesis method through a plurality of steps can include a method of derivatizing the alcohol into a sulfonic acid ester such as methanesulfonate, trifluoromethanesulfonate, or toluenesulfonate, followed by reaction with an iodide salt of an alkali metal or a bromide salt of an alkali metal. The halogen form thus obtained can be nucleophilically reacted with enolate at the α-position formed from the protected form of indoleacetic acid to obtain the basic skeleton of the compound represented by the formula ($I_0$). Examples of the protective group for the indoleacetic acid include a method of derivatizing the indoleacetic acid into methyl ester, tert-butyl ester, 2,2,2-trichloroethyl ester, or tert-butyldimethylsilyl ester for the protection of the carboxyl group. On the other hand, the amine site of the indoleacetic acid is preferably protected as amide carbonate. Examples of the protective group can include methoxycarbonyl, ethoxycarbonyl, tert-butoxycarbonyl, and benzyloxycarbonyl. The protected form of the indoleacetic acid thus obtained is derivatized into enolate by the action of a base. The formed enolate and the halogen form can be subjected to nucleophilic reaction to obtain the basic skeleton of the compound represented by the formula ($I_0$). Examples of the base that can be used in this nucleophilic reaction can include: a carbonate of an alkali metal such as lithium carbonate, sodium carbonate, potassium carbonate, and cesium carbonate; an alkyllithium such as methyllithium, n-butyllithium, sec-butyllithium, and tert-butyllithium; and an alkali metal amide such as lithium diisopropylamide, lithium hexamethyldisilazane, sodium hexamethyldisilazane, and potassium hexamethyldisilazane. The solvent that can be used differs depending on the base used and is preferably an aprotic polar solvent such as N,N-dimethylformamide (DMF) or tetrahydrofuran (THF). The addition of hexamethylphosphoric triamide or the like is effective for promoting the reaction. The protective group can be removed from the protected form thus obtained to obtain the compound of interest. Then, the carboxylic acid moiety can be appropriately esterified, amidated, or converted to a pharmaceutically acceptable salt thereof. Specifically, compound #21 mentioned later in Synthesis Examples can be synthesized with 4,4,5,5,5-pentafluoropentanol and 1-methoxycarbonyl-3-indoleacetic acid methyl ester as starting materials as shown in the following scheme:

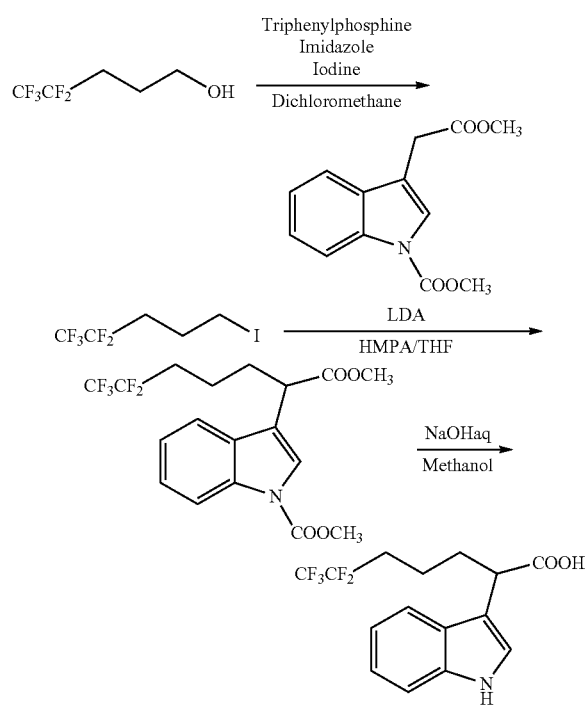

The compound represented by the formula (1) in the present invention can be obtained by an organic synthesis technique using a known organic chemical reaction. For example, by subjecting (E)-4-(2,4-difluorophenyl)-4-oxo-2-butenoic acid and an indole derivative represented by formula (7) to Michael reaction as shown below, the compound represented by the formula (1) can be obtained.

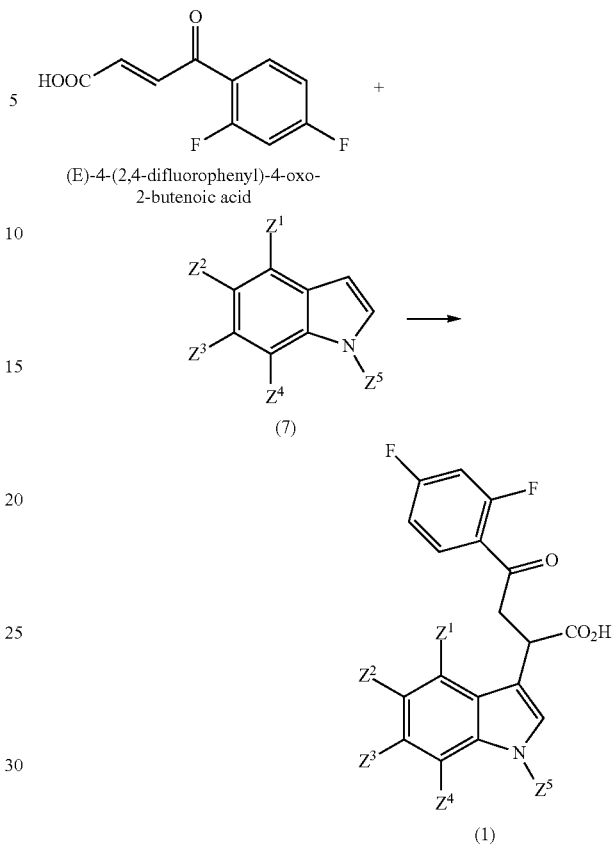

($Z^1$, $Z^2$, $Z^3$, $Z^4$, and $Z^5$ in the above formula (7) have the same definition as $Z^1$, $Z^2$, $Z^3$, $Z^4$, and $Z^5$ in the formula (1).

The (E)-4-(2,4-difluorophenyl)-4-oxo-2-butenoic acid can be synthesized by Friedel-Crafts reaction of 1,3-difluorobenzene and maleic anhydride as shown below. Such Friedel-Crafts reaction is carried out by causing Lewis acid, phosphoric acid, polyphosphoric acid or the like to act as a catalyst, and aluminum chloride is suitably used as a catalyst.

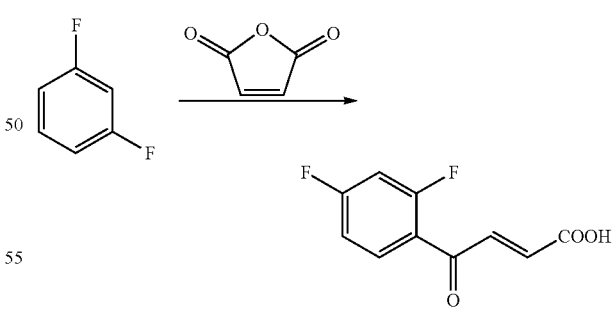

As the indole derivative represented by the above formula (7), a commercially available product can be used. Commercially available indole derivatives can include 4-fluoroindole, 4-chloroindole, 4-bromoindole, 6-fluoroindole, 6-chloroindole, 6-bromoindole, 5-methylindole, or the like.

In addition, the indole derivative represented by the above formula (7) can also be obtained by an organic synthesis technique using a known organic chemical reaction. For example, when $R^1$, $R^2$, $R^3$, $R^4$ and $R^5$ are a halogen atom, a halogenating agent such as N-bromosuccinimide, N-chlorosuccinimide, or N-iodosuccinimide can be allowed to act on a commercially available indole to obtain the indole derivative represented by the above formula (7). When $R^1$, $R^2$, $R^3$ and $R^4$ are a C1 to C6 alkyl group, a C2 to C6 alkenyl group, a C2 to C6 alkynyl group, and an organic oxy group represented by $OR^8$, commercially available indole as mentioned above can be halogenated, followed by reaction with an organolithium reagent such as alkyllithium or Suzuki-Miyaura coupling reaction to obtain an indole derivative represented by the above formula (7). Further, when $R^5$ is a C1 to C6 alkyl group, it is possible to obtain an indole derivative represented by the above formula (7) by reacting a C1 to C6 alkyl halide such as bromomethane and bromoethane with a commercially available indole.

All of the organic reactions described above can be carried out in a solvent, respectively, but the solvent is appropriately selected depending on the reaction temperature, reactants and the like. The reaction temperature of the organic reaction is appropriately selected depending on the conditions such as the boiling point of the solvent to be used. When a solvent is used in the above organic reaction, the obtained reaction solution may be concentrated as necessary, and the residue may be then used as it is for the next reaction. After appropriate post-treatment, the residue may be used as the compound represented by the formula (1). Specific methods for post-treatment can include extraction treatment and/or known purification such as crystallization, recrystallization, chromatography.

The aforementioned method for synthesizing the compound represented by the formula ($I_0$) can also be used for synthesizing the compound represented by the formula (II). Specifically, the compound represented by the formula (II) can be synthesized in the same way as the aforementioned method for synthesizing the compound represented by the formula ($I_0$) except that a linear amino alcohol with an amino group protected with tert-butoxycarbonyl or a linear amino alcohol having oxygen in the chain and a protected form of indoleacetic acid in which the α-position is substituted by a methyl group are used as starting materials, instead of the alcohol and the protected form of indoleacetic acid used as starting materials. The linear amino alcohol and the linear amino alcohol having oxygen in the chain can each be converted to tert-butoxycarbonylamide by a standard method. Usually, di-tert-butyl carbonate is used. Those skilled in the art readily understand that the protected form of indoleacetic acid in which the α-position is substituted by a methyl group is an intermediate obtained using methyl iodide as the halogen form in the method for synthesizing the compound represented by the formula ($I_0$). The starting materials thus prepared can be used in the same way as the method for synthesizing the compound represented by the formula ($I_0$) to synthesize the compound represented by the formula (II). Specifically, compound #15 mentioned later in Examples can be synthesized as 4-aminobutanol and 1-methoxycarbonyl-3-indoleacetic acid methyl ester as starting materials as shown in the following scheme:

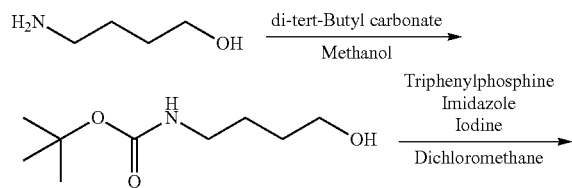

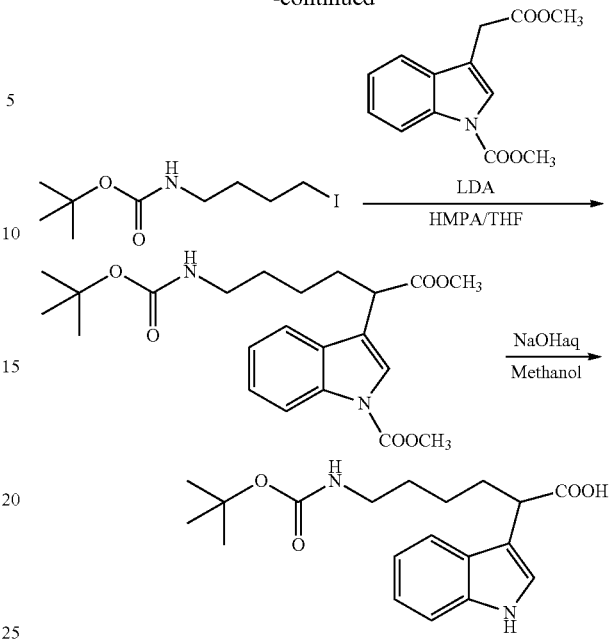

The compound represented by the formula (III) wherein A is indole or naphthalene can be commonly synthesized with 5-hydroxy-3-indoleacetic acid ester or α-(7-hydroxy-1-naphthalenyl)-acetic acid ester as a starting material. The 5-hydroxy-3-indoleacetic acid ester and the α-(7-hydroxy-1-naphthalenyl)-acetic acid ester can be obtained by the esterification of corresponding carboxylic acids. The 5-hydroxy-3-indoleacetic acid and the α-(7-hydroxy-1-naphthalenyl)-acetic acid have three active protons and two active protons, respectively, which present problems associated with reaction selectivity. For this reason, the alcohol moieties of these compounds are protected, and the protective group can be removed after the esterification to obtain the starting material. Alternatively, α-(7-hydroxy-1-naphthalenyl)-acetic acid ethyl ester can also be synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011. In addition, a method for synthesizing the 5-hydroxy-3-indoleacetic acid ester can involve synthesizing an ester with an alcohol used as a solvent with favorable selectivity through a reaction under acidic conditions in a dried alcohol. Examples of conditions for the esterification reaction can include commercially available hydrochloric acid/methanol and a method of blowing dried hydrochloric acid into a dehydrated alcohol. A method of adding dropwise acid chloride to a preliminarily dried alcohol to generate an acid in the system is preferred. Then, the carboxylic acid moiety can be appropriately esterified, amidated, or converted to a pharmaceutically acceptable salt thereof. The starting material thus prepared can be reacted with alkyl iodide or alkyl bromide to construct the basic skeleton of the compound represented by the formula (III). Examples of the base used in this reaction of the 5-hydroxy-3-indoleacetic acid ester or the 7-hydroxy-1-naphthalenylacetic acid ester with alkyl iodide or alkyl bromide include sodium hydride and a carbonate of an alkali metal such as lithium carbonate, sodium carbonate, potassium carbonate, and cesium carbonate. The reaction solvent is preferably an aprotic polar solvent such as DMF or THF.

After the obtainment of the skeleton of the compound represented by the formula (III), the protective group can be removed, if necessary, to synthesize the compound represented by the formula (III). Then, the carboxylic acid moiety can also be appropriately esterified, amidated, or converted to a pharmaceutically acceptable salt according to the purpose. Specifically, compound #34 mentioned later in Examples can be synthesized with 1-iodobutane and α-(7-hydroxy-1-naphthalenyl)-acetic acid ethyl ester as starting materials as shown in the following scheme:

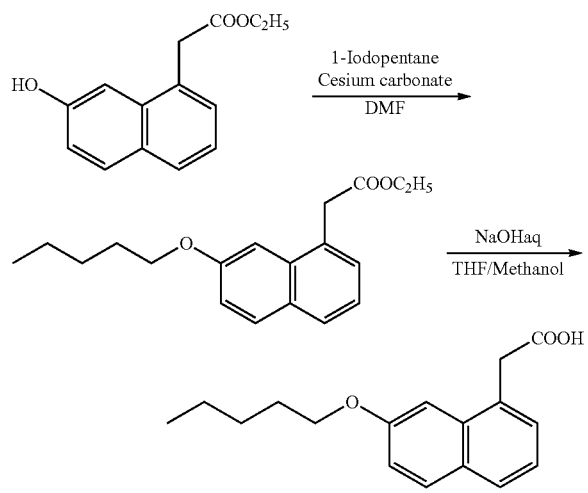

Similarly, compound #35 mentioned later in Examples can be synthesized using 3,5-dimethoxybenzyl bromide and 7-hydroxy-3-indoleacetic acid as starting materials.

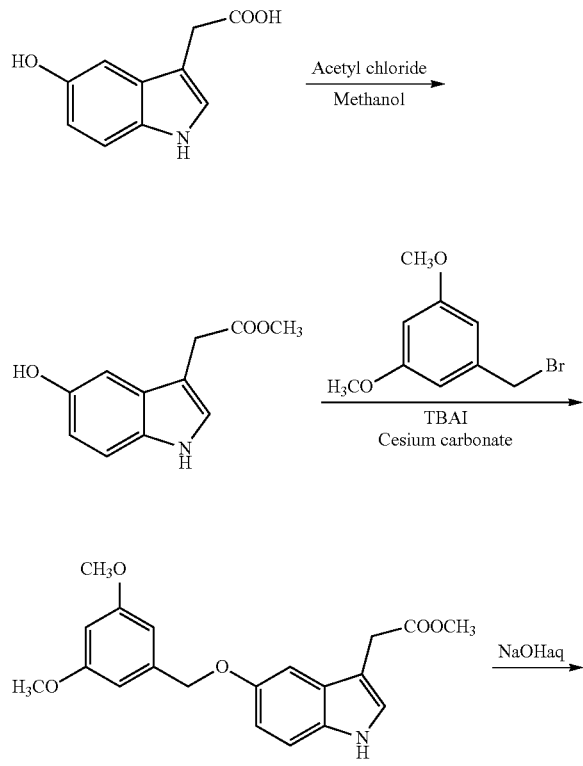

-continued

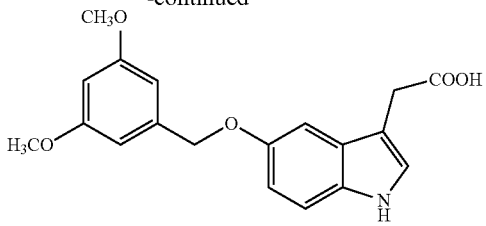

As the compound group of the present invention, compound #5 is preferred of which effect is specifically shown in the examples of the present specification.

The preventive/improving agent of the present invention can include conventional pharmaceutically acceptable ingredients such as a carrier, a binder, a stabilizer, an excipient, a diluent, a pH buffer, a disintegrant, a tonicity agent, an additive, a coating agent, a solubilizer, a lubricant, a glidant, a solubilization aid, a lubricating agent, a flavoring agent, a sweetener, a solvent, a gelling agent, and a nutrient. Specific examples of such formulation ingredients can include water, saline, animal fat and oil, plant oil, lactose, starch, gelatin, crystalline cellulose, gum, talc, magnesium stearate, hydroxypropylcellulose, polyalkylene glycol, polyvinyl alcohol, and glycerin.

Examples of the administration mode of the preventive/improving agent of the present invention can include oral administration based on administration in a dosage form such as powders, granules, a tablet, a capsule, a syrup, or a suspension, and parenteral administration based on injection in a dosage form such as a solution, an emulsion, or a suspension or administration into the nasal cavity in the form of a spray.

The dose amount of the preventive/improving agent of the present invention is determined adaptively according to age, body weight, sex, symptom, susceptibility to a drug, and is, for example, a dose range of 1 μg to 200 mg/kg (body weight)/day. With respect to the Example described later, the dosage of Compound #5 at 0.3 to 10 mg/kg/day is specifically shown by an experiment using a model mouse. Based on the human equivalent dose (HED) in mice 12.3 (see the document "Guidance for Industry Estimating the Maximum Safe Starting Dose in Initial Clinical Trials for Therapeutics in Adult Healthy Volunteers"), it is 24.4 to 813 μg/kg/day in terms of the dosage for human. Therefore, the dose of the present preventive/therapeutic agent is preferably 1 μg to 100 mg/kg/day, more preferably 5 μg to 50 mg/kg/day, still more preferably 10 μg to 10 mg/kg/day, even more preferably 15 μg to 5 mg/kg/day, and most preferably 20 μg to 1.0 mg/kg/day. The preventive/therapeutic agent of the present invention is administered in single or multiple doses (for example, 2 to 4 times) per day, but the dosage may be adjusted according to the situation of improvement in symptoms.

The preventive/improving agent of the present invention may contain a preventive or improving component of hearing loss other than the compound group of the present invention. However, in order to exhibit excellent preventive or improving effect of hearing loss even with the compound group of the present invention alone, the present compound those which do not contain components for preventing or improving hearing loss (e.g., proteins, DNA, RNA, plant-derived extracts) other than the compound group of the present invention are preferable.

Hereinafter, the present invention will be described more specifically with reference to Examples. However, the technical scope of the present invention is not intended to be limited by these examples.

Example 1

1. Synthesis of Compound Group of the Present Invention

Starting materials for synthesis, reaction reagents, etc., for use in methods for synthesizing compounds shown below are general commercially available products. As for reaction solvents and reaction temperatures, a reaction is carried out using a solvent and a temperature usually used for the reaction, unless otherwise specified. Each reaction is carried out in an argon or dried nitrogen atmosphere.

Synthesis of Compound #1

4-Phenyl-2-(4-chloro-1H-indol-3-yl)-4-oxo-butane (compound #1) was synthesized by a method for synthesizing compound #20 mentioned later using 4-chloroindole instead of indole.

Synthesis of Compound #2 and Compound #3

4-(4-Chlorophenyl)-2-(1H-indol-3-yl)-4-oxo-butanoic acid (compound #2) and 3-(1H-indol-3-yl)-1-oxo-1-phenyl-butane (compound #3) were each synthesized according to a method described in Sayed, G. H. et al, "Synthesis and reactions of some β-aroyl-α-(indol-3-yl)propionic acids" Journal of the Chemical Society of Pakistan, 7 (4), 263-72; 1985.

(Compound #2)

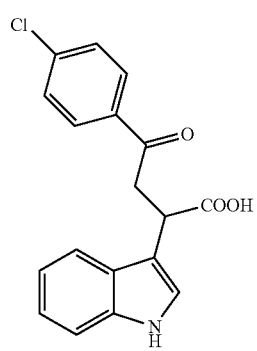
(I-1)

Synthesis of Compound #4

Trans-4-(4-fluorophenyl)-4-oxo-2-butenoic Acid

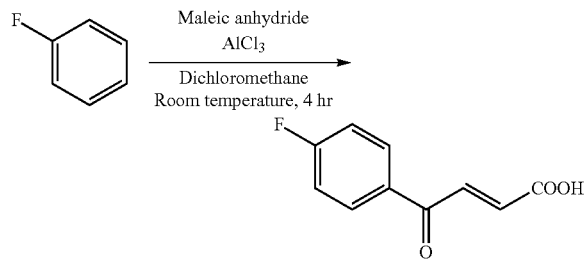

In a 50-mL round-bottomed flask filled with nitrogen, fluorobenzene (0.50 g, 5.21 mmol) was dissolved in dichloromethane (20 mL). To the solution, maleic anhydride (0.51 g, 5.20 mmol) and aluminum chloride (1.40 g, 10.49 mmol) were added, and the mixture was stirred at room temperature for 4 hours. The reaction solution was pH-adjusted to 1 by the addition of 1 N hydrochloric acid (10 mL), followed by extraction with ethyl acetate (40 mL) three times. The organic layer was washed with saturated saline and dehydrated over anhydrous sodium sulfate. The solvent was distilled off under reduced pressure, and then, the residue was purified by recrystallization (benzene) to obtain trans-4-(4-fluorophenyl)-4-oxo-2-butenoic acid (0.57 g, yield: 56%); Melting point: 114.8 to 119.6° C.; $^1$H NMR (CDCl$_3$): δ 8.06 (m, 2H), 7.98 (d, J=15.4 Hz, 1H), 7.21 (m, 2H), 6.90 (d, J=15.4 Hz, 1H); $^{13}$C NMR (CDCl$_3$): δ 187.5, 170.7, 166.3 (d, J$_{C-F}$=255.5 Hz), 138.0, 132.8 (d, J$_{C-F}$=3.2 Hz), 131.7 (d, J$_{C-F}$=9.9 Hz), 131.6, 116.2 (d, J$_{C-F}$=22.1 Hz); IR (neat): 2972, 1705, 1665 cm$^{-1}$; FAB-MS m/z 195 [M+H]$^+$.

4-(4-Fluorophenyl)-2-(1H-indol-3-yl)-4-oxo-butanoic Acid (Compound #4)

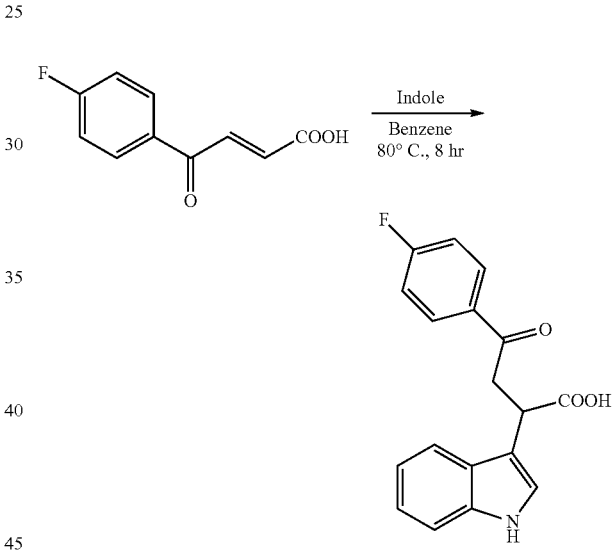

In a 30-mL round-bottomed flask, trans-4-(4-fluorophenyl)-4-oxo-2-butenoic acid (0.21 g, 1.08 mmol) was dissolved in benzene (10 mL). To the solution, indole (0.26 g, 2.19 mmol) was added, and the mixture was stirred at 80° C. for 8 hours and stirred until the temperature became room temperature. The solvent in the reaction solution was distilled off under reduced pressure, and the residue was purified using silica gel column chromatography (chloroform:methanol=20:1) to obtain 4-(4-fluorophenyl)-2-(1H-indol-3-yl)-4-oxo-butanoic acid (compound #4) (0.15 g, yield: 47%); Melting point: 161.6 to 166.6° C.; $^1$H NMR (DMSO-d$_6$): δ 8.13 (m, 2H), 7.68 (d, J=7.9 Hz, 1H), 7.35 (m, 4H), 7.09 (t, J=7.2 Hz, 1H), 7.00 (t, J=7.1 Hz, 1H), 4.34 (dd, J=10.7, 3.9 Hz, 1H), 4.03 (dd, J=18.1, 10.7 Hz, 1H), 3.34 (dd, J=18.1, 3.9 Hz, 1H); $^{13}$C NMR (DMSO-d$_6$): δ 197.96, 175.61, 166.00 (d, J$_{C-F}$=250.0 Hz), 137.16, 134.11, 131.93 (d, J$_{C-F}$=10.0 Hz), 127.15, 124.16, 122.07, 119.97, 119.53, 116.6 (d, J$_{C-F}$=22.0 Hz), 112.79, 112.42, 42.03, 38.57; IR (neat): 3419, 2925, 1679 cm$^{-1}$; HRFAB-MS found m/z 312.1028 [M+H]$^+$, calcd for 312.1036 (C$_{18}$H$_{15}$FNO$_3$).

Synthesis of Compound 5

Trans-4-(2,4-difluorophenyl)-4-oxo-2-butenoic Acid

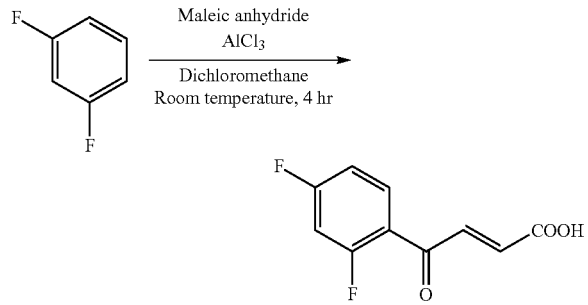

In a 50-mL round-bottomed flask filled with nitrogen, 1,3-difluorobenzene (0.51 g, 4.47 mmol) was dissolved in dichloromethane (20 mL). To the solution, maleic anhydride (0.43 g, 4.46 mmol) and aluminum chloride (1.20 g, 9.01 mmol) were added, and the mixture was stirred at room temperature for 4 hours and stirred until the temperature became room temperature. The reaction solution was pH-adjusted to 1 by the addition of 1 N hydrochloric acid (10 mL), followed by extraction with ethyl acetate (40 mL) three times. The organic layer was washed with saturated saline and dehydrated over anhydrous sodium sulfate. The solvent was distilled off under reduced pressure, and then, the residue was purified by recrystallization from benzene to obtain trans-4-(2,4-difluorophenyl)-4-oxo-2-butenoic acid (0.57 g, yield: 56%); Melting point: 114.8 to 119.6° C.; $^1$H NMR (acetone-$d_6$): δ 7.98 (m, 1H), 7.71 (dd, $J_H$-F=15.6, 3.4 Hz, 1H), 7.23 (m, 2H), 6.75 (dd, $J_H$-F=15.6, 1.2 Hz, 1H); $^{13}$C NMR (acetone-$d_6$): δ 187.2 (d, $J_{C-F}$=2.6 Hz), 166.9 (dd, $J_{C-F}$=254.5, 12.3 Hz), 166.4, 163.4 (dd, $J_{C-F}$=254.5, 12.9 Hz), 140.0 (d, $J_{C-F}$=6.1 Hz), 134.0 (dd, $J_{C-F}$=10.9, 3.6 Hz), 133.0 (d, $J_{C-F}$=1.6 Hz), 123.3 (dd, $J_{C-F}$=12.4, 3.6 Hz), 113.4 (dd, $J_{C-F}$=21.5, 3.6 Hz), 105.8 (dd, $J_{C-F}$=27.3, 26.3 Hz); IR (neat): 2917, 1697, 1661 cm$^{-1}$; FAB-MS m/z 213 [M+H]$^+$.

4-(2,4-Difluorophenyl)-2-(1H-indol-3-yl)-4-oxo-butanoic Acid (Compound #5)

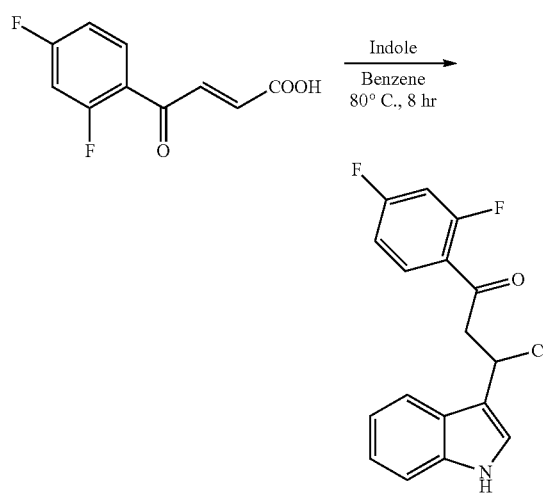

In a 30-mL round-bottomed flask, trans-4-(2,4-difluorophenyl)-4-oxo-2-butenoic acid (0.39 g, 1.84 mmol) was dissolved in benzene (10 mL). To the solution, indole (0.43 g, 2.19 mmol) was added, and the mixture was stirred 80° C. for 8 hours and stirred until the temperature became room temperature. The solvent in the reaction solution was distilled off under reduced pressure, and the residue was purified using silica gel column chromatography (chloroform:methanol=20:1) to obtain 4-(2,4-difluorophenyl)-2-(1H-indol-3-yl)-4-oxo-butanoic acid (0.15 g, yield: 51%); Melting point: 180.2 to 184.6° C.; $^1$H NMR (DMSO-$d_6$): δ 7.98 (m, 1H), 7.65 (d, J=7.9 Hz, 1H), 7.37 (d, J=8.1 Hz, 1H), 7.42 (m, 1H), 7.28 (d, J=2.3 Hz, 1H), 7.24 (m, 1H), 7.09 (t, J=7.1 Hz, 1H), 7.01 (t, J=7.5 Hz, 1H), 4.34 (dd, J=10.5, 3.5 Hz, 1H), 3.90 (ddd, $J_H$-F=18.5, 10.6, 2.4 Hz, 1H), 3.30 (ddd, $J_{H-F}$=18.5, 6.1, 3.5 Hz, 1H); $^{13}$C NMR (DMSO-$d_6$): δ 195.2 (d, $J_{C-F}$=4.1 Hz), 174.8, 165.2 (d, $J_{C-F}$=253.0, 13.4 Hz), 162.2 (d, $J_{C-F}$=255.5, 13.4 Hz), 136.4, 132.7 (dd, $J_{C-F}$=10.8, 4.1 Hz), 126.3, 123.3, 122.2 (dd, $J_{C-F}$=12.3, 3.6 Hz), 121.4, 119.1, 118.8, 112.6 (dd, $J_{C-F}$=21.1, 3.6 Hz), 111.9, 111.8, 105.4 (dd, $J_{C-F}$=26.1 Hz), 45.6 (d, $J_{C-F}$=6.3 Hz), 37.9; IR (neat): 3382, 2919, 1678 cm$^{-1}$; HRFA-MS found m/z 330.0910 [M+H]$^+$, calcd for 330.0942 ($C_{18}H_{14}F_2NO_3$).

Synthesis of Compound #6

Trans-4-(2,4-dimethylphenyl)-4-oxo-2-butenoic Acid

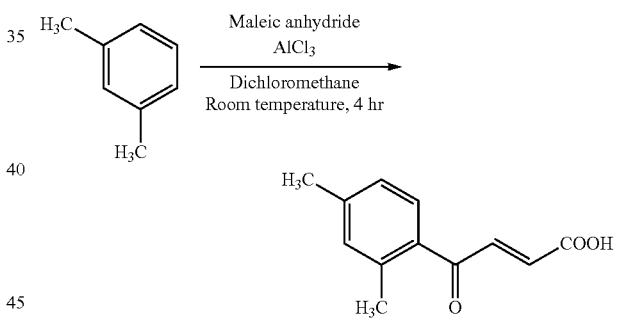

In a 50-mL round-bottomed flask filled with nitrogen, m-xylene (1.00 g, 9.42 mmol) was dissolved in dichloromethane (40 mL). To the solution, maleic anhydride (0.93 g, 9.42 mmol) and aluminum chloride (2.51 g, 18.84 mmol) were added, and the mixture was stirred at room temperature for 4 hours. The reaction solution was pH-adjusted to 1 by the addition of 1 N hydrochloric acid (10 mL), followed by extraction with ethyl acetate (40 mL) three times. The organic layer was washed with saturated saline and dehydrated over anhydrous sodium sulfate. The solvent was distilled off under reduced pressure, and then, the residue was purified by recrystallization (benzene) to obtain trans-4-(2,4-dimethylphenyl)-4-oxo-2-butenoic acid (1.49 g, yield: 77%); Melting point: 85.4 to 88.8° C.; $^1$H NMR (CDCl$_3$): δ 7.75 (d, J=15.6 Hz, 1H), 7.56 (d, J=8.2 Hz, 1H), 7.10 (m, 2H), 6.70 (d, J=15.6 Hz, 1H), 2.50 (s, 3H), 2.38 (s, 3H); $^{13}$C NMR (CDCl$_3$): δ 192.5, 170.9, 143.1, 141.7, 139.5, 133.6, 133.0, 130.9, 130.0, 126.4, 21.5, 21.2; IR (neat): 2986, 1703, 1667 cm$^{-1}$; FAB-MS m/z 205 [M+H]$^+$.

4-(2,4-Dimethylphenyl)-2-(1-propyl-1H-indol-3-yl)-4-oxo-butanoic Acid (Compound #6)

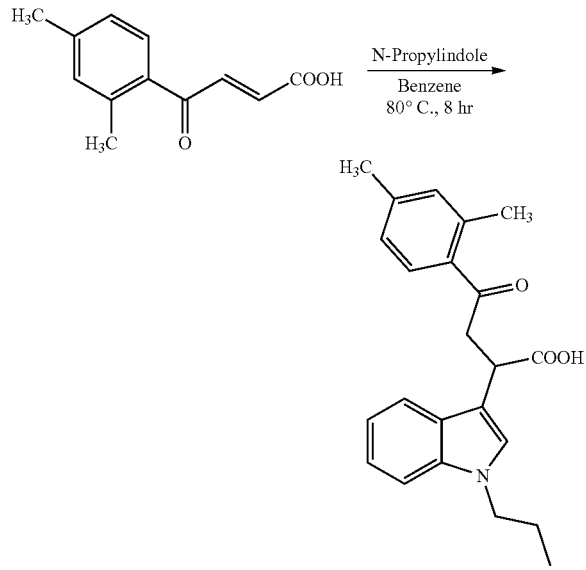

In a 30-mL round-bottomed flask, trans-4-(2,4-dimethylphenyl)-4-oxo-2-butenoic acid (0.50 g, 2.45 mmol) was dissolved in benzene (10 mL). To the solution, N-propylindole (0.85 g, 4.90 mmol) was added, and the mixture was stirred at 80° C. for 8 hours and stirred until the temperature became room temperature. The solvent in the reaction solution was distilled off under reduced pressure, and the residue was purified using silica gel column chromatography (chloroform:acetone=5:1) to obtain 4-(2,4-dimethylphenyl)-2-(1-propyl-1H-indol-3-yl)-4-oxo-butanoic acid (0.98 g, yield: 67%); Melting point: 139 to 141° C.; $^1$H NMR (400 MHz, CDCl$_3$): δ 7.70 (d, J=7.8 Hz, 1H), 7.59 (d, J=7.8 Hz, 1H), 7.28 (d, J=8.2 Hz, 1H), 7.18 (t, J=15.1 Hz, 1H), 7.07 (m, 2H), 6.99 (d, J=8.7 Hz, 2H), 4.56 (dd, J=6.0, 4.1 Hz, 1H), 3.97 (m, 2H), 3.92 (m, 1H), 3.28 (dd, J=17.8, 4.1 Hz, 1H), 2.43 (s, 3H), 2.30 (s, 3H), 1.80 (m, 2H), 0.89 (t, J=14.7, 3H); $^{13}$C NMR (100 MHz, CDCl$_3$): δ 200.9, 179.7, 142.3, 138.9, 136.3, 134.1, 132.8, 129.1, 126.7, 126.2, 126.1, 121.7, 119.4, 119.2, 110.6, 109.5, 48.0, 44.0, 38.0, 23.4, 21.5, 21.3, 11.5; IR (neat): 3428, 2923, 1707 cm$^{-1}$; FAB-MS m/z 364 [M+H]$^+$.

4-Phenyl-2-(1H-5-ethoxyindol-3-yl)-4-oxo-butanoic acid (compound #7) was synthesized in the same way as in compound #20 using 5-ethoxyindole instead of indole.

Compounds #8, 13 to 15, 17 to 19, and 21 to 25 were each synthesized with methyl N-methoxycarbonylindoleacetate as a key intermediate.

1-Methoxycarbonylindole-3-acetic Acid Methyl Ester

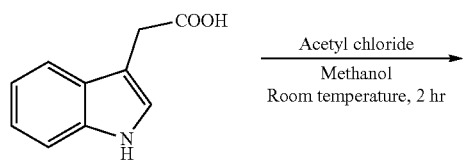

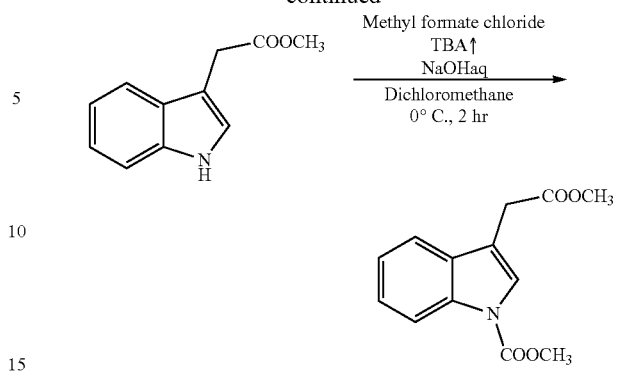

Indole-3-acetic Acid Methyl Ester

Indole-3-acetic acid (2.00 g, 11.42 mmol) was dissolved in methanol (40 ml). To this solution, acetyl chloride (0.5 ml, 6.688 mmol) was added dropwise, and the mixture was stirred at room temperature for 2 hours. After the reaction was confirmed by TLC to be complete, the reaction was terminated by the addition of a saturated aqueous solution of sodium bicarbonate, followed by extraction with ethyl acetate (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain indole-3-acetic acid methyl ester (2.14 g, yield: 99%): $^1$H NMR (400 MHz, CDCl$_3$): δ 8.13 (s, 1H), 6.97 (s, 1H), 7.59 (d, J=7.7 Hz, 1H), 7.23 (d, J=7.9 Hz, 1H), 7.10-7.19 (m, 2H), 3.67 (s, 3H), 3.76 (s, 2H); $^{13}$C NMR (100 MHz, CDCl$_3$): δ 172.3, 136.0, 127.1, 123.2, 122.0, 119.5, 118.6, 111.2, 108.0, 51.9, 31.0; IR (neat): 3410, 1730, 1458, 1435, 1337, 1164, 1095, 1011 cm$^{-1}$; EI-MS m/z 189 [M]$^+$.

1-Methoxycarbonyl-3-indoleacetic Acid Methyl Ester

Methyl indole-3-acetate (2.00 g, 10.57 mmol) was dissolved in dichloromethane (30 ml). To this solution, tetrabutylammonium iodide (TBAI, 30.0 mg, 0.081 mmol) and a 30% aqueous sodium hydroxide solution (24 ml) were added, and the mixture was cooled to 0° C. To the reaction solution, methyl formate chloride (1.96 g, 20.73 mmol) was added, and the mixture was stirred at 0° C. for 2 hours. After the reaction was confirmed by TLC to be complete, the reaction was terminated by the addition of 6 N hydrochloric acid. Water (50 ml) was added thereto, followed by extraction with chloroform (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain methyl N-methoxycarbonylindole-3-acetate (2.26 g, yield: 87%): $^1$H NMR (400 MHz, CDCl$_3$): δ 8.18 (d, J=7.0 Hz, 1H), 7.59 (s, 1H), 7.53 (d, J=7.7 Hz, 1H), 7.35 (t, J=7.5 Hz, 1H), 7.27 (t, J=7.4 Hz, 1H), 4.00 (s, 3H), 3.72 (s, 3H), 3.71 (s, 2H); $^{13}$C NMR (100 MHz, CDCl$_3$): δ 171.1, 151.1, 135.2, 129.9, 124.6, 123.8, 122.8, 118.9, 115.0, 113.8, 53.5, 51.9, 30.6; IR (neat): 1746, 1455, 1382, 1258, 1164, 1089, 1018 cm$^{-1}$; EI-MS: m/z 247 [M]$^+$.

Compounds #8 and 9 were each synthesized according to a method described in International Publication No. WO 2010/045451.

Synthesis of compound #8

2-(N-tert-Butoxycarbonyl-4-piperidinyl)ethanol

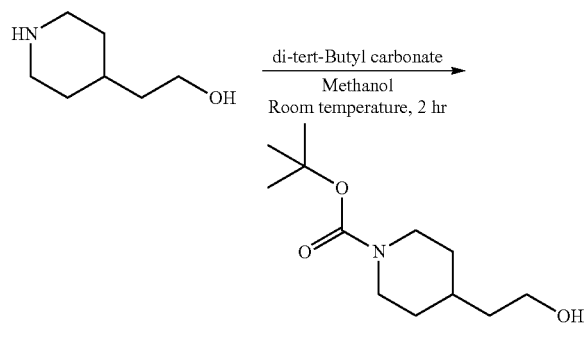

2-(4-Piperidinyl)ethanol (1.0 g, 7.7 mmol) was dissolved in methanol (50 ml). To this solution, di-tert-butyl carbonate (2.0 g, 9.3 mmol) was added, and the mixture was stirred at room temperature for 2 hours. After the reaction was confirmed by TLC to be complete, the solvent was distilled off under reduced pressure, and the residue was purified using silica gel column chromatography (hexane:acetone=9:1) to obtain N-tert-butoxycarbonyl-2-(4-piperidinyl)ethanol (1.68 g, yield: 95%).

Ethane 2-(N-tert-butoxycarbonyl-4-piperidinyl)-1-iodide

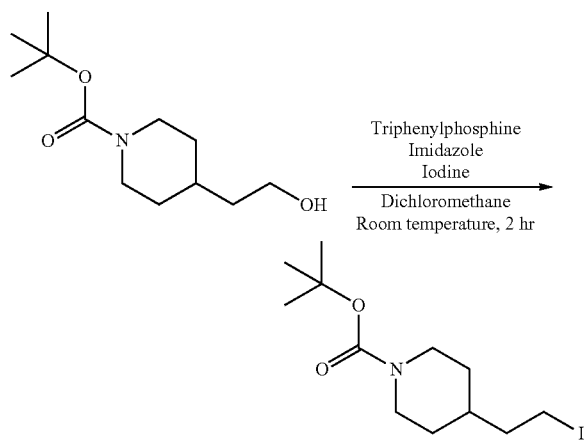

Triphenylphosphine (2.56 g, 9.760 mmol) and imidazole (0.66 g, 9.694 mmol) were dissolved in dichloromethane (15 ml), and the solution was stirred for 5 minutes. Then, iodine (2.47 g, 9.732 mmol) was added thereto, and the mixture was stirred for 10 minutes. A dichloromethane (4 ml) solution of N—N-tert-butoxycarbonyl-2-(4-piperidinyl) ethanol (1.49 g, 6.497 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain ethane N-tert-butoxycarbonyl-2-(4-piperidinyl)-1-iodide (2.13 g, yield: 96%).

α-[2-(N-tert-Butoxycarbonyl-4-piperidinyl)-1-ethyl]-1-methoxycarbonyl-3-indoleacetic Acid Methyl Ester

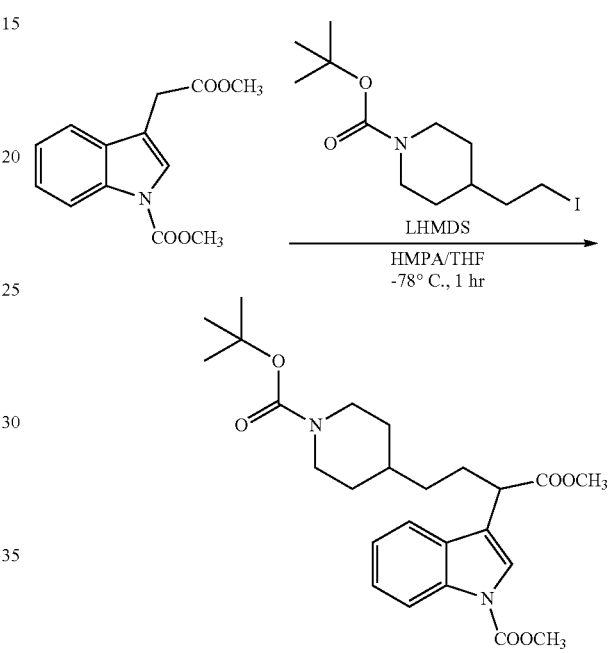

In a nitrogen atmosphere, 1-methoxycarbonyl-3-indoleacetic acid methyl ester (500 mg, 2.022 mmol) and hexamethylphosphoric triamide (HMPA, 1.81 g, 10.11 mmol) were dissolved in tetrahydrofuran (4 ml), and the solution was cooled to −78° C. A 1.5 M solution of lithium diisopropylamide (LDA) in cyclohexane (2.16 ml, 1.6 eq) was slowly added dropwise thereto, and the mixture was stirred at −78° C. for 0.5 hours. To this reaction solution, a tetrahydrofuran (2 ml) solution of ethane 2-(N-tert-butoxycarbonyl-4-piperidinyl)-1-iodide (686 mg, 2.022 mmol) was slowly added dropwise, and the mixture was stirred at −78° C. for 1 hour. After the reaction was confirmed by TLC to be complete, the temperature was adjusted to 0° C., and the reaction was terminated by the addition of water (15 ml), followed by extraction with ethyl acetate (15 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-2-(N-tert-butoxycarbonyl-4-piperidinyl)-ethyl-1-methoxycarbonyl-3-indoleacetic acid methyl ester (626 mg, yield: 68%): $^1$H NMR (400 MHz, CDCl$_3$): δ 8.19 (m, 1H), 7.61 (d, J=7.8 Hz, 1H), 7.56 (s, 1H), 7.35 (t, J=7.7 Hz, 1H), 7.25-7.30 (m, 1H), 3.79-4.15 (m, 5H), 3.77 (t, J=7.6 Hz, 1H), 3.68 (s, 3H), 2.65 (m, 2H), 2.05 (m, 2H), 1.65 (m, 2H), 1.25-1.50 (m, 12H), 1.05-1.19 (m, 2H); $^{13}$C NMR (100 MHz, CDCl$_3$): δ 173.9, 168.0, 154.8, 135.4, 129.3, 124.8, 123.1, 122.9, 119.2, 119.2, 115.2, 79.1, 53.7, 53.0, 52.1, 48.9, 43.7, 42.7, 35.9, 34.3, 32.0, 29.5, 28.4; FAB-MS: m/z 459 [M+H]$^+$.

α-[2-(1-Acetyl-4-piperidinyl)-ethyl]-1-methoxycarbonyl-3-indoleacetic Acid Methyl Ester

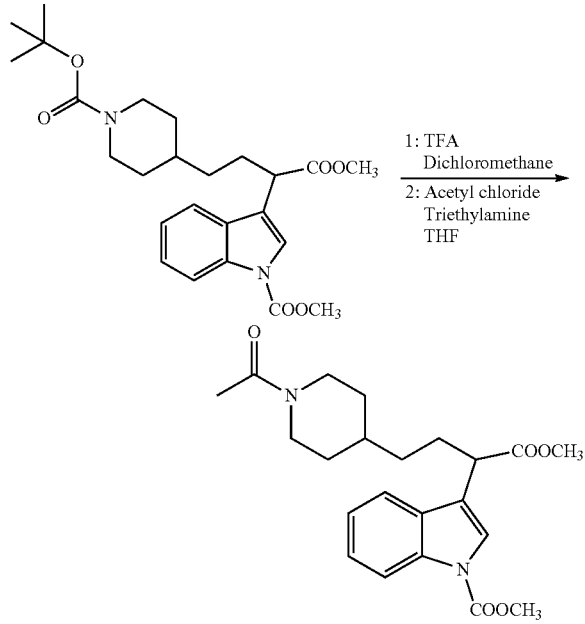

α-[2-(N-tert-Butoxycarbonyl-4-piperidinyl)-1-ethyl]-1-methoxycarbonyl-3-indoleacetic acid methyl ester (100 mg, 0.218 mmol) was dissolved in dichloromethane (2 ml). To the solution, trifluoroacetic acid (1.0 ml, 13.07 mmol) was added, and the mixture was stirred at room temperature for 5 minutes. The reaction solution was added dropwise to a 10% aqueous sodium carbonate solution (10 mL) to terminate the reaction. This solution was subjected to extraction with ethyl acetate (10 mL) three times. The organic layer was washed twice with saturated saline (10 mL) and dehydrated over anhydrous sodium sulfate. The solvent was distilled off under reduced pressure to obtain α-[2-(4-piperidinyl)-ethyl]-1-methoxycarbonyl-3-indoleacetic acid methyl ester (74.1 mg). This compound (74.1 mg, 0.207 mmol) was dissolved in tetrahydrofuran (3 mL). To the solution, triethylamine (0.2 mL) and acetyl chloride (10 mg) were added, and the mixture was stirred at room temperature for 1.5 hours. The reaction was terminated by the addition of a saturated aqueous solution of ammonium chloride (10 mL), followed by extraction with ethyl acetate (10 mL) three times. The organic layer was washed twice with saturated saline (10 mL) and dehydrated over anhydrous sodium sulfate. The solvent was distilled off under reduced pressure, and then, the residue was purified using silica gel column chromatography (chloroform:acetone=9:1) to obtain α-[2-(1-acetyl-4-piperidinyl)-ethyl]-1-methoxycarbonyl-3-indoleacetic acid methyl ester (53.9 mg, yield: 65%): $^1$H NMR (400 MHz, CDCl$_3$): δ 8.18 (d, J=6.7 Hz, 1H), 7.61 (d, J=7.8 Hz, 1H), 7.56 (s, 1H), 7.35 (t, J=8.4 Hz, 1H), 7.25-7.28 (m, 1H), 4.57 (d, J=12.8 Hz, 1H), 4.03 (s, 3H), 3.73-3.79 (m, 2H), 3.68 (s, 3H), 2.99 (t, J=12.9 Hz, 1H), 2.50 (t, J=12.6 Hz, 1H), 1.91-2.19 (m, 5H), 1.73 (t, J=10.4 Hz, 2H), 1.49 (m, 1H), 1.26-1.32 (m, 2H), 1.05-1.12 (m, 2H); $^{13}$C NMR (100 MHz, CDCl$_3$): δ 173.8, 168.7, 151.2, 135.4, 129.3, 124.8, 122.9, 119.2, 119.1, 115.2, 53.7, 52.1, 46.6, 42.7, 41.7, 35.9, 34.2, 32.5, 31.6, 29.2, 21.4; FAB-MS: m/z 401 [M+H]$^+$.

α-2-(1-Acetyl-4-piperidinyl)-ethyl-3-indoleacetic Acid (Compound #8)

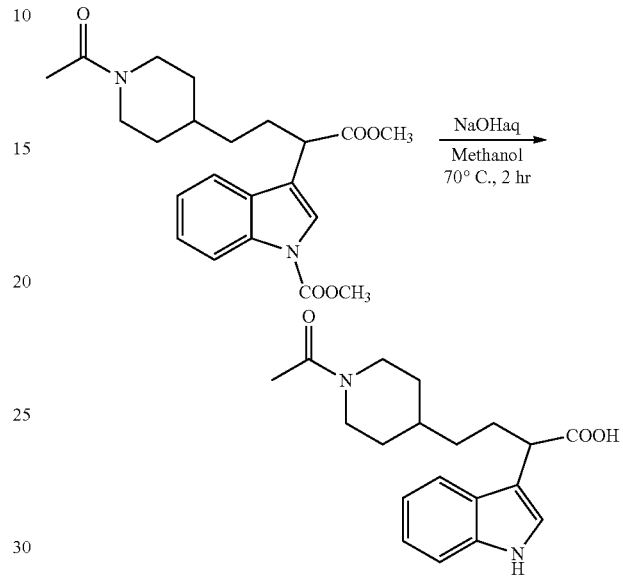

α-2-(1-Acetyl-4-piperidinyl)-ethyl-N-methoxycarbonyl-3-indoleacetic acid methyl ester (48.0 mg, 0.120 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:acetone=3:2) to obtain α-2-(1-acetyl-4-piperidinyl)-ethyl-3-indoleacetic acid (compound #8) (25.5 mg, yield: 65%: $^1$H NMR (400 MHz, CDCl$_3$): δ 8.54 (s, 1H), 7.67 (d, J=7.9 Hz, 1H), 7.31 (d, J=8.0 Hz, 1H), 7.16 (t, J=7.7 Hz, 1H), 7.07-7.11 (m, 2H), 4.48 (d, J=12.7 Hz, 1H), 3.81 (t, J=7.5 Hz, 1H), 3.66 (d, J=13.2 Hz, 1H), 2.89 (t, J=12.5 Hz, 1H), 2.43 (t, J=12.6 Hz, 1H), 1.86-2.17 (m, 5H), 1.62 (t, J=16.5 Hz, 2H), 1.41 (m, 1H), 1.22-1.28 (m, 2H), 0.93-1.01 (m, 2H); $^{13}$C NMR (100 MHz, CDCl$_3$): δ 178.8, 169.3, 136.2, 126.5, 122.3, 122.0, 119.5, 119.1, 113.3, 111.4, 46.7, 43.1, 42.0, 35.7, 34.2, 32.5, 31.6, 29.7, 21.3; IR (neat): 3410, 1699, 1454, 1271 cm$^{-1}$; FAB-MS: m/z 329 [M+H]$^+$.

α-2-(1-Acetyl-4-piperidinyl)-methyl-3-indoleacetic acid (compound #9) was synthesized by the same approach as in compound #8 using N-tert-butoxycarbonyl-4-piperidinyl-methanol instead of 2-(N-tert-butoxycarbonyl-4-piperidinyl)ethanol.

Synthesis of Compound #10

α-4-Aminobutyl-N-methoxycarbonyl-3-indoleacetic Acid Methyl Ester

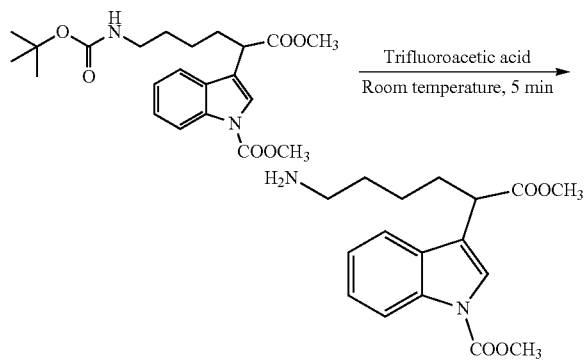

To α-(N-tert-butoxycarbonyl-4-amino-1-butyl)-1-methoxycarbonyl-3-indoleacetic acid methyl ester (150 mg, 0.358 mmol), trifluoroacetic acid (0.4 ml, 5.227 mmol) was added, and the mixture was stirred at room temperature. After 5 minutes, the reaction solution was added dropwise to an aqueous sodium bicarbonate solution to terminate the reaction. Water (5 ml) was added thereto, followed by extraction with ethyl acetate (5 ml) three times. The organic layer was washed twice with saturated saline and dehydrated over anhydrous sodium sulfate. The solvent was distilled off under reduced pressure to obtain α-4-aminobutyl-N-methoxycarbonyl-3-indoleacetic acid methyl ester.

α-[N-(1-Acetylpyrrolidine-2-carbonyl)-4-aminobutyl]-N-methoxycarbonyl-3-indoleacetic Acid Methyl Ester

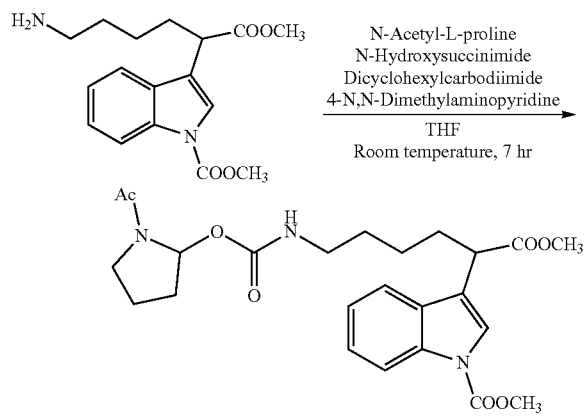

α-4-Aminobutyl-N-methoxycarbonyl-3-indoleacetic acid methyl ester (150 mg, 0.493 mmol) was dissolved in tetrahydrofuran (3 ml). To this solution, N-acetyl-L-proline (116 mg, 0.738 mmol), N-hydroxysuccinimide (85.0 mg, 0.739 mmol), dicyclohexylcarbodiimide (152 mg, 0.737 mmol), and 4-N,N-dimethylaminopyridine (72.0 mg, 0.589 mmol) were added, and the mixture was stirred at room temperature for 7 hours. The reaction was terminated with a saturated aqueous solution of ammonium chloride, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:acetone=7:3) to obtain α-[N-(1-acetylpyrrolidine-2-carbonyl)-4-aminobutyl]-N-methoxycarbonyl-3-indoleacetic acid methyl ester (107 mg, yield: 49%): $^1$H NMR (400 MHz, CDCl$_3$): δ 8.17 (d, J=7.1 Hz, 1H), 7.61 (d, J=7.7 Hz, 1H), 7.55 (s, 1H), 7.33 (t, J=7.8 Hz, 1H), 7.25 (t, J=7.4 Hz, 1H), 7.18 (s, 1H), 4.50 (d, J=7.3 Hz, 1H), 4.02 (s, 3H), 3.80 (t, J=7.6 Hz, 1H), 3.67 (s, 3H), 3.36-3.58 (m, 2H), 3.10-3.26 (m, 2H), 1.76-2.40 (m, 9H), 1.49-1.56 (m, 2H), 1.33-1.38 (m, 2H); $^{13}$C NMR (100 MHz, CDCl$_3$): δ 173.8, 171.0, 170.8, 151.1, 135.3, 129.2, 124.6, 122.9, 122.8, 119.2, 119.1, 115.0, 59.4, 53.6, 51.9, 48.1, 42.3, 38.9, 31.5, 29.0, 27.2, 24.8, 24.7, 22.3; FAB-MS: m/z 458 [M+H]$^+$.

α-[N-(1-Acetylpyrrolidine-2-carbonyl)-4-aminobutyl]-3-indoleacetic Acid (Compound #10)

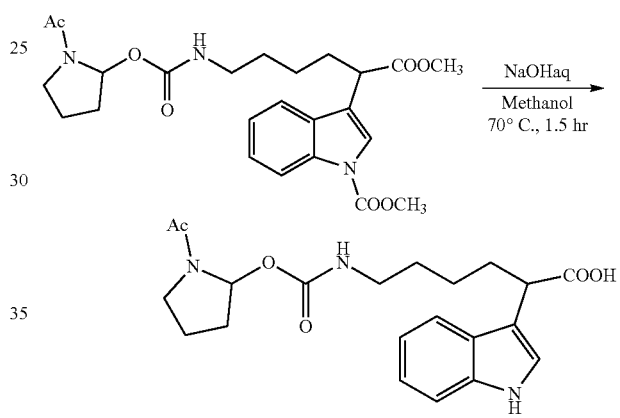

α-[N-(1-Acetylpyrrolidine-2-carbonyl)-4-aminobutyl]-N-methoxycarbonyl-3-indoleacetic acid methyl ester (80.0 mg, 0.175 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-[N-(1-acetylpyrrolidine-2-carbonyl)-4-aminobutyl]-3-indoleacetic acid (compound #10) (63.6 mg, yield: 94%): $^1$H NMR (400 MHz, acetone-d$_6$): δ 10.21 (s, 1H), 8.03 (s, 1H), 7.70 (d, J=7.8 Hz, 1H), 7.38 (d, J=8.0 Hz, 1H), 7.27 (s, 1H), 7.09 (t, J=7.3 Hz, 1H), 7.01 (t, J=7.6 Hz, 1H), 4.35 (d, J=7.2 Hz, 1H), 3.85 (t, J=7.6 Hz, 1H), 3.53 (m, 1H), 3.40-3.46 (m, 1H), 3.23 (m, 1H), 3.10-3.17 (m, 1H), 1.85-2.14 (m, 9H), 1.36-1.50 (m, 4H); $^{13}$C NMR (100 MHz, acetone-d$_6$): δ 175.8, 172.1, 170.3, 137.3, 127.5, 123.3, 121.9, 119.7, 119.3, 114.1, 112.0, 60.5, 48.3, 43.3, 39.2, 32.9, 32.5, 25.4, 25.1, 22.2; IR (Neat): 3300, 1634, 1456, 1245 cm$^{-1}$; FAB-MS: m/z 386 [M+H]$^+$.

Synthesis of Compound #11

α-[2-(2-Aminoethoxy)-ethyl]-N-methoxycarbonyl-3-indoleacetic Acid Methyl Ester

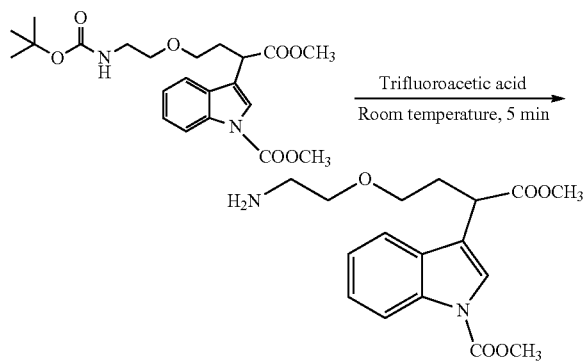

To α-[N-tert-butoxycarbonyl-(2-aminoethoxyethyl)]-1-methoxycarbonyl-3-indoleacetic acid methyl ester (140 mg, 0.322 mmol), trifluoroacetic acid (0.3 ml, 3.920 mmol) was added, and the mixture was stirred at room temperature. After 5 minutes, the reaction solution was added dropwise to an aqueous sodium bicarbonate solution to terminate the reaction. Water (5 ml) was added thereto, followed by extraction with ethyl acetate (5 ml) three times. The organic layer was washed twice with saturated saline and dehydrated over anhydrous sodium sulfate. The solvent was distilled off under reduced pressure to obtain α-[2-(2-aminoethoxy)-ethyl]-N-methoxycarbonyl-3-indoleacetic acid methyl ester (80.0 mg, yield: 74%).

α-{N-(1-Acetylpyrrolidine-2-carbonyl)-[2-(2-aminoethoxy)-ethyl]}-N-methoxycarbonyl-3-indoleacetic Acid Methyl Ester

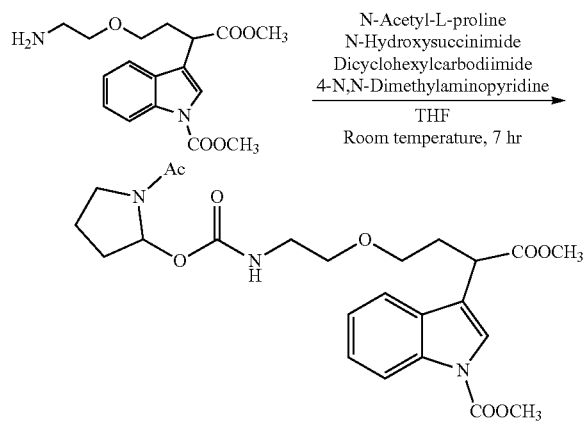

α-[2-(2-Aminoethoxy)-ethyl]-N-methoxycarbonyl-3-indoleacetic acid methyl ester (80.0 mg, 0.239 mmol) was dissolved in tetrahydrofuran (3 ml). To this solution, N-acetyl-L-proline (56.4 mg, 0.359 mmol), N-hydroxysuccinimide (41.2 mg, 0.358 mmol), dicyclohexylcarbodiimide (74.0 mg, 0.359 mmol), and 4-N,N-dimethylaminopyridine (35.0 mg, 0.286 mmol) were added, and the mixture was stirred at room temperature for 7 hours. The reaction was terminated with a saturated aqueous solution of ammonium chloride, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:acetone=7:3) to obtain α-[N-(1-acetylpyrrolidine-2-carbonyl)-4-aminobutyl]-N-methoxycarbonyl-3-indoleacetic acid methyl ester (76.1 mg, yield: 67%): $^1$H NMR (400 MHz, CDCl$_3$): δ 8.18 (d, J=7.1 Hz, 1H), 7.57-7.66 (m, 2H), 7.35 (t, J=7.7 Hz, 1H), 7.25-7.28 (m, 2H), 4.56 (t, J=8.3 Hz, 1H), 4.09 (t, J=7.6 Hz, 1H), 4.03 (s, 3H), 3.68 (s, 3H), 3.59 (t, J=9.0 Hz, 1H), 3.32-3.52 (m, 7H), 2.36-2.48 (m, 2H), 1.84-2.18 (m, 7H), 1.49-1.56 (m, 2H), 1.33-1.38 (m, 2H); $^{13}$C NMR (100 MHz, CDCl$_3$): δ 174.2, 171.5, 170.8, 151.1, 135.5, 129.3, 124.8, 123.1, 123.0, 119.4, 118.9, 115.2, 69.4, 68.4, 59.2, 53.8, 52.2, 48.2, 39.5, 39.2, 32.2, 27.8, 25.0, 22.5; FAB-MS: m/z 474 [M+H]$^+$.

α-[N-(1-Acetylpyrrolidine-2-carbonyl)-4-aminobutyl]-3-indoleacetic Acid (Compound #11)

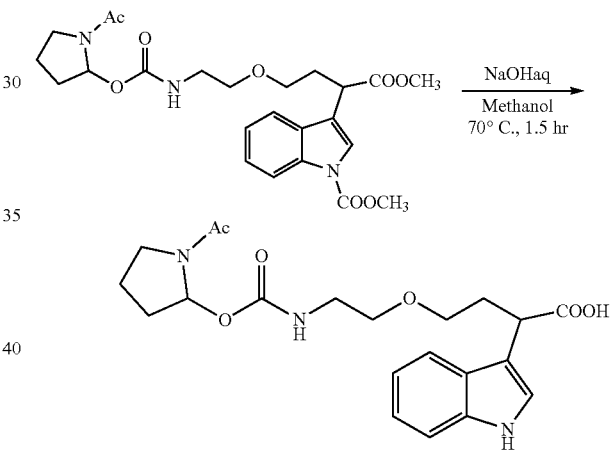

α-[N-(1-Acetylpyrrolidine-2-carbonyl)-4-aminobutyl]-N-methoxycarbonyl-3-indoleacetic acid methyl ester (60.0 mg, 0.127 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-[N-(1-acetylpyrrolidine-2-carbonyl)-4-aminobutyl]-3-indoleacetic acid (compound #11) (36.6 mg, yield: 72%): $^1$H NMR (400 MHz, acetone-d$_6$): δ 8.48 (d, J=13.4 Hz, 1H), 7.70 (d, J=7.9 Hz, 1H), 7.34 (d, J=8.1 Hz, 1H), 7.09-7.21 (m, 3H), 4.67 (t, J=8.3 Hz, 1H), 4.40-4.11 (m, 1H), 3.18-3.76 (m, 8H), 2.46-2.67 (m, 4H), 1.86-2.22 (m, 7H); $^{13}$C NMR (100 MHz, acetone-d$_6$): δ 178.0, 171.6, 171.2, 136.1, 126.5, 122.3, 122.0, 119.4, 118.9, 113.7, 111.2, 69.3, 68.6, 60.0, 48.5, 41.2, 39.9, 33.7, 29.1, 24.8, 22.3; IR (Neat): 3317, 1634, 1456, 1247, 1119 cm$^{-1}$; FAB-MS: m/z 402 [M+H]$^+$.

Synthesis of Compound #12

α-(N-tert-Butoxycarbonyl-6-amino-1-hexyl)-α-(1-naphthyl)-acetic Acid Methyl Ester

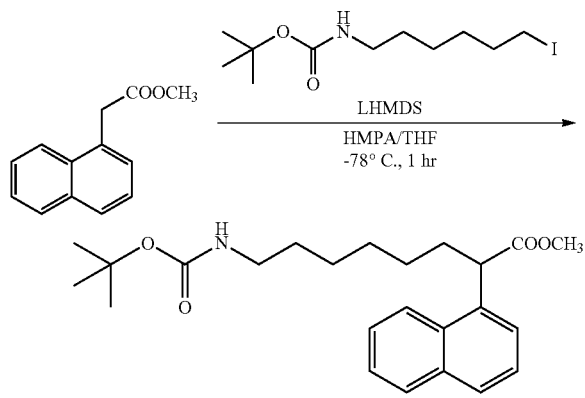

α-(1-Naphthyl)-acetic acid methyl ester (150 mg, 0.75 mmol) was dissolved in tetrahydrofuran. To the solution, hexamethylphosphoramide (HMPA, 671 mg, 3.75 mmol) was added, and the mixture was cooled to −78° C. To this solution, lithium diisopropylamide (1.5 M solution in cyclohexane, 0.75 ml, 1 mmol) was added dropwise, and the mixture was stirred at −78° C. for 30 minutes. Then, a tetrahydrofuran solution (2 mL) of N-tert-butoxycarbonyl-6-amino-1-iodohexane (270 mg, 0.82 mmol) was added dropwise thereto, and the mixture was stirred at −78° C. for 1 hour. The temperature of the reaction solution was raised to 0° C. over 15 minutes, and then, water (50 mL) was added to the solution, followed by extraction with ethyl acetate (50 mL) twice. The organic layer was washed with a saturated ammonium chloride solution (20 mL) and subsequently saline (20 mL) and then dehydrated over sodium sulfate to dryness under reduced pressure. The reaction product was purified using silica gel column chromatography (hexane:ethyl acetate=8:2) to obtain α-(N-tert-butoxycarbonyl-6-amino-1-hexyl)-α-(1-naphthyl)-acetic acid methyl ester (271 mg, yield: 91%): $^1$H NMR (400 MHz, CDCl$_3$): δ 8.11 (d, J=8.5 Hz, 1H), 7.83 (d, J=8.0 Hz, 1H), 7.74 (d, J=8.1 Hz, 1H), 7.40-7.54 (m, 4H), 4.71 (s, 1H), 4.36 (t, J=7.8 Hz, 1H), 3.61 (s, 3H), 3.04 (m, 2H), 2.07 (m, 2H), 1.24-1.48 (m, 17H); $^{13}$C NMR (100 MHz, CDCl$_3$): δ 174.7, 155.9, 135.3, 133.8, 131.3, 128.8, 127.5, 126.1, 125.4, 125.3, 124.6, 122.8, 78.7, 51.8, 46.5, 40.3, 32.9, 29.7, 28.9, 28.2, 27.6, 26.3; FAB-MS: m/z 400 [M+H]$^+$.

α-(N-tert-Butoxycarbonyl-6-amino-1-hexyl)-α-(1-naphthyl)-acetic Acid (Compound #12)

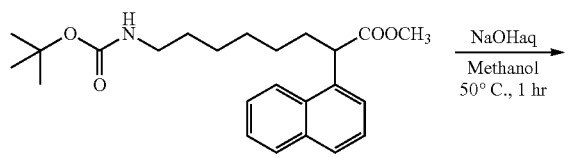

α-(N-tert-Butoxycarbonyl-6-amino-1-hexyl)-α-(1-naphthyl)-acetic acid methyl ester (100 mg, 0.25 mmol) was dissolved in a mixed solution of methanol and an aqueous sodium hydroxide solution (2 N aqueous sodium hydroxide solution:methanol=1:4, 5 mL), and the solution was heated at 50° C. for 1 hour. The reaction solution was pH-adjusted to 3.5 with 6 N hydrochloric acid, and methanol was removed by distillation under reduced pressure. To this solution, water (15 mL) was added, followed by extraction with ethyl acetate (50 mL) twice. The organic layer was washed with a saturated ammonium chloride solution (20 mL) and subsequently saline (20 mL) and then dehydrated over sodium sulfate to dryness under reduced pressure. The reaction product was purified using silica gel column chromatography (chloroform:methanol=95:5) to obtain α-(N-tert-butoxycarbonyl-6-amino-1-hexyl)-α-(1-naphthyl)-acetic acid (compound #12) (90 mg, yield: 93%): $^1$H NMR (400 MHz, CDCl$_3$): δ 8.13 (d, J=8.4 Hz, 1H), 7.84 (d, J=7.9 Hz, 1H), 7.75 (d, J=8.1 Hz, 1H), 7.41-7.53 (m, 4H), 4.56 (s, 1H), 4.35 (t, J=7.4 Hz, 1H), 3.03 (m, 2H), 2.05 (m, 2H), 1.22-1.46 (m, 17H); $^{13}$C NMR (100 MHz, CDCl$_3$): δ 179.0, 156.0, 135.1, 133.9, 131.6, 128.9, 127.7, 126.2, 125.5, 125.4, 124.9, 123.1, 79.0, 46.6, 40.4, 32.7, 29.8, 29.0, 28.3, 27.7, 26.4; IR (neat): 3417, 1705, 1457, 1268, 1099 cm$^{-1}$; FAB-MS: m/z 386 [M+H]$^+$.

Synthesis of Compound #13

N-tert-Butoxycarbonyl-6-amino-1-hexanol

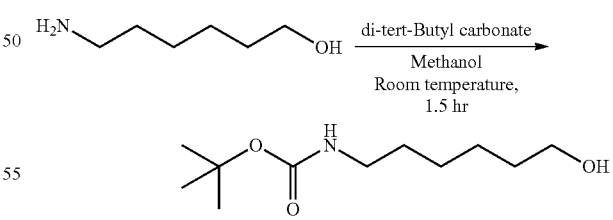

6-Amino-1-hexanol (1.0 g, 8.533 mmol) was dissolved in methanol (10 ml). To this solution, di-tert-butyl carbonate (1.86 g, 8.522 mmol) was added, and the mixture was stirred at room temperature for 1.5 hours. After the reaction was confirmed by TLC to be complete, the solvent was distilled off under reduced pressure, and the residue was purified using silica gel column chromatography (hexane:acetone=9:1) to obtain N-tert-butoxycarbonyl-6-aminohexanol (1.80 g, yield: 97%).

N-tert-Butoxycarbonyl-6-amino-1-iodohexane

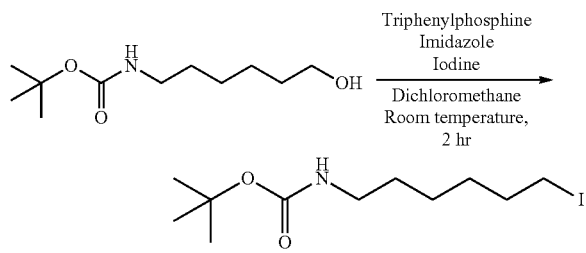

Triphenylphosphine (2.35 g, 8.96 mmol) and imidazole (0.61 g, 8.96 mmol) were dissolved in dichloromethane (15 ml), and the solution was stirred for 5 minutes. Then, iodine (2.28 g, 8.98 mmol) was added thereto, and the mixture was stirred for 10 minutes. A dichloromethane (4 ml) solution of N-tert-butoxycarbonyl-6-aminohexanol (1.3 g, 5.98 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain N-tert-butoxycarbonyl-6-amino-1-iodohexane (1.67 g, yield: 86%).

α-Methyl-1-methoxycarbonyl-3-indoleacetic acid methyl ester was synthesized according to a method described in Katayama M, Kato Y, Marumo S. "Synthesis, absolute configuration and biological activity of both enantiomers of 2-(5,6-dichloro-3-indolyl)propionic acid: new dichloroindole auxins" Bioscience, Biotechnology, and Biochemistry, 65 (2), 270-276; 2001.

α-(N-tert-Butoxycarbonyl-6-amino-1-hexyl)-α-methyl-1-methoxycarbonyl-3-indoleacetic Acid Methyl Ester

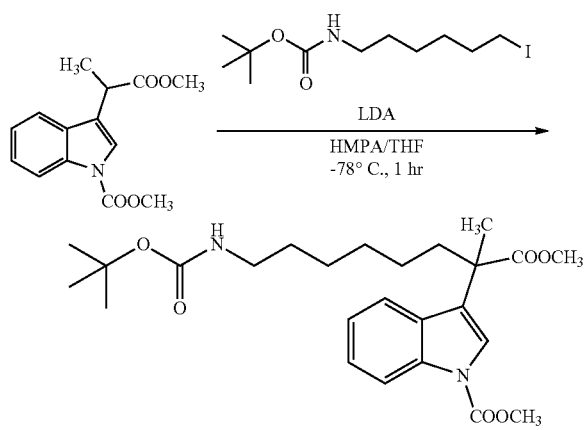

In a nitrogen atmosphere, α-methyl-1-methoxycarbonyl-3-indoleacetic acid methyl ester (83.8 mg, 0.321 mmol) was dissolved in tetrahydrofuran (2 ml), and the solution was cooled to −78° C. This solution was slowly added dropwise to a 1.0 M solution of lithium bistrimethylsilylamide (LHMDS) in tetrahydrofuran (0.69 ml, 1.5 eq), and the mixture was stirred at −78° C. for 0.5 hours. To this reaction solution, a tetrahydrofuran (1 ml) solution of N-tert-butoxycarbonyl-6-amino-1-iodohexane (105 mg, 0.321 mmol) was slowly added dropwise, and the mixture was stirred at −78° C. for 2 hours. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-(N-tert-butoxycarbonyl-6-amino-1-hexyl)-α-methyl-1-methoxycarbonyl-3-indoleacetic acid methyl ester (68.6 mg, yield: 46%): $^1$H NMR (400 MHz, CDCl$_3$): δ 8.19 (d, J=6.3 Hz, 1H), 7.52 (d, J=7.9 Hz, 1H), 7.48 (s, 1H), 7.32 (t, J=7.5 Hz, 1H), 7.21 (t, J=7.5 Hz, 1H), 4.54 (s, 1H), 4.03 (s, 3H), 3.62 (s, 3H), 3.06 (m, 2H), 2.04-2.12 (m, 2H), 1.61 (s, 3H), 1.17-1.43 (m, 17H); $^{13}$C NMR (100 MHz, CDCl$_3$): δ 176.3, 155.9, 151.3, 135.8, 128.6, 124.9, 124.5, 122.8, 122.0, 120.0, 115.2, 78.9, 53.7, 52.1, 45.5, 40.4, 37.2, 29.9, 29.5, 28.3, 26.5, 24.2, 22.5; FAB-MS: m/z 460 [M]$^+$.

α-(N-tert-Butoxycarbonyl-6-amino-1-hexyl)-α-methyl-3-indoleacetic Acid (Compound #13)

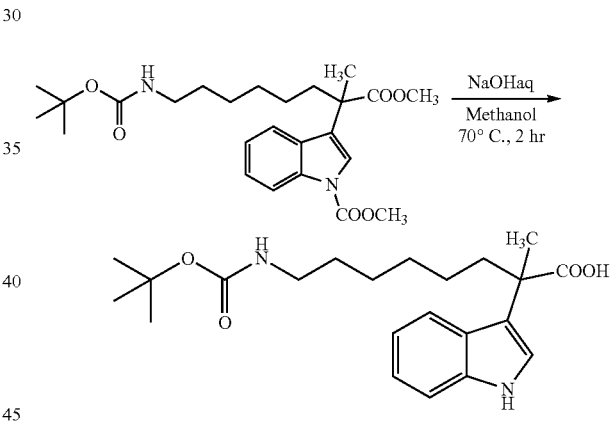

α-(N-tert-Butoxycarbonyl-6-amino-1-hexyl), α-methyl-1-methoxycarbonyl-3-indoleacetic acid methyl ester (60.0 mg, 0.130 mmol) was dissolved in methanol (4.6 ml). To the solution, water (0.4 ml) and potassium hydroxide (1.68 g, 30 mmol) were added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (benzene:acetone=85:15) to obtain α-(N-tert-butoxycarbonyl-6-amino-1-hexyl)-α-methyl-3-indoleacetic acid (compound #13) (40.0 mg, yield: 79%): $^1$H NMR (400 MHz, CDCl$_3$): δ 8.26 (s, 1H), 7.71 (d, J=8.0 Hz, 1H), 7.33 (d, J=8.0 Hz, 1H), 7.16 (t, J=7.4 Hz, 1H), 7.06 (t, J=7.3 Hz, 1H), 7.04 (s, 1H), 4.52 (s, 1H), 3.03 (m, 2H), 2.08-2.17 (m, 2H), 1.63 (s, 3H), 1.23-1.48 (m, 17H); $^{13}$C NMR (100 MHz, CDCl$_3$): δ 181.7, 156.1, 136.7, 125.5, 121.4, 120.4, 119.2, 118.8, 111.3, 79.1, 45.7, 40.5, 37.5, 29.7, 28.5, 26.5, 24.2, 22.6; IR (neat): 3415, 3339, 1699, 1519, 1460, 1369, 1249, 1170 cm$^{-1}$; FAB-MS: m/z 389 [M+H]$^+$.

Synthesis of Compound #14

2-(N-tert-Butoxycarbonyl-2-aminoethoxy)-ethanol

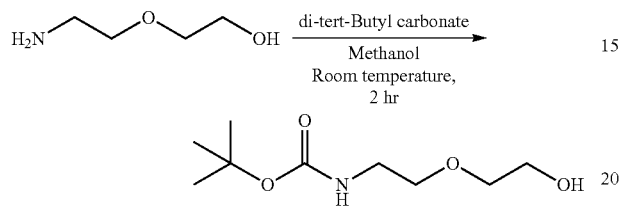

2-(2-Aminoethoxy)-ethanol (1.0 g, 9.511 mmol) was dissolved in methanol (10 ml). To this solution, di-tert-butyl carbonate (2.07 g, 9.485 mmol) was added, and the mixture was stirred at room temperature for 2 hours. After the reaction was confirmed by TLC to be complete, the solvent was distilled off under reduced pressure, and the residue was purified using silica gel column chromatography (hexane:acetone=3:2) to obtain 2-(N-tert-butoxycarbonyl-2-aminoethoxy)-ethanol (1.78 g, yield: 91%)

2-(N-tert-Butoxycarbonyl-2-aminoethoxy)-1-iodoethane

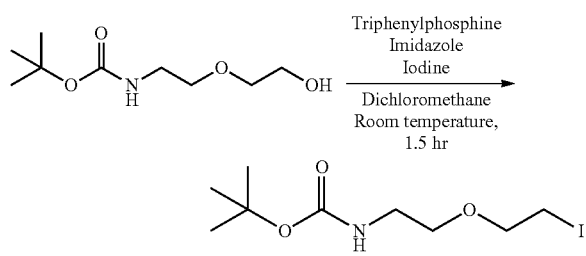

Triphenylphosphine (2.87 g, 10.94 mmol) and imidazole (0.75 g, 11.02 mmol) were dissolved in dichloromethane (15 ml), and the solution was stirred for 5 minutes. Then, iodine (2.78 g, 10.95 mmol) was added thereto, and the mixture was stirred for 10 minutes. A dichloromethane (4 ml) solution of 2-(N-tert-butoxycarbonyl-2-aminoethoxy)-ethanol (1.5 g, 7.308 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=85:15) to obtain 2-(N-tert-butoxycarbonyl-2-aminoethoxy)-1-iodoethane (2.19 g, yield: 95%).

α-[2-(N-tert-Butoxycarbonyl-2-aminoethoxy)-1-ethyl]-1-methoxycarbonyl-3-indoleacetic Acid Methyl Ester

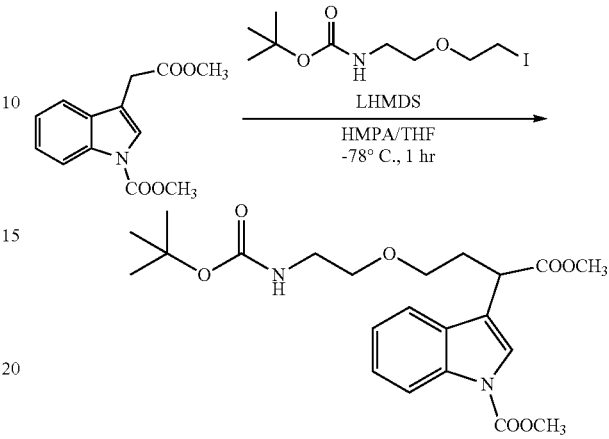

In a nitrogen atmosphere, 1-methoxycarbonyl-3-indoleacetic acid methyl ester (500 mg, 2.022 mmol) and hexamethylphosphoric triamide (HMPA, 1.81 g, 10.11 mmol) were dissolved in tetrahydrofuran (4 ml), and the solution was cooled to −78° C. A 1.5 M solution of lithium diisopropylamide (LDA) in cyclohexane (2.02 ml, 1.5 eq) was slowly added dropwise thereto, and the mixture was stirred at −78° C. for 0.5 hours. To this reaction solution, a tetrahydrofuran (2 ml) solution of 2-(N-tert-butoxycarbonyl-2-aminoethoxy)-1-iodoethane (637 mg, 2.022 mmol) was slowly added dropwise, and the mixture was stirred at −78° C. for 1 hour. After the reaction was confirmed by TLC to be complete, the temperature was adjusted to 0° C., and the reaction was terminated by the addition of water (15 ml), followed by extraction with ethyl acetate (15 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-[2-(N-tert-butoxycarbonyl-2-aminoethoxy)-1-ethyl]-1-methoxycarbonyl-3-indoleacetic acid methyl ester (645 mg, yield: 79%): $^1$H NMR (400 MHz, CDCl$_3$): δ 8.18 (d, J=7.0 Hz, 1H), 7.63 (d, J=7.7 Hz, 1H), 7.57 (s, 1H), 7.34 (t, J=7.7 Hz, 1H), 7.26 (t, J=7.3 Hz, 1H), 4.98 (s, 1H), 4.02-4.06 (m, 4H), 3.69 (s, 3H), 3.43-3.51 (m, 4H), 3.30 (m, 2H), 2.29 (m, 2H), 1.45 (s, 3H); $^{13}$C NMR (100 MHz, CDCl$_3$): δ 173.8, 155.9, 151.2, 135.4, 124.8, 123.1, 122.9, 119.2, 118.8, 115.2, 79.1, 69.8, 68.3, 52.7, 52.1, 40.3, 39.3, 32.2, 28.3; FAB-MS: m/z 435 [M+H]$^+$.

α-[2-(N-tert-Butoxycarbonyl-2-aminoethoxy)-1-ethyl]-3-indoleacetic Acid (Compound #14)

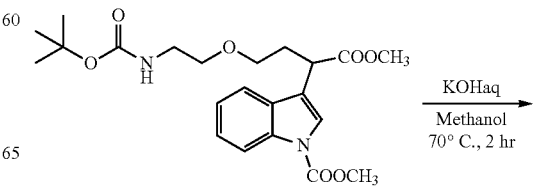

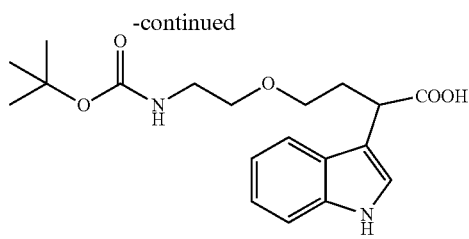

α-[2-(N-tert-Butoxycarbonyl-2-aminoethoxy)-1-ethyl]-1-methoxycarbonyl-3-indoleacetic Acid methyl ester (80.0 mg, 0.184 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-[2-(N-tert-butoxycarbonyl-2-aminoethoxy)-1-ethyl]-3-indoleacetic acid (compound #14) (70.2 mg, yield: 87%): $^1$H NMR (400 MHz, CDCl$_3$): δ 8.40 (s, 1H), 7.67 (d, J=7.9 Hz, 1H), 7.29 (d, J=8.0 Hz, 1H), 7.15 (t, J=7.8 Hz, 1H), 7.08 (t, J=7.3 Hz, 1H), 7.04 (s, 1H), 5.03 (s, 1H), 4.04 (t, J=7.1 Hz, 1H), 3.30-3.46 (m, 4H), 3.23 (m, 2H), 2.26 (m, 2H), 1.44 (s, 9H); $^{13}$C NMR (100 MHz, CDCl$_3$): δ 179.2, 156.2, 136.2, 126.4, 122.6, 122.1, 119.5, 119.1, 112.6, 111.3, 79.4, 69.7, 68.5, 40.3, 39.7, 32.3, 28.4; IR (neat): 3406, 3332, 1699, 1520, 1458, 1367, 1252, 1169, 1119 cm$^{-1}$; FAB-MS: m/z 385 [M+Na]$^+$.

Synthesis of compound #15

N-tert-Butoxycarbonyl-4-amino-1-butanol

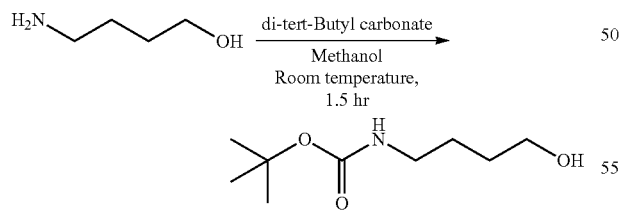

4-Amino-1-butanol (1.0 g, 11.22 mmol) was dissolved in methanol (10 ml). To this solution, di-tert-butyl carbonate (2.53 g, 11.58 mmol) was added, and the mixture was stirred at room temperature for 1.5 hours. After the reaction was confirmed by TLC to be complete, the solvent was distilled off under reduced pressure, and the residue was purified using silica gel column chromatography (hexane:acetone=9:1) to obtain N-tert-butoxycarbonyl-4-amino-1-butanol (1.88 g, yield: 89%).

N-tert-Butoxycarbonyl-4-amino-1-iodobutane

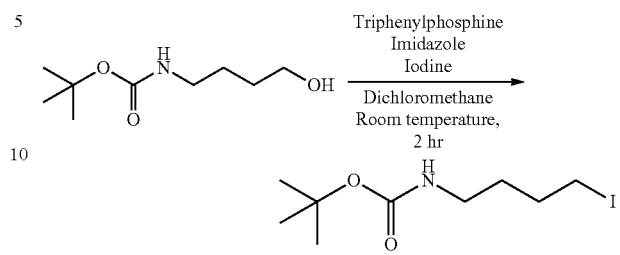

Triphenylphosphine (3.3 g, 12.58 mmol) and imidazole (0.86 g, 12.63 mmol) were dissolved in dichloromethane (15 ml), and the solution was stirred at 5 minutes. Then, iodine (3.2 g, 12.61 mmol) was added thereto, and the mixture was stirred for 10 minutes. A dichloromethane (4 ml) solution of N-tert-butoxycarbonyl-4-amino-1-butanol (1.6 g, 8.454 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain N-tert-butoxycarbonyl-4-amino-1-iodobutane (1.83 g, yield: 72%).

α-(N-tert-Butoxycarbonyl-4-amino-1-butyl)-1-methoxycarbonyl-3-indoleacetic Acid Methyl Ester

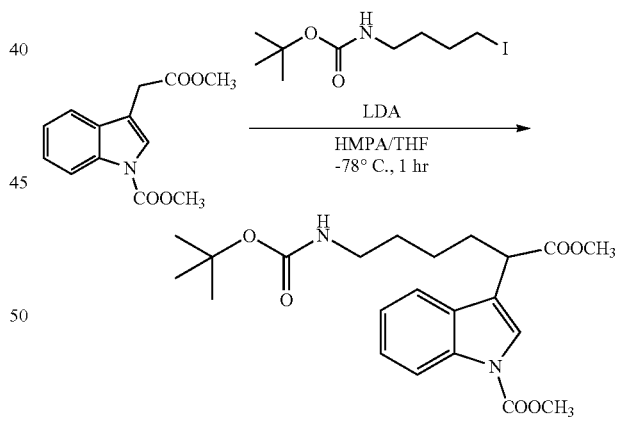

In a nitrogen atmosphere, 1-methoxycarbonyl-3-indoleacetic acid methyl ester (400 mg, 1.618 mmol) and hexamethylphosphoric triamide (HMPA, 1.45 g, 8.086 mmol) were dissolved in tetrahydrofuran (4 ml), and the solution was cooled to −78° C. A 1.5 M solution of lithium diisopropylamide (LDA) in cyclohexane (1.62 ml, 1.5 eq) was slowly added dropwise thereto, and the mixture was stirred at −78° C. for 0.5 hours. To this reaction solution, a tetrahydrofuran (2 ml) solution of N-tert-butoxycarbonyl-4-amino-1-iodobutane (484 mg, 1.618 mmol) was slowly added dropwise, and the mixture was stirred at −78° C. for 1 hour. After the reaction was confirmed by TLC to be complete, the temperature was adjusted to 0° C., and the reaction was terminated by the addition of water (15 ml), followed by extraction with ethyl acetate (15 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-(N-tert-butoxycarbonyl-4-amino-1-butyl)-1-methoxycarbonyl-3-indoleacetic acid methyl ester (373 mg, yield: 55%): $^1$H NMR (400 MHz, CDCl$_3$): δ 8.18 (d, J=7.8 Hz, 1H), 7.60 (d, J=7.8 Hz, 1H), 7.55 (s, 1H), 7.34 (t, J=7.9 Hz, 1H), 7.25 (t, J=7.7 Hz, 1H), 4.59 (s, 1H), 4.02 (s, 3H), 3.80 (t, J=7.6 Hz, 1H), 3.67 (s, 3H), 3.09 (m, 2H), 2.03 (m, 2H), 1.25-1.53 (m, 13H); $^{13}$C NMR (100 MHz, CDCl$_3$): δ 173.9, 155.9, 151.2, 135.5, 129.3, 124.8, 123.0, 122.9, 119.2, 115.2, 78.9, 53.6, 52.0, 42.5, 40.2, 31.7, 29.8, 28.3, 24.8; FAB-MS: m/z 419 [M+H]$^+$.

α-(N-tert-Butoxycarbonyl-4-amino-1-butyl)-3-indoleacetic Acid (Compound #15)

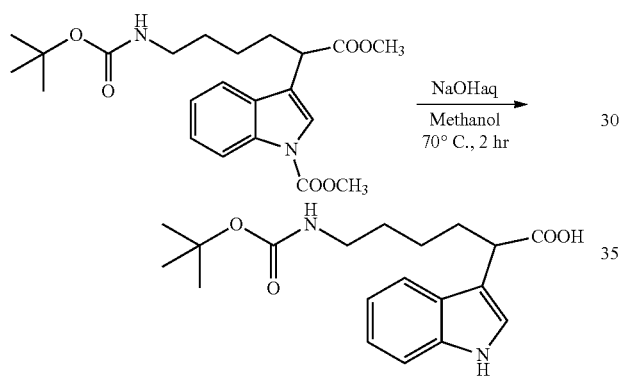

α-(N-tert-Butoxycarbonyl-4-amino-1-butyl)-1-methoxycarbonyl-3-indoleacetic acid methyl ester (100 mg, 0.239 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(N-tert-butoxycarbonyl-4-amino-1-butyl)-3-indoleacetic acid (compound #15) (71.8 mg, yield: 87%): $^1$H NMR (400 MHz, CDCl$_3$): δ 8.35 (s, 1H), 7.67 (d, J=7.8 Hz, 1H), 7.28 (d, J=7.8 Hz, 1H), 7.15 (t, J=7.7 Hz, 1H), 7.09 (t, J=7.3 Hz, 1H), 7.00 (s, 1H), 4.57 (s, 1H), 3.81 (t, J=7.5 Hz, 1H), 3.02 (m, 2H), 1.97 (m, 2H), 1.23-1.48 (m, 13H); $^{13}$C NMR (100 MHz, CDCl$_3$): δ 179.6, 156.1, 136.1, 126.4, 122.3, 122.0, 119.4, 119.1, 113.0, 111.8, 79.3, 42.9, 40.3, 31.9, 29.7, 28.4, 24.7; IR (neat): 3747, 1699, 1520, 1456, 1367, 1250, 1170 cm$^{-1}$; FAB-MS: m/z 347 [M+H]$^+$.

Synthesis of Compound #17

2-Ethyl-1-iodobutane

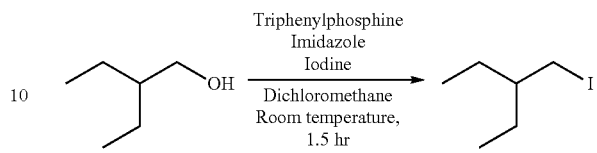

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 2-ethyl-1-butanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 2-ethyl-1-iodobutane (0.35 g, yield: 34%).

α-(2-Ethyl-1-butyl)-1-methoxycarbonyl-3-indoleacetic Acid Methyl Ester

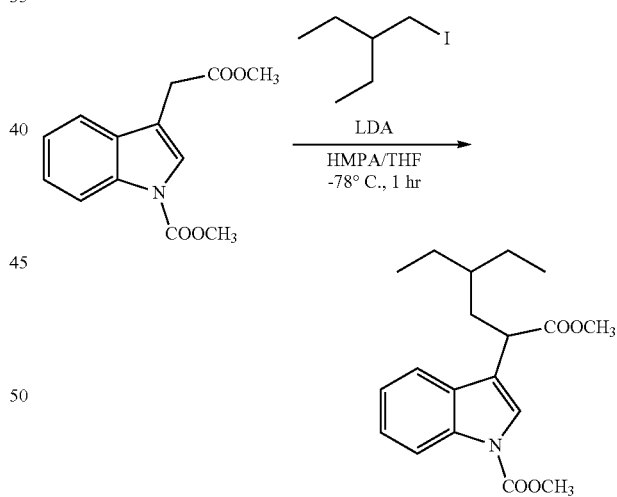

In a nitrogen atmosphere, 1-methoxycarbonyl-3-indoleacetic acid methyl ester (100 mg, 0.404 mmol) and hexamethylphosphoric triamide (HMPA, 362 mg, 2.020 mmol) were dissolved in tetrahydrofuran (2 ml), and the solution was cooled to −78° C. A 1.0 M solution of lithium bis(trimethylsilyl)amide (LHMDS) in tetrahydrofuran (0.61 ml, 1.5 eq) was slowly added dropwise thereto, and the mixture was stirred at −78° C. for 0.5 hours. To this reaction solution, a tetrahydrofuran (1 ml) solution of 2-ethyl-1-iodobutane (85.8 mg, 0.405 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain α-(2-ethyl-1-butyl)-1-methoxycarbonyl-3-indoleacetic acid methyl ester (104 mg, yield: 78%): $^1$H NMR (400 MHz, CDCl$_3$): δ 8.18 (d, J=7.0 Hz, 1H), 7.64 (d, J=7.8 Hz, 1H), 7.57 (s, 1H), 7.34 (t, J=7.7 Hz, 1H), 7.26 (t, J=7.4 Hz, 1H), 4.01 (s, 3H), 3.93 (t, J=7.8 Hz, 1H), 3.67 (s, 3H), 1.96 (m, 2H), 1.21-1.41 (m, 5H), 0.82-0.88 (m, 6H); $^{13}$C NMR (100 MHz, CDCl$_3$): δ 174.3, 151.3, 135.5, 129.5, 124.7, 122.9, 119.7, 119.3, 115.2, 53.7, 52.0, 40.4, 38.0, 35.6, 25.1, 24.9, 10.4, 10.4; IR (neat): 1738, 1455, 1377, 1256, 1164, 1085 cm$^{-1}$; EI-MS: m/z 331 [M]$^+$.

α-(2-Ethyl-1-butyl)-3-indoleacetic Acid (Compound #17)

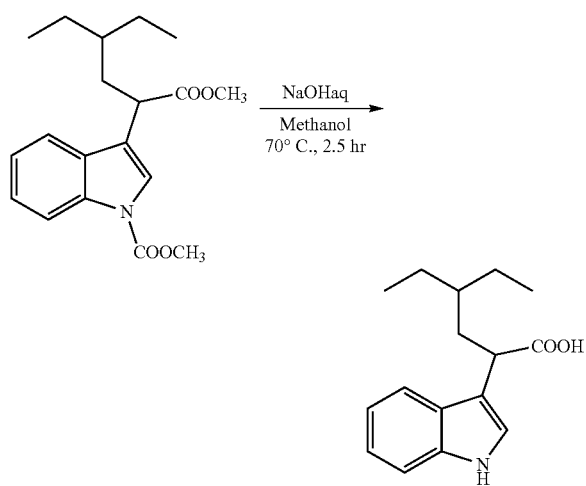

α-(2-Ethyl-1-butyl)-1-methoxycarbonyl-3-indoleacetic acid (70.0 mg, 0.211 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-ethyl-1-butyl)-3-indoleacetic acid (compound #17) (52.4 mg, yield: 96): $^1$H NMR (400 MHz, CDCl$_3$): δ 8.02 (s, 1H), 7.70 (d, J=7.9 Hz, 1H), 7.30 (d, J=8.0 Hz, 1H), 7.17 (t, J=7.9 Hz, 1H), 7.11 (t, J=7.5 Hz, 1H), 7.08 (s, 1H), 3.97 (t, J=7.8 Hz, 1H), 1.96 (m, 2H), 1.23-1.39 (m, 5H), 0.78-0.84 (m, 6H); $^{13}$C NMR (100 MHz, CDCl$_3$): δ 181.1, 136.1, 126.6, 122.2, 122.2, 119.7, 119.3, 113.7, 111.2, 40.6, 37.8, 35.9, 25.0, 25.0, 10.4, 10.4; IR (neat): 3414, 1703, 1458, 1293, 1098 cm$^{-1}$; FAB-MS: m/z 260 [M+H]$^+$.

Synthesis of Compound #18

3-Methyl-1-iodopentane

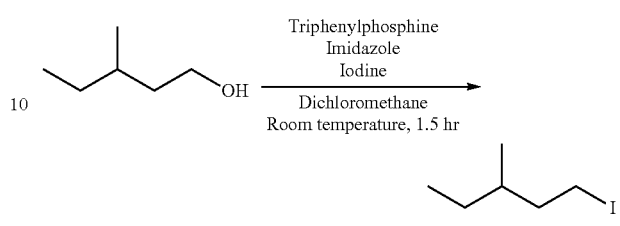

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 3-methyl-1-pentanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=98:2) to obtain 3-methyl-1-iodopentane (0.12 mg, yield: 11%).

α-(3-Methyl-1-pentyl)-1-methoxycarbonyl-3-indoleacetic Acid Methyl Ester

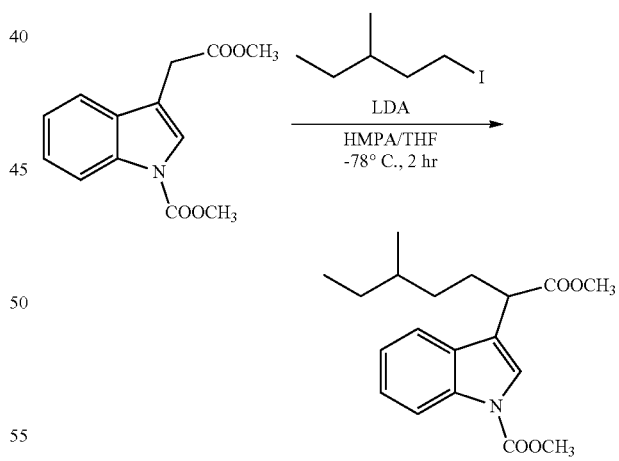

In a nitrogen atmosphere, 1-methoxycarbonyl-3-indoleacetic acid methyl ester (50.0 mg, 0.202 mmol) and hexamethylphosphoric triamide (HMPA, 181 mg, 1.011 mmol) were dissolved in tetrahydrofuran (1 ml), and the solution was cooled to −78° C. A 1.0 M solution of lithium bis(trimethylsilyl)amide (LHMDS) in tetrahydrofuran (0.30 ml, 1.5 eq) was slowly added dropwise thereto, and the mixture was stirred at −78° C. for 0.5 hours. To this reaction solution, a tetrahydrofuran (1 ml) solution of 3-methyl-1-iodopentane (51.5 mg, 0.243 mmol) was slowly added dropwise, and the mixture was stirred at −78° C. for 2 hours. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=12:1) to obtain α-(3-methyl-1-pentyl)-1-methoxycarbonyl-3-indoleacetic acid methyl ester (25.8 mg, yield: 39%): $^1$H NMR (400 MHz, CDCl$_3$): δ 8.18 (d, J=6.7 Hz, 1H), 7.62 (d, J=7.7 Hz, 1H), 7.56 (s, 1H), 7.34 (t, J=7.8 Hz, 1H), 7.26 (t, J=7.2 Hz, 1H), 4.03 (s, 3H), 3.77 (t, J=7.9 Hz, 1H), 3.68 (s, 3H), 2.01 (m, 2H), 1.10-1.39 (m, 5H), 0.82-0.87 (m, 6H); $^{13}$C NMR (100 MHz, CDCl$_3$): δ 174.2, 151.3, 135.5, 129.5, 124.8, 122.9, 119.4, 119.3, 115.2, 53.7, 52.0, 42.9, 34.4, 34.2, 29.8, 29.2, 19.1, 11.3; IR (neat): 1741, 1454, 1378, 1254, 1084 cm$^{-1}$; EI-MS: m/z 331 [M]$^+$.

α-(3-Methyl-1-pentyl)-3-indoleacetic Acid (Compound #18)

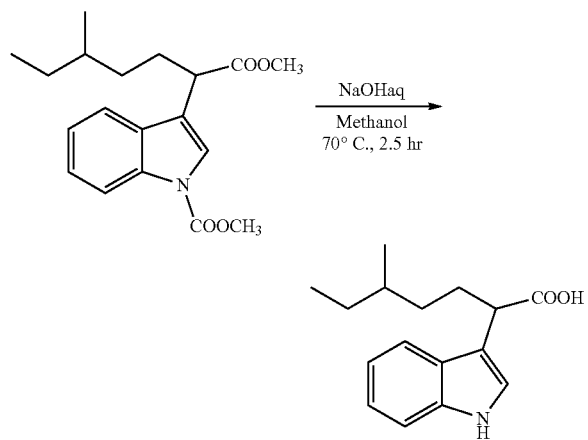

α-(3-Methyl-1-pentyl)-1-methoxycarbonyl-3-indoleacetic acid methyl ester (20.0 mg, 0.060 mmol) was dissolved in methanol (1 ml). To this solution, a 2 N aqueous sodium hydroxide solution (0.25 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(3-methyl-1-pentyl)-3-indoleacetic acid (compound #18) (16.8 mg, yield: 89%): $^1$H NMR (400 MHz, CDCl$_3$): δ 8.07 (s, 1H), 7.70 (d, J=7.8 Hz, 1H), 7.33 (d, J=8.1 Hz, 1H), 7.19 (t, J=8.0 Hz, 1H), 7.10-7.13 (m, 2H), 3.82 (t, J=6.7 Hz, 1H), 1.97 (m, 2H), 1.10-1.36 (m, 5H), 0.79-0.85 (m, 6H); $^{13}$C NMR (100 MHz, CDCl$_3$): δ 180.4, 136.1, 126.6, 122.2, 122.2, 119.7, 119.3, 113.7, 111.2, 43.2, 34.5, 34.3, 30.1, 29.2, 19.1, 11.3; IR (neat): 3418, 1704, 1456, 1294, 1098 cm$^{-1}$; EI-MS: m/z 259 [M]$^+$.

Synthesis of Compound #19

2-Methyl-1-iodopentane

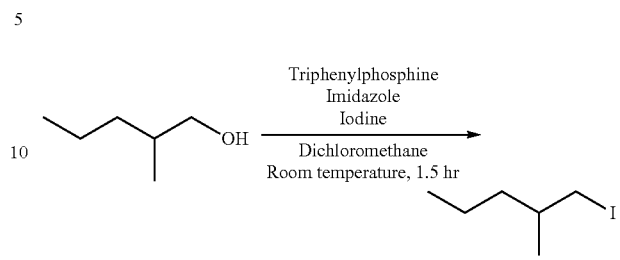

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 2-methyl-1-pentanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 2-methyl-1-iodopentane (0.56 g, yield: 54%).

α-(2-Methyl-1-pentyl)-1-methoxycarbonyl-3-indoleacetic Acid Methyl Ester

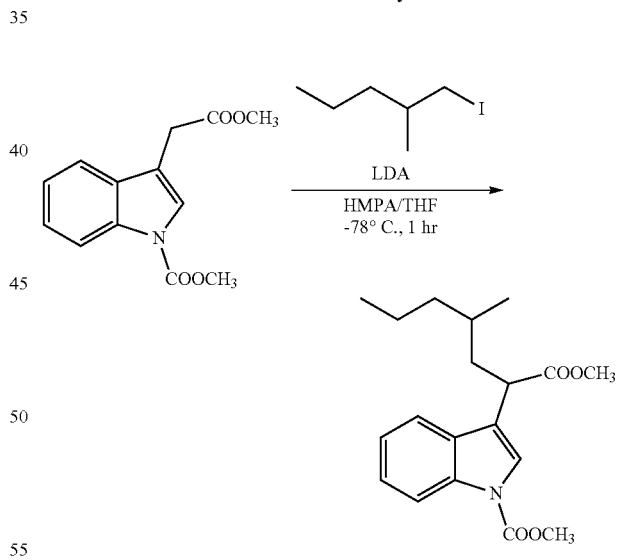

In a nitrogen atmosphere, 1-methoxycarbonyl-3-indoleacetic acid methyl ester (100 mg, 0.404 mmol) and hexamethylphosphoric triamide (HMPA, 362 mg, 2.020 mmol) were dissolved in tetrahydrofuran (2 ml), and the solution was cooled to −78° C. A 1.0 M solution of lithium bis(trimethylsilyl)amide (LHMDS) in tetrahydrofuran (0.61 ml, 1.5 eq) was slowly added dropwise thereto, and the mixture was stirred at −78° C. for 0.5 hours. To this reaction solution, a tetrahydrofuran (1 ml) solution of 2-methyl-1-iodopentane (85.8 mg, 0.405 mmol) was slowly added dropwise, and the mixture was stirred at −78° C. for 1 hour.

After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain α-(2-methyl-1-pentyl)-1-methoxycarbonyl-3-indoleacetic acid methyl ester (101 mg, yield: 75%): $^1$H NMR (400 MHz, CDCl$_3$): δ 8.18 (d, J=5.7 Hz, 1H), 7.63 (d, J=7.8 Hz, 1H), 7.55 (s, 1H), 7.34 (t, J=7.6 Hz, 1H), 7.27 (t, J=7.5 Hz, 1H), 4.03 (s, 3H), 3.91-3.97 (m, 1H), 3.68 (s, 3H), 1.58-2.24 (m, 2H), 1.10-1.50 (m, 5H), 0.83-0.97 (m, 6H); $^{13}$C NMR (100 MHz, CDCl$_3$): δ 174.4, 151.2, 135.4, 129.4, 124.7, 122.9, 122.8, 119.9, 119.4, 115.2, 53.7, 52.0, 40.4, 39.6, 39.3, 30.7, 19.8, 19.4, 14.2; IR (neat): 1739, 1456, 1373, 1217, 1087 cm$^{-1}$; FAB-MS: m/z 331 [M]$^+$.

α-(2-Methyl-1-pentyl)-3-indoleacetic Acid
(Compound #19)

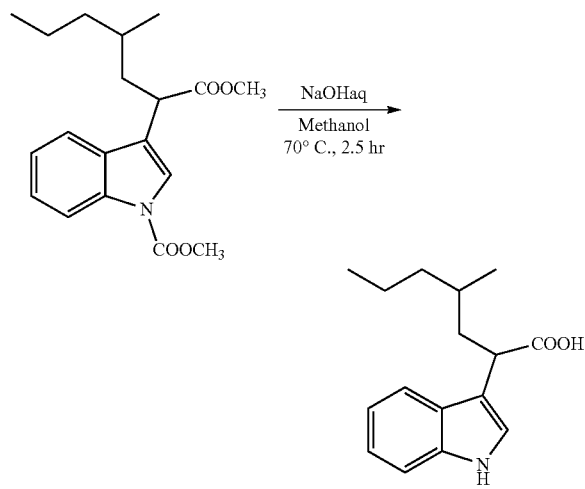

α-(2-Methyl-1-pentyl)-1-methoxycarbonyl-3-indoleacetic acid methyl ester (70.0 mg, 0.211 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-methyl-1-pentyl)-3-indoleacetic acid (compound #19) (51.9 mg, yield: 95%): $^1$H NMR (400 MHz, CDCl$_3$): δ 8.12 (s, 1H), 7.70 (d, J=7.8 Hz, 1H), 7.30 (d, J=8.0 Hz, 1H), 7.17 (t, J=7.4 Hz, 1H), 7.11 (t, J=7.2 Hz, 1H), 7.06 (s, 1H), 3.96-4.02 (m, 1H), 1.60-2.22 (m, 2H), 1.12-1.51 (m, 5H), 0.79-0.94 (m, 6H); $^{13}$C NMR (100 MHz, CDCl$_3$): δ 180.9, 136.1, 126.5, 122.3, 122.2, 119.7, 119.3, 113.3, 111.2, 40.7, 39.9, 39.2, 30.3, 19.8, 19.4, 14.3; IR (neat): 3417, 1699, 1457, 1292, 1099 cm$^{-1}$; EI-MS: m/z 259 [M]$^+$.

Synthesis of Compound #20

4-Phenyl-2-(1H-indol-3-yl)-4-oxo-butanoic Acid
(Compound #20)

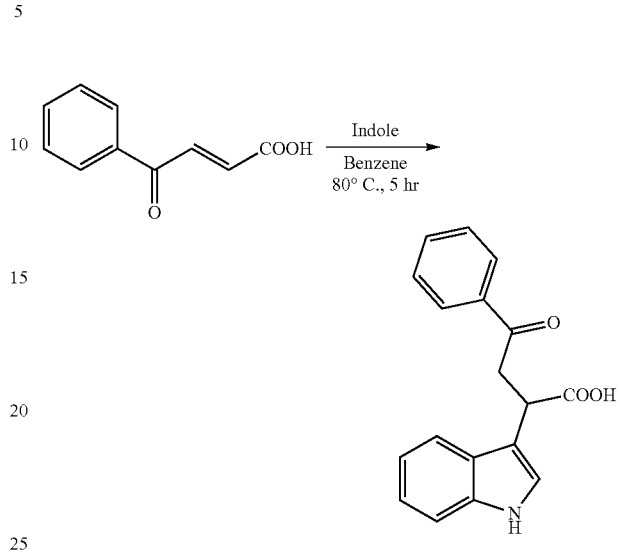

In a 30-mL round-bottomed flask, trans-4-phenyl-4-oxo-2-butenoic acid (1.0 g, 5.65 mmol) was dissolved in benzene (25 mL). To the solution, indole (0.79 g, 6.77 mmol) was added, and the mixture was stirred at 80° C. for 5 hours and stirred until the temperature became room temperature. The solvent in the reaction solution was distilled off under reduced pressure, and the residue was recrystallized from benzene to obtain 4-phenyl-2-(1H-indol-3-yl)-4-oxo-butanoic acid (compound #20) (1.24 g, yield: 75%); Melting point: 149 to 150° C.; $^1$H NMR (400 MHz, acetone-d$_6$): δ 10.17 (1H, brs, 1H), 8.05 (2H, d, J=8.2 Hz), 7.80 (1H, d, J=8.3 Hz), 7.57 (1H, t, J=7.8 Hz), 7.51 (2H, dd, J=8.2, 7.8 Hz), 7.41 (1H, d, J=8.2 Hz), 7.37 (1H, s), 7.13 (1H, t, J=8.2 Hz), 7.06 (1H, t, J=8.2 Hz), 4.57 (1H, dd, J=11.0, 4.1 Hz), 4.13 (1H, dd, J=17.8, 11.0 Hz), 3.41 (1H, dd, J=17.8, 4.1 Hz); IR: (neat): 3400, 3055, 1711, 1677, 1453 cm$^{-1}$; HRFAB-MS found m/z 294.1143 [M+H]$^+$, calcd for 294.1130 (C$_{18}$H$_{16}$NO$_3$).

Synthesis of Compound #21

4,4,5,5,5-Pentafluoro-1-iodopentane

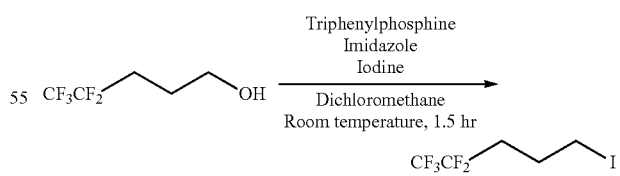

Triphenylphosphine (1.1 g, 4.211 mmol) and imidazole (0.29 g, 4.211 mmol) were dissolved in dichloromethane (5.0 ml), and the solution was stirred for 5 minutes. Then, iodine (1.07 g, 4.211 mmol) was added thereto, and the mixture was stirred for 10 minutes. A dichloromethane (2.0 ml) solution of 4,4,5,5,5-pentafluoro-1-pentanol (0.5 g, 2.807 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 4,4,5,5,5-pentafluoro-1-iodopentane (0.36 g, yield: 45%).

α-(4,4,5,5,5-Pentafluoro-1-pentyl)-1-methoxycarbonyl-3-indoleacetic Acid Methyl Ester

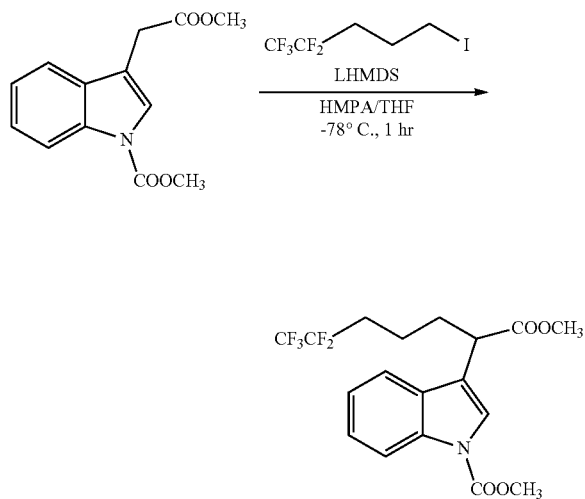

In a nitrogen atmosphere, 1-methoxycarbonyl-3-indoleacetic acid methyl ester (50.0 mg, 0.202 mmol) and hexamethylphosphoric triamide (HMPA, 181 mg, 1.011 mmol) were dissolved in tetrahydrofuran (1 ml), and the solution was cooled to −78° C. A 1.0 M solution of lithium bis(trimethylsilyl)amide (LHMDS) in tetrahydrofuran (0.30 ml, 1.5 eq) was slowly added dropwise thereto, and the mixture was stirred at −78° C. for 0.5 hours. To this reaction solution, a tetrahydrofuran (1 ml) solution of 4,4,5,5,5-pentafluoro-1-iodopentane (81.4 mg, 0.283 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=85:15) to obtain α-(4,4,5,5,5-pentafluoro-1-pentyl)-1-methoxycarbonyl-3-indoleacetic acid methyl ester (59.8 mg, yield: 73%): $^1$H NMR (400 MHz, CDCl$_3$): δ 8.19 (d, J=7.6 Hz, 1H), 7.60 (d, J=7.8 Hz, 1H), 7.57 (s, 1H), 7.36 (t, J=7.5 Hz, 1H), 7.27 (t, J=6.9 Hz, 1H), 4.03 (s, 3H), 3.83 (t, J=7.6 Hz, 1H), 3.69 (s, 3H), 1.98-2.23 (m, 4H), 1.62-1.68 (m, 2H); $^{13}$C NMR (100 MHz, CDCl$_3$): δ 173.5, 151.3, 135.5, 129.1, 125.0, 123.1, 123.1, 119.2, 118.6, 115.3, 53.8, 52.2, 42.3, 31.4, 30.6, 30.3, 30.1, 18.6; IR (neat): 1739, 1456, 1378, 1257, 1198 cm$^{-1}$; EI-MS: m/z 407 [M]$^+$.

α-(4,4,5,5,5-Pentafluoro-1-pentyl)-3-indoleacetic Acid (Compound #21)

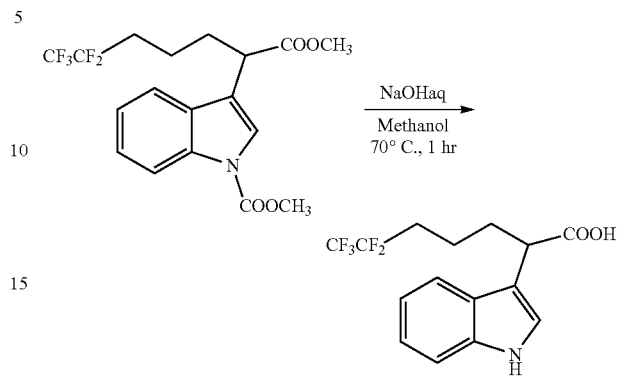

α-(4,4,5,5,5-Pentafluoro-1-pentyl)-1-methoxycarbonyl-3-indoleacetic acid methyl ester (55.5 mg, 0.183 mmol) was dissolved in methanol (1 ml). To this solution, a 2 N aqueous sodium hydroxide solution (0.25 ml) was added, and the mixture was stirred at 70° C. for 1 hour. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(4,4,5,5,5-pentafluoro-1-pentyl)-3-indoleacetic acid (compound #21) (43.9 mg, yield: 97%): $^1$H NMR (400 MHz, CDCl$_3$): δ 8.06 (s, 1H), 7.67 (d, J=7.9 Hz, 1H), 7.33 (d, J=8.1 Hz, 1H), 7.20 (t, J=8.0 Hz, 1H), 7.12 (t, J=7.9 Hz, 1H), 7.09 (s, 1H), 3.87 (t, J=7.5 Hz, 1H), 1.95-2.22 (m, 4H), 1.60-1.67 (m, 2H); $^{13}$C NMR (100 MHz, CDCl$_3$): δ 179.9, 136.2, 126.2, 122.4, 122.4, 119.9, 119.1, 112.5, 111.4, 42.7, 31.5, 30.6, 30.3, 30.1, 18.6; IR (neat): 3418, 1704, 1459, 1198 cm$^{-1}$; EI-MS: m/z 335 [M]$^+$.

Synthesis of Compound #22

3-(2-Hydroxy-1-ethyl)-1,1'-biphenyl

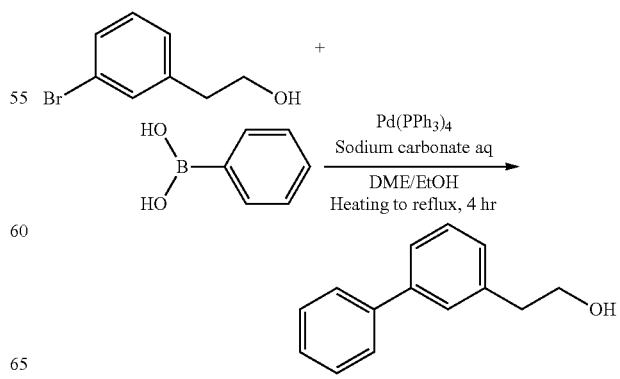

2-(3-Bromophenyl)-1-ethanol (200 mg, 0.995 mmol) was dissolved in a mixed solvent of dimethoxyethane:ethanol (=5:1) (3.0 ml). To the solution, phenylboronic acid (242 mg, 1.985 mmol), a 2 M aqueous sodium carbonate solution (1.5 ml), and tetrakis(triphenylphosphine) palladium(0) (Pd(PPh$_3$)$_4$, 56.0 mg, 0.048 mmol) were added, and the mixture was stirred for 4 hours under heating to reflux. After the reaction was confirmed by TLC to be complete, the reaction solution was filtered through celite, and the filtrate was neutralized by the addition of hydrochloric acid, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain 3-(2-hydroxy-1-ethyl)-1,1'-biphenyl (172 mg, yield: 87%).

3-(2-Iodo-1-ethyl)-1,1'-biphenyl

Triphenylphosphine (327 mg, 1.248 mmol) and imidazole (85.0 mg, 1.249 mmol) were dissolved in dichloromethane (3.0 ml), and the solution was stirred for 5 minutes. Then, iodine (317 mg, 1.248 mmol) was added thereto, and the mixture was stirred for 10 minutes. A dichloromethane (0.5 ml) solution of 3-(2-hydroxy-1-ethyl)-1,1'-biphenyl (165 mg, 0.832 mmol) was added dropwise thereto, and the mixture was stirred at room temperature for 1 hour. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=98:2) to obtain 3-(2-iodo-1-ethyl)-1,1'-biphenyl (185 mg, yield: 72%).

α-[2-(1,1'-Biphenyl-3-yl)-1-ethyl]-1-methoxycarbonyl-3-indoleacetic Acid Methyl Ester

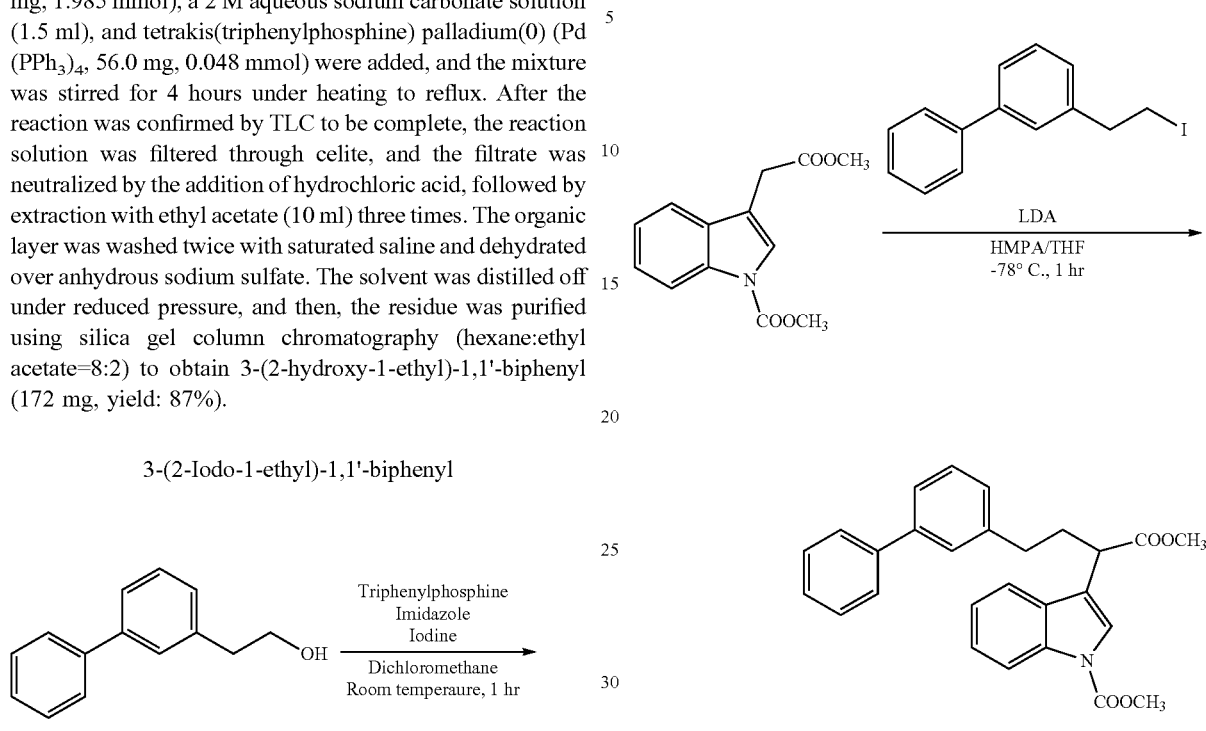

In a nitrogen atmosphere, 1-methoxycarbonyl-3-indoleacetic acid methyl ester (80 mg, 0.324 mmol) and hexamethylphosphoric triamide (HMPA, 290 mg, 1.618 mmol) were dissolved in tetrahydrofuran (2 ml), and the solution was cooled to −78° C. A 1.5 M solution of lithium diisopropylamide (LDA) in cyclohexane (0.32 ml, 1.5 eq) was slowly added dropwise thereto, and the mixture was stirred at −78° C. for 0.5 hours. To this reaction solution, a tetrahydrofuran (1 ml) solution of 3-(2-iodo-1-ethyl)-1,1'-biphenyl (99.7 mg, 0.324 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=85:15) to obtain α-[2-(1,1'-biphenyl-3-yl)-1-ethyl]-1-methoxycarbonyl-3-indoleacetic acid methyl ester (132 mg, yield: 96%): $^1$H NMR (400 MHz, CDCl$_3$): δ 8.19 (d, J=6.8 Hz, 1H), 7.55-7.58 (m, 4H), 7.31-7.44 (m, 7H), 7.24 (t, J=8.1 Hz, 1H), 7.15 (d, J=7.5 Hz, 1H), 4.02 (s, 3H), 3.86 (t, J=7.5 Hz, 1H), 3.65 (S, 3H), 2.73 (t, J=7.7 Hz, 2H), 2.25-2.58 (m, 2H); $^{13}$C NMR (100 MHz, CDCl$_3$): δ 173.8, 151.2, 141.4, 141.3, 141.1, 135.5, 129.3, 128.8, 128.6, 127.3, 127.2, 127.1, 124.9, 124.8, 123.1, 122.9, 119.3, 118.9, 115.2, 53.7, 52.1, 41.8, 33.7, 33.5; EI-MS: m/z 427 [M]$^+$.

α-[2-(1,1'-Biphenyl-3-yl)-1-ethyl]-3-indoleacetic Acid (Compound #22)

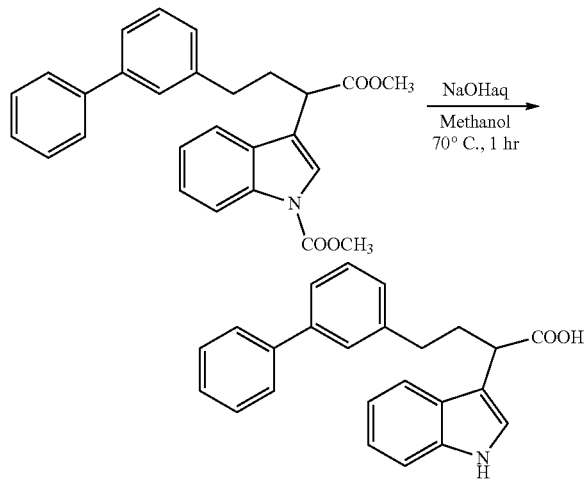

α-[2-(1,1'-Biphenyl-3-yl)-1-ethyl]-1-methoxycarbonyl-3-indoleacetic acid methyl ester (80.0 mg, 0.187 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-[2-(1,1'-biphenyl-3-yl)-1-ethyl]-3-indoleacetic acid (compound #22) (60.3 mg, yield: 91%): $^1$H NMR (400 MHz, CDCl$_3$): δ 8.01 (s, 1H), 7.65 (d, J=7.9 Hz, 1H), 7.53-7.55 (m, 2H), 7.29-7.41 (m, 7H), 7.17 (t, J=7.2 Hz, 1H), 7.07-7.13 (m, 3H), 3.91 (t, J=7.5 Hz, 1H), 2.71 (t, J=7.7 Hz, 2H), 2.39 (m, 2H); $^{13}$C NMR (100 MHz, CDCl$_3$): δ 180.3, 141.8, 141.3, 141.2, 136.1, 128.8, 128.7, 127.4, 127.4, 127.2, 126.4, 124.9, 122.4, 122.3, 119.8, 119.3, 112.9, 111.3, 42.2, 33.8, 33.7; IR (neat): 3420, 1699, 1456, 1216, 1097 cm$^{-1}$; EI-MS: m/z 355 [M]$^+$.

Synthesis of Compound #23

α-(2-Phenyl-1-ethyl)-1-methoxycarbonyl-3-indoleacetic Acid Methyl Ester

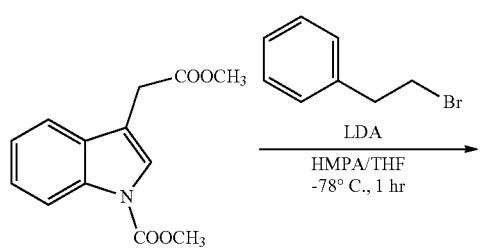

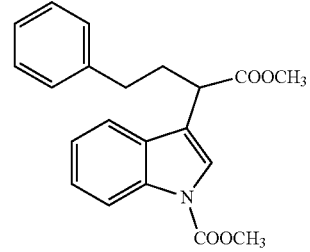

In a nitrogen atmosphere, 1-methoxycarbonyl-3-indoleacetic acid methyl ester (300 mg, 1.213 mmol) and hexamethylphosphoric triamide (HMPA, 1.09 g, 6.067 mmol) were dissolved in tetrahydrofuran (2 ml), and the solution was cooled to −78° C. A 1.5 M solution of lithium diisopropylamide (LDA) in cyclohexane (1.21 ml, 1.5 eq) was slowly added dropwise thereto, and the mixture was stirred at −78° C. for 0.5 hours. To this reaction solution, a tetrahydrofuran (2 ml) solution of 1-bromo-2-phenylethane (292 mg, 1.577 mmol) was slowly added dropwise, and the mixture was stirred at −78° C. for 1 hour. After the reaction was confirmed by TLC to be complete, the temperature was adjusted to 0° C., and the reaction was terminated by the addition of water (10 ml), followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (benzene) to obtain α-(2-phenyl-1-ethyl)-1-methoxycarbonyl-3-indoleacetic acid methyl ester (228 mg, yield: 54%): $^1$H NMR (400 MHz, CDCl$_3$): δ 8.18 (d, J=6.0 Hz, 1H), 7.57 (s, 1H), 7.55 (d, J=8.0 Hz, 1H), 7.31 (t, J=7.8 Hz, 1H), 7.13-7.26 (m, 6H), 3.94 (s, 3H), 3.83 (t, J=7.5 Hz, 1H), 3.64 (s, 3H), 2.66 (t, J=7.8 Hz, 2H), 2.35 (m, 2H); $^{13}$C NMR (100 MHz, CDCl$_3$): δ 173.8, 151.2, 140.9, 135.4, 129.3, 128.4, 128.3, 126.0, 124.8, 123.1, 122.9, 119.3, 119.0, 115.2, 53.7, 52.0, 41.8, 33.5; EI-MS: m/z 351 [M]$^+$.

α-(2-Phenyl-1-ethyl)-3-indoleacetic Acid (Compound #23)

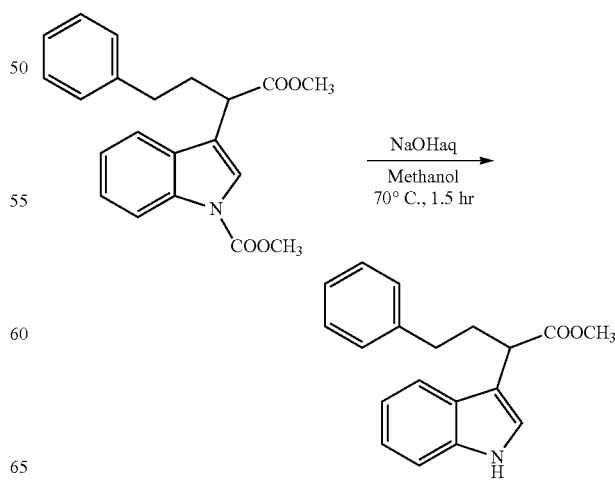

α-(2-Phenyl-1-ethyl)-1-methoxycarbonyl-3-indoleacetic acid methyl ester (150 mg, 0.427 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-phenyl-1-ethyl)-3-indoleacetic acid (compound #23) (85.3 mg, yield: 72%): $^1$H NMR (400 MHz, acetone-d$_6$): δ 10.16 (s, 1H), 7.67 (d, J=8.0 Hz, 1H), 7.40 (d, J=8.1 Hz, 1H), 7.09-7.32 (m, 7H), 7.03 (t, J=7.6 Hz, 1H), 3.93 (t, J=7.4 Hz, 1H), 2.67 (t, J=5.4 Hz, 2H), 2.35 (m, 2H); $^{13}$C NMR (100 MHz, acetone-d$_6$): δ 175.4, 142.4, 137.2, 128.8, 128.7, 127.2, 126.2, 123.2, 121.8, 119.4, 119.2, 113.6, 111.8, 42.5, 34.9, 34.1; IR (neat): 3416, 1700, 1457, 1246, 1098 cm$^{-1}$; FAB-MS: m/z 280 [M+H]$^+$.

Synthesis of Compound #24

2-Cyclopentyl-1-iodoethane

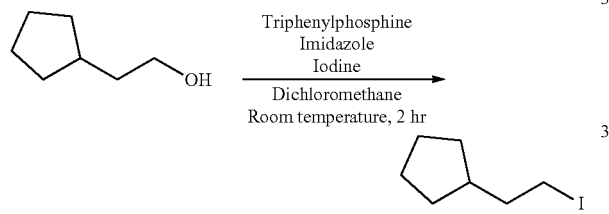

Triphenylphosphine (1.03 g, 3.942 mmol) and imidazole (0.27 g, 3.937 mmol) were dissolved in dichloromethane (5 ml), and the solution was stirred for 5 minutes. Then, iodine (1.0 g, 3.940 mmol) was added thereto, and the mixture was stirred for 10 minutes. A dichloromethane (1 ml) solution of 2-cyclopentyl-1-ethanol (0.3 g, 2.627 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 2-cyclopentyl-1-iodoethane (0.46 g, yield: 84%).

1-Methoxycarbonyl-3-indoleacetic Acid Methyl Ester

Indole-3-acetic acid methyl ester (2.00 g, 10.57 mmol) was dissolved in dichloromethane (30 ml). To this solution, tetrabutylammonium iodide (TBAI, 30.0 mg, 0.081 mmol) and a 30% aqueous sodium hydroxide solution (24 ml) were added, and the mixture was cooled to 0° C. To the reaction solution, methyl formate chloride (1.96 g, 20.73 mmol) was added, and the mixture was stirred at 0° C. for 2 hours. After the reaction was confirmed by TLC to be complete, the reaction was terminated by the addition of 6 N hydrochloric acid. Water (50 ml) was added thereto, followed by extraction with chloroform (50 ml) three times. The organic layer was washed twice with saturated saline and dried over anhydrous sodium sulfate. The solvent was distilled off under reduced pressure, and the residue was then purified using silica gel column chromatography (hexane:ethyl acetate=8:2) to obtain 1-methoxycarbonyl-3-indoleacetic acid methyl ester (2.26 g, yield: 87%): $^1$H NMR (400 MHz, CDCl$_3$): δ 8.18 (d, J=7.0 Hz, 1H), 7.59 (s, 1H), 7.53 (d, J=7.7 Hz, 1H), 7.35 (t, J=7.5 Hz, 1H), 7.27 (t, J=7.4 Hz, 1H), 4.00 (s, 3H), 3.72 (s, 3H), 3.71 (s, 2H); $^{13}$C-NMR (100 MHz, CDCl$_3$): δ 171.1, 151.1, 135.2, 129.9, 124.6, 123.8, 122.8, 118.9, 115.0, 113.8, 53.5, 51.9, 30.6; EI-MS: m/z 247 [M]$^+$ α-(2-Cyclopentyl-1-ethyl)-1-methoxycarbonyl-3-indoleacetic Acid Methyl Ester

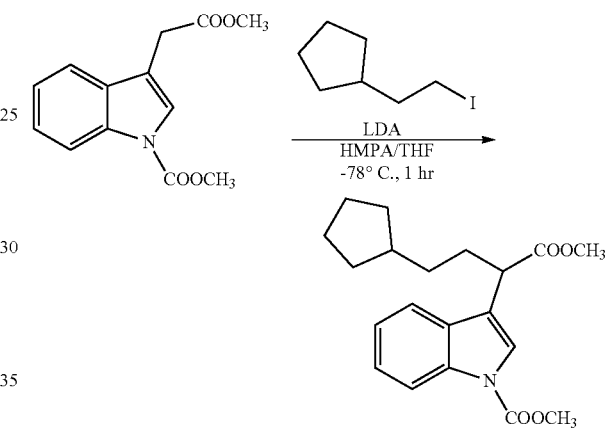

In a nitrogen atmosphere, 1-methoxycarbonyl-3-indoleacetic acid methyl ester (150 mg, 0.607 mmol) and hexamethylphosphoric triamide (544 mg, 3.036 mmol) were dissolved in anhydrous tetrahydrofuran 2 ml, and the solution was cooled to −78° C. A 1.5 M solution of lithium diisopropylamide in cyclohexane (0.61 ml, 1.5 eq) was slowly added dropwise thereto, and the mixture was stirred at −78° C. for 0.5 hours. To this reaction solution, a anhydrous tetrahydrofuran 1 ml solution of 2-cyclopentyl-1-iodoethane (204 mg, 0.910 mmol) was slowly added dropwise, and the mixture was stirred at −78° C. for 1 hour. After the reaction was confirmed by TLC to be complete, the temperature was adjusted to 0° C., and the reaction was terminated by the addition of water 5 ml, followed by extraction with ethyl acetate 5 ml three times. The organic layer was washed twice with saturated saline and dehydrated over anhydrous sodium sulfate. The solvent was distilled off under reduced pressure, and then, the residue was purified using silica gel column chromatography (hexane:ethyl acetate=95:5) to obtain α-(2-cyclopentyl-1-ethyl)-1-methoxycarbonyl-3-indoleacetic acid methyl ester (151 mg, yield: 72%): $^1$H NMR (400 MHz, CDCl3): δ 8.18 (d, J=6.8 Hz, 1H), 7.62 (d, J=7.7 Hz, 1H), 7.56 (s, 1H), 7.34 (t, J=7.4 Hz, 1H), 7.26 (t, J=7.3 Hz, 1H), 4.02 (s, 3H), 3.79 (t, J=7.6 Hz, 1H), 3.68 (s, 3H), 2.03 (m, 2H), 1.73-1.77 (m, 3H), 1.48-1.58 (m, 4H), 1.34 (q, J=7.2 Hz, 2H), 1.04-1.07 (m, 2H); 13C-NMR (100 MHz, CDCl3): d 174.2, 151.3, 135.5, 129.5, 124.7, 122.9, 119.5, 119.3, 115.2, 53.7, 52.0, 42.8, 39.9, 34.1, 32.6, 32.5, 31.4, 25.1; EI-MS: m/z 343 [M]$^+$

α-(2-Cyclopentyl-1-ethyl)-1-methoxycarbonyl-3-indoleacetic Acid Methyl Ester (Compound #24)

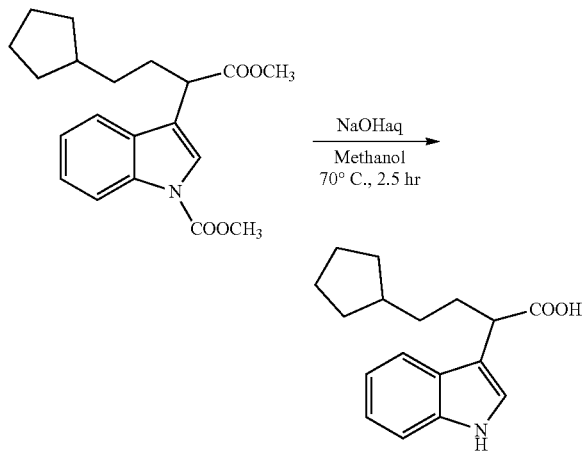

α-(2-Cyclopentyl-1-ethyl)-1-methoxycarbonyl-3-indoleacetic acid methyl ester (100 mg, 0.291 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-cyclopentyl-1-ethyl)-1-methoxycarbonyl-3-indoleacetic acid methyl ester (compound #24) (78.5 mg, yield: 99%): $^1$H NMR (400 MHz, CDCl$_3$): δ 8.19 (s, 1H), 7.69 (d, J=7.9 Hz, 1H), 7.29 (d, J=8.0 Hz, 1H), 7.16 (t, J=8.0 Hz, 1H), 7.10 (t, J=7.5 Hz, 1H), 7.06 (s, 1H), 3.83 (t, J=7.6 Hz, 1H), 2.01 (m, 2H), 1.70-1.75 (m, 3H), 1.45-1.55 (m, 4H), 1.34-1.37 (m, 2H), 0.98-1.03 (m, 2H); $^{13}$C NMR (100 MHz, CDCl$_3$): δ 180.7, 136.1, 126.5, 122.2, 122.0, 119.5, 119.2, 113.4, 111.2, 43.1, 39.9, 34.1, 32.5, 31.6, 25.1; IR (neat): 3415, 1703, 1457, 1339, 1098 cm$^{-1}$; FAB-MS: m/z 294 [M+Na]$^+$.

Synthesis of Compound #25

Cyclopentyliodomethane

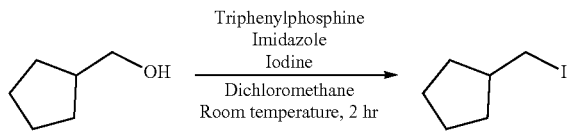 [SMILES: OCC1CCCC1 ; ICC1CCCC1]

Triphenylphosphine (1.18 g, 4.491 mmol) and imidazole (0.31 g, 4.495 mmol) were dissolved in dichloromethane (5 ml), and the solution was stirred for 5 minutes. Then, iodine (1.14 g, 4.492 mmol) was added thereto, and the mixture was stirred for 10 minutes. A dichloromethane (1 ml) solution of cyclopentylmethanol (0.3 g, 2.995 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain cyclopentyliodomethane (0.53 g, yield: 84%).

α-Cyclopentylmethyl-1-methoxycarbonyl-3-indoleacetic Acid Methyl Ester

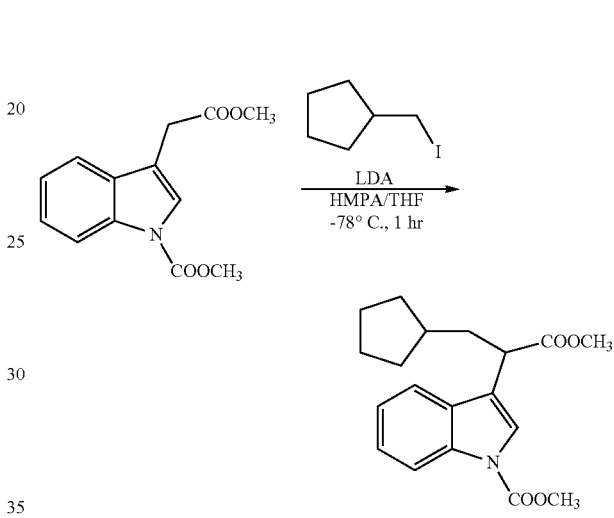

In a nitrogen atmosphere, 1-methoxycarbonyl-3-indoleacetic acid methyl ester (150 mg, 0.607 mmol) and hexamethylphosphoric triamide (HMPA, 544 mg, 3.036 mmol) were dissolved in tetrahydrofuran (2 ml), and the solution was cooled to −78° C. A 1.5 M solution of lithium diisopropylamide (LDA) in cyclohexane (0.61 ml, 1.5 eq) was slowly added dropwise thereto, and the mixture was stirred at −78° C. for 0.5 hours. To this reaction solution, a tetrahydrofuran (1 ml) solution of cyclopentyliodomethane (153 mg, 0.728 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=13:1) to obtain α-cyclopentylmethyl-1-methoxycarbonyl-3-indoleacetic acid methyl ester (153 mg, yield: 76%): $^1$H NMR (400 MHz, CDCl$_3$): δ 8.18 (d, J=6.0 Hz, 1H), 7.63 (d, J=7.8 Hz, 1H), 7.57 (s, 1H), 7.32 (t, J=7.4 Hz, 1H), 7.25 (t, J=7.4 Hz, 1H), 3.99 (s, 3H), 3.88 (t, J=7.7 Hz, 1H), 3.67 (s, 3H), 2.05 (m, 2H), 1.76-1.79 (m, 3H), 1.59-1.62 (m, 2H), 1.47-1.50 (m, 2H), 1.12-1.17 (m, 2H); $^{13}$C NMR (100 MHz, CDCl$_3$): δ 174.1, 151.1, 135.4, 129.4, 124.6, 122.8, 119.4, 119.1, 115.1, 53.6, 51.9, 41.7, 38.5, 37.9, 32.5, 32.3, 24.9; EI-MS: m/z 329 [M]$^+$.

α-Cyclopentylmethyl-3-indoleacetic Acid (Compound #25)

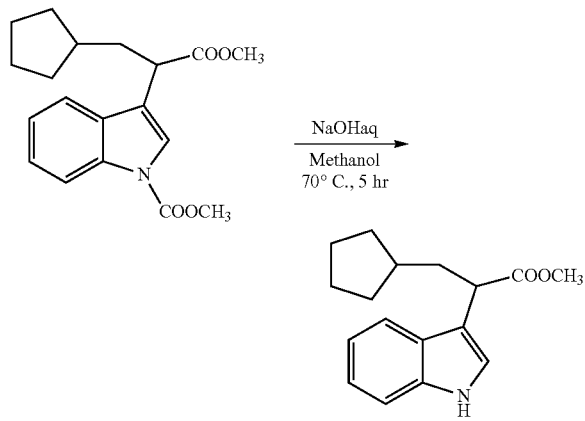

α-Cyclopentylmethyl-1-methoxycarbonyl-3-indoleacetic acid methyl ester (100 mg, 0.304 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-cyclopentylmethyl-3-indoleacetic acid (compound #25) (58.3 mg, yield: 75%); $^1$H NMR (400 MHz, acetone-$d_6$): δ 10.13 (s, 1H), 7.70 (d, J=7.8 Hz, 1H), 7.38 (d, J=8.1 Hz, 1H), 7.28 (s, 1H), 7.10 (t, J=8.0 Hz, 1H), 7.02 (t, J=7.1 Hz, 1H), 3.73 (t, J=7.7 Hz, 1H), 2.06 (m, 2H), 1.78-1.83 (m, 3H), 1.47-1.61 (m, 4H), 1.17-1.20 (m, 2H); $^{13}$C NMR (100 MHz, acetone-$d_6$): δ 175.8, 137.3, 127.4, 123.1, 121.8, 119.5, 119.2, 114.1, 111.9, 42.4, 39.6, 38.7, 32.9, 32.9, 25.3, 25.3; IR (neat): 3418, 1699, 1456, 1339, 1097 cm-1; FAB-MS: m/z 258 [M+H]$^+$.

Compounds #26 to 31 were each synthesized according to a method described in Muro Fumihito et. al. "Discovery of trans-4-[1-[[2,5-Dichloro-4-(1-methyl-3-indolylcarboxamido)phenyl]acetyl]-(4S)-methoxy-(2S)-pyrrolidinylmethoxy]cyclohexanecarboxylic Acid: An Orally Active, Selective Very Late Antigen-4 Antagonist" Journal of Medicinal Chemistry, 52 (24), 7974-7992; 2009.

Synthesis of Compound #26

N-Methyl-3-indoleacetic Acid Methyl Ester

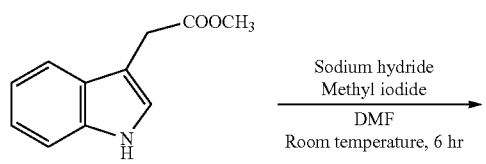

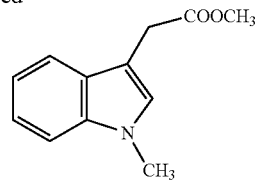

3-Indoleacetic acid methyl ester (200 mg, 1.1 mmol) was dissolved in N,N-dimethylformamide (3 mL). To the solution, sodium hydride (60 mg) was added. To this solution, methyl iodide (223 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=5:1) to obtain N-methyl-3-indoleacetic acid methyl ester (140 mg, yield: 65%); $^1$H NMR (400 MHz, CDCl$_3$): δ 7.60 (d, J=7.9 Hz, 1H), 7.29 (d, J=8.2 Hz, 1H), 7.23 (dd, J=8.2, 7.9 Hz, 1H), 7.12 (dd, J=8.2, 7.9 Hz, 1H), 7.03 (s, 1H), 3.75 (s, 3H), 3.77 (s, 2H), 3.69 (s, 3H); $^{13}$C NMR (100 MHz, CDCl$_3$): δ 172.6, 136.9, 127.7, 121.7 (2C), 119.26, 118.9, 109.3, 106.8, 51.9, 32.7, 31.0.

N-Methyl-3-indoleacetic Acid (Compound #26)

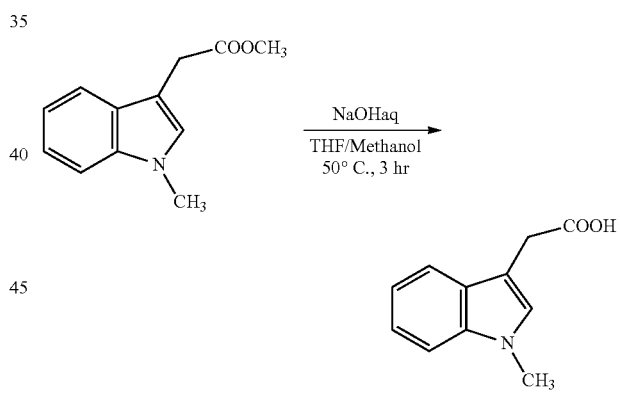

N-Methyl-3-indoleacetic acid methyl ester (120 mg, 0.59 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-methyl-3-indoleacetic acid (compound #26) (108 mg, yield: 96%); $^1$H NMR (400 MHz, CDCl$_3$): δ 7.59 (d, J=8.0 Hz, 1H), 7.35 (d, J=8.1 Hz, 1H), 7.18 (s, 1H), 7.16 (dd, J=7.0, 6.1 Hz, 1H), 7.04 (dd, J=8.1, 6.7 Hz, 1H), 3.79 (s, 3H), 3.73 (s, 2H). $^{13}$C NMR (100 MHz, CDCl$_3$): δ 177.6, 136.8, 127.9, 127.5, 121.8, 119.2, 118.9, 109.5, 106.1, 53.7, 31.7.

Synthesis of Compound #27

N-Ethyl-3-indoleacetic Acid Methyl Ester

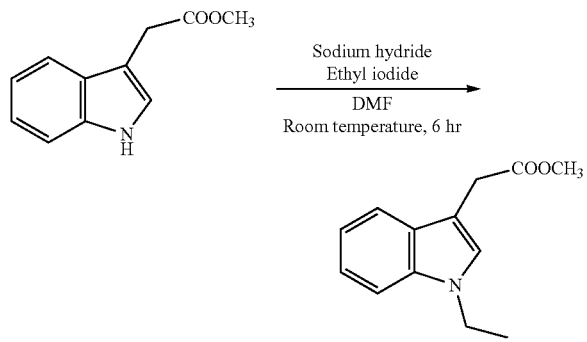

3-Indoleacetic acid methyl ester (200 mg, 1.1 mmol) was dissolved in N,N-dimethylformamide (3 mL). To the solution, sodium hydride (60 mg) was added. To this solution, ethyl iodide (246 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=5:1) to obtain N-ethyl-3-indoleacetic acid methyl ester (133 mg, yield: 58%); $^1$H NMR (400 MHz, CDCl$_3$): δ 7.60 (d, J=7.8 Hz, 1H), 7.31 (d, J=8.3 Hz, 1H), 7.21 (dd, J=8.3, 7.8 Hz, 1H), 7.11 (dd, J=8.3, 7.8 Hz, 1H), 7.09 (s, 1H), 4.11 (q, J=7.3 Hz, 2H), 3.76 (s, 2H), 3.68 (s, 3H), 1.43 (t, J=7.3, 3H); $^{13}$C NMR (100 MHz, CDCl$_3$): δ 172.6, 160.8, 135.9, 127.8, 125.9, 121.6, 119.0, 109.3, 51.9, 40.8, 31.1, 15.4.

N-Ethyl-3-indoleacetic Acid (Compound #27)

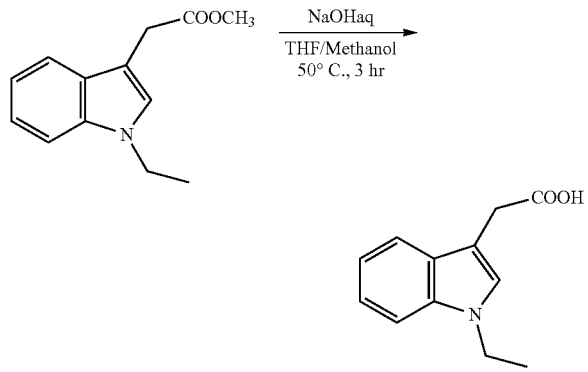

N-Methyl-3-indoleacetic acid methyl ester (120 mg, 0.59 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-methyl-3-indoleacetic acid (compound #27) (108 mg, yield: 97%); $^1$H NMR (400 MHz, CDCl$_3$): δ 7.60 (d, J=7.9 Hz, 1H), 7.40 (d, J=8.2 Hz, 1H), 7.25 (s, 1H), 7.15 (ddd, J=7.5, 7.6 Hz, 1H), 7.04 (ddd, J=7.3, 7.5 Hz, 1H), 4.20 (q, J=7.3 Hz, 2H), 3.74 (s, 2H), 1.39 (t, J=7.3 Hz, 3H); $^{13}$C NMR (100 MHz, CDCl$_3$): δ 173.3, 136.8, 129.0, 127.1, 122.0, 119.8, 119.4, 110.1, 108.1, 41.1, 31.9, 15.8.

Synthesis of Compound #28

N-Propyl-3-indoleacetic Acid Methyl Ester

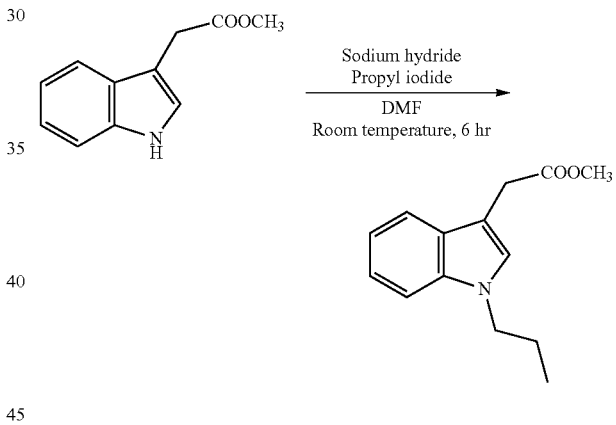

3-Indoleacetic acid methyl ester (200 mg, 1.1 mmol) was dissolved in N,N-dimethylformamide (3 mL). To the solution, sodium hydride (60 mg) was added. To this solution, propyl iodide (268 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-propyl-3-indoleacetic acid methyl ester (136 mg, yield: 56%); $^1$H NMR (400 MHz, CDCl$_3$): δ 7.60 (d, J=7.8 Hz, 1H) 7.31 (d, J=8.3 Hz, 1H) 7.21 (dd, J=8.0, 7.1 Hz, 1H) 7.11 (dd, J=7.7, 6.9 Hz, 1H) 7.08 (s, 1H) 4.04 (t, J=7.1 Hz, 2H) 3.77 (s, 2H) 3.69 (s, 3H) 1.86 (m, 2H) 0.93 (t, J=7.3 Hz, 3H); $^{13}$C NMR (100 MHz, CDCl$_3$): δ 172.6, 136.2, 127.70, 126.7, 121.5, 119.0, 119.0, 109.4, 106.6, 51.9, 47.9, 31.1, 23.5, 11.5.

N-Propyl-3-indoleacetic Acid (Compound #28)

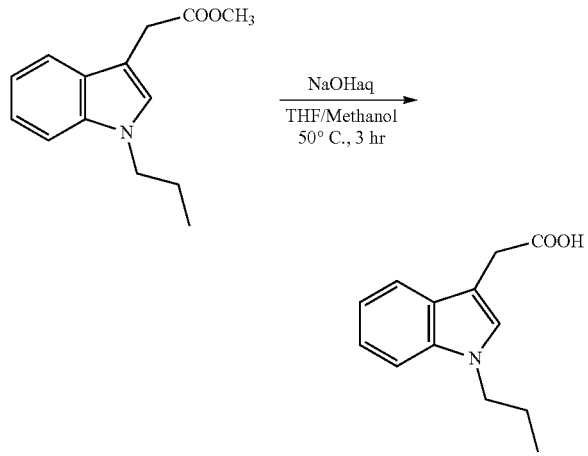

N-Propyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-propyl-3-indoleacetic acid (compound #28) (103 mg, yield: 98%); $^1$H NMR (400 MHz, CDCl$_3$): δ 7.60 (d, J=8.0 Hz, 1H), 7.32 (d, J=8.2 Hz, 1H), 7.21 (dd, J=7.2, 8.0 Hz, 1H), 7.11 (dd, J=7.3, 9.8 Hz, 1H), 7.09 (s, 1H), 4.04 (t, J=7.1, 2H), 3.79 (s, 2H), 1.85 (m, 2H), 0.92 (t, J=7.4 Hz, 3H); $^{13}$C NMR (100 MHz, CDCl$_3$): δ 177.5, 136.2, 127.6, 127.0, 121.6, 119.1, 119.0, 109.5, 106.0, 53.7, 31.7, 23.5, 11.5.

Synthesis of Compound #29

N-Butyl-3-indoleacetic Acid Methyl Ester

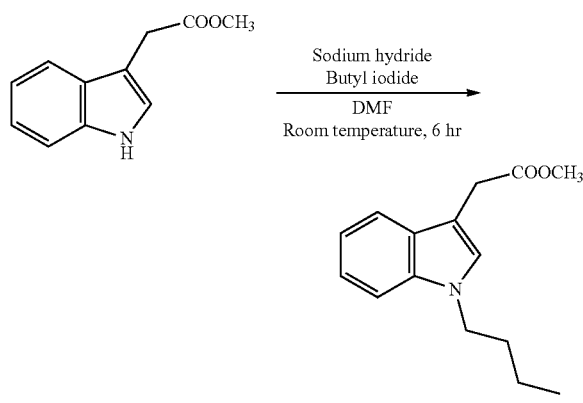

3-Indoleacetic acid methyl ester (200 mg, 1.1 mmol) was dissolved in N,N-dimethylformamide (3 mL). To the solution, sodium hydride (60 mg) was added. To this solution, butyl iodide (290 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-butyl-3-indoleacetic acid methyl ester (137 mg, yield: 53%); $^1$H NMR (400 MHz, CDCl$_3$): δ 7.60 (d, J=7.8 Hz, 1H), 7.32 (d, J=8.2 Hz, 1H), 7.21 (dd, J=8.5, 9.8 Hz, 1H), 7.11 (dd, J=9.7, 7.4 Hz, 1H), 7.08 (s, 1H), 4.08 (t, J=7.1 Hz, 2H), 3.77 (s, 2H), 3.69 (s, 3H), 1.80 (m, 2H), 1.34 (m, 2H), 0.93 (t, J=7.4 Hz, 3H); $^{13}$C NMR (100 MHz, CDCl$_3$): δ 172.6, 136.2, 127.7, 126.7, 121.5, 119.0, 119.0, 109.4, 106.7, 51.9, 46.0, 32.3, 31.1, 20.2, 13.7.

N-Butyl-3-indoleacetic Acid (Compound #29)

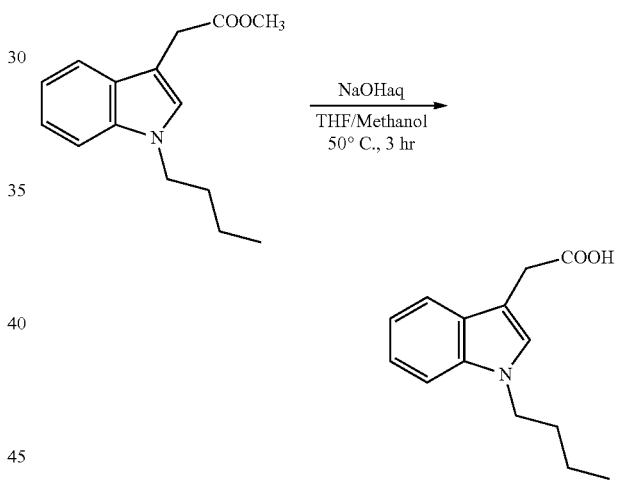

N-Butyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-butyl-3-indoleacetic acid (compound #29) (104 mg, yield: 98%); $^1$H NMR (400 MHz, CDCl$_3$): δ 7.59 (d, J=7.9 Hz, 1H), 7.31 (d, J=8.2 Hz, 1H), 7.20 (dd, J=7.1, 7.9 Hz, 1H), 7.11 (dd, J=7.3, 7.5 Hz, 1H), 7.07 (s, 1H), 4.06 (t, J=7.2 Hz, 2H), 3.78 (s, 2H), 1.79 (m, 2H), 1.33 (m, 2H), 0.92 (t, J=7.4, 3H); $^{13}$C NMR (100 MHz, CDCl$_3$):

δ 178.0, 136.1, 127.6, 126.9, 121.6 119.10, 119.0, 109.5, 106.0, 53.6, 31.7, 29.1, 20.2, 13.7.

Synthesis of Compound #30

N-Hexyl-3-indoleacetic Acid Methyl Ester

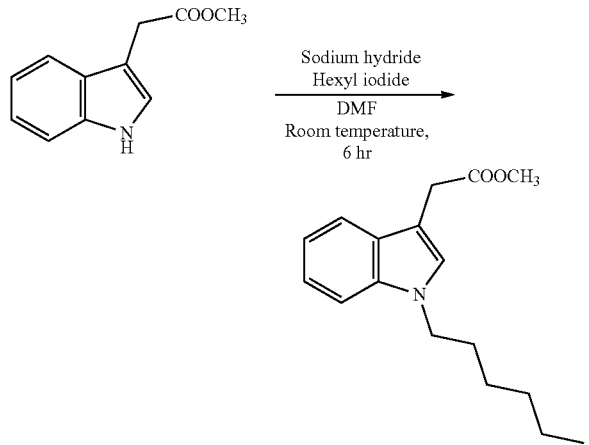

3-Indoleacetic acid methyl ester (200 mg, 1.1 mmol) was dissolved in N,N-dimethylformamide (3 mL). To the solution, sodium hydride (60 mg) was added. To this solution, hexyl iodide (334 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-hexyl-3-indoleacetic acid methyl ester (147 mg, yield: 51%); $^1$H NMR (400 MHz, CDCl$_3$): δ 7.60 (d, J=7.8 Hz, 1H) 7.31, (d, J=8.2 Hz, 1H), 7.20 (ddd, J=8.6, 5.6 Hz, 1H), 7.11 (ddd, J=8.0, 7.3 Hz, 1H), 7.08 (s, 2H), 4.06 (t, J=7.2 Hz, 2H), 3.77 (s, 2H), 3.69 (s, 3H), 1.81 (m, 2H), 1.30 (m, 6H), 0.87 (t, J=6.9 Hz, 3H); $^{13}$C NMR (100 MHz, CDCl$_3$): δ 172.6, 136.1, 127.7, 126.7, 121.5, 119.0, 119.0, 109.4, 106.6, 51.9, 46.3, 31.4, 31.1, 30.2, 22.6, 22.5, 14.0.

N-Hexyl-3-indoleacetic Acid (Compound #30)

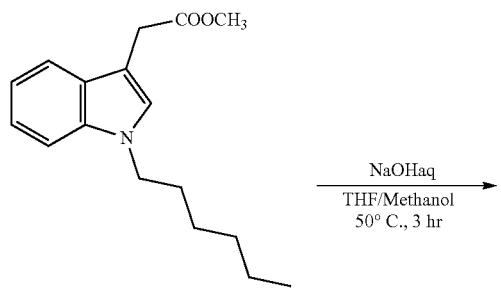

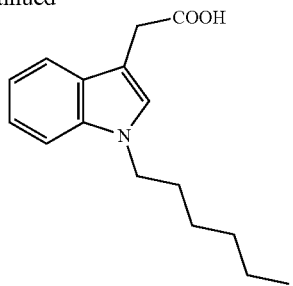

N-Hexyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-hexyl-3-indoleacetic acid (compound #30) (103 mg, yield: 96%); $^1$H NMR (400 MHz, CDCl$_3$): δ 7.59 (d, J=7.9 Hz, 1H), 7.31 (d, J=8.2 Hz, 1H), 7.20 (ddd, J=7.9, 7.3 Hz, 1H), 7.20 (ddd, J=7.4, 7.7 Hz, 1H), 7.07 (1H, s, 1H), 4.05 (t, J=7.2 Hz, 2H), 3.78 (s, 2H), 1.81 (m, 2H), 1.31 (m, 6H), 0.88 (t, J=6.3 Hz, 3H); $^{13}$C NMR (100 MHz, CDCl$_3$): δ 178.0, 136.1, 127.6, 127.6, 121.6, 119.1, 119.0, 109.5, 106.0, 53.7, 31.7, 29.2, 28.9, 27.0, 23.0, 14.02.

Synthesis of Compound #31

N-Heptyl-3-indoleacetic Acid Methyl Ester

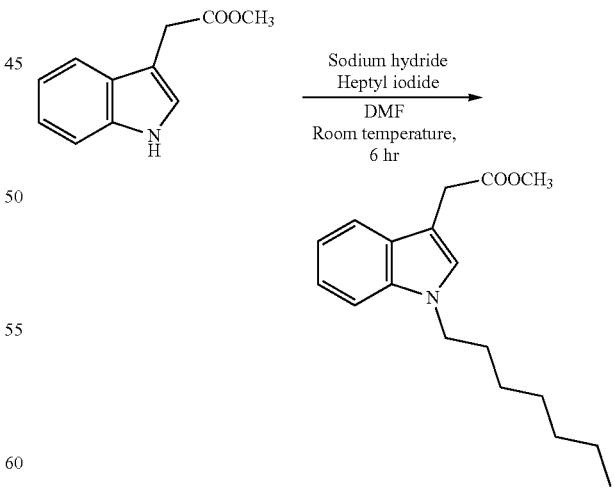

3-Indoleacetic acid methyl ester (200 mg, 1.1 mmol) was dissolved in N,N-dimethylformamide (3 mL). To the solution, sodium hydride (60 mg) was added. To this solution, heptyl iodide (358 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-heptyl-3-indoleacetic acid methyl ester (148 mg, yield: 49%); $^1$H NMR (400 MHz, CDCl$_3$): δ 3.69 (3H, s), 7.60 (1H, d, J=7.8), 7.31 (1H, d, J=8.2) 7.11 (1H, dd, J=8.2, 6.7), 7.08 (1H, s), 4.06 (2H, t, J=7.1), 3.77 (2H, s) 3.59 (1H, dd, J=8.2, 6.7), 1.82 (2H, m), 1.29 (8H, m), 0.87 (3H, t, J=7.1); $^{13}$C NMR (100 MHz, CDCl$_3$): δ 172.57, 136.16, 127.70, 126.66, 121.54, 118.98, 118.98, 109.43, 106.64, 51.89, 46.31, 31.67, 31.11, 30.24, 28.89, 26.96, 22.55, 14.02.

N-Heptyl-3-indoleacetic Acid (Compound #31)

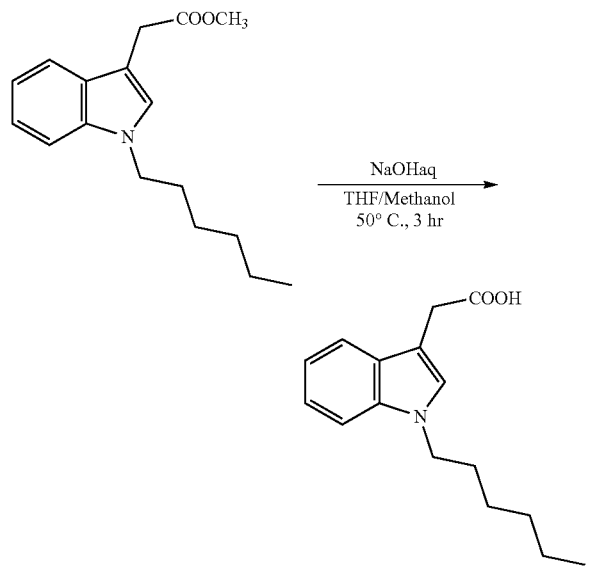

N-Heptyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-heptyl-3-indoleacetic acid (compound #31) (180 mg, yield: 95%); $^1$H NMR (400 MHz, CDCl$_3$): δ 7.59 (1H, d, J=7.96), 7.31 (1H, d, J=8.17), 7.21 (1H, ddd, J=8.49, 6.73), 7.11 (1H, ddd, J=7.21, 7.29), 7.08 (1H, S), 4.06 (2H, t, J=7.25), 3.79 (2H, s) 1.81 (2H, m) 1.29 (8H, m) 0.87 (3H, t, J=6.83); $^{13}$C NMR (100 MHz, CDCl$_3$): δ 177.81, 136.10, 127.55, 126.85, 121.62, 119.11, 118.94, 109.49, 105.91, 53.63, 46.32, 30.99, 29.68, 29.16, 26.64, 22.49, 13.99.

Compounds #33 and 34 were each synthesized with α-(7-hydroxy-1-naphthalenyl)-acetic acid ethyl ester as a key intermediate. The α-(7-hydroxy-1-naphthalenyl)-acetic acid ethyl ester was synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011.

Synthesis of Compound #33

α-(7-Butoxy-1-naphthalenyl)-acetic Acid Ethyl Ester

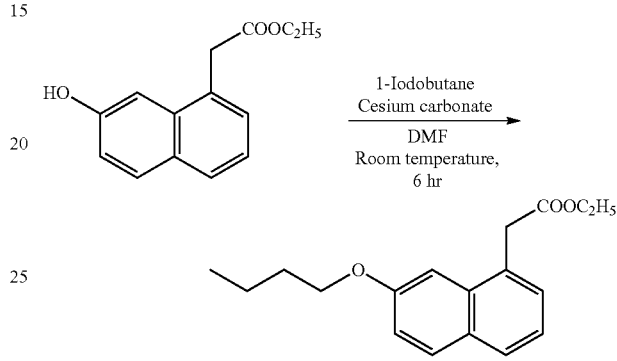

α-(7-Hydroxy-1-naphthalenyl)-acetic acid ethyl ester (90 mg, 0.39 mmol) was dissolved in N,N-dimethylformamide (5 ml). To this solution, 1-iodobutane (107 mg, 0.58 mmol) was added dropwise, then cesium carbonate (127 mg, 0.39 mmol) was added, and the mixture was stirred at room temperature for 6 hours. After the reaction was confirmed by TLC to be complete, water (5 ml) was added to the reaction solution, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain α-(7-butoxy-1-naphthalenyl)-acetic acid ethyl ester as a colorless oil (92 mg, yield: 83%); $^1$H NMR (400 MHz, CDCl$_3$): δ 7.71 (d, J=8.9 Hz, 1H), 7.35 (d, J=6.9 Hz, 1H), 7.67 (d, J=8.1 Hz, 1H), 7.27 (d, J=2.3 Hz, 1H), 7.25 (dd, J=8.1, 6.9 Hz, 1H), 7.14 (q, J=8.9, 2.3 Hz, 1H), 4.12 (q, J=7.1 Hz, 2H), 4.07 (t, J=6.6 Hz, 2H), 3.97 (s, 2H), 1.82 (m, 2H), 1.53 (m, 2H), 1.19 (t, J=7.1 Hz, 3H), 0.96 (t, J=7.5 Hz, 3H); $^{13}$C NMR (100 MHz, CDCl$_3$): δ 171.5, 157.4, 133.2, 130.0, 129.3, 129.1, 128.3, 127.6, 123.0, 118.5, 103.2, 67.6, 60.8, 39.5, 31.2, 19.2, 14.1, 13.8; IR (neat): 2958, 1733, 1510, 1459, 1210, 1156 cm$^{-1}$; HREI-MS found m/z 286.1556 [M]$^+$, calcd for 286.1569 ($C_{18}H_{22}O_3$).

α-(7-Butoxy-1-naphthalenyl)-acetic Acid (Compound #33)

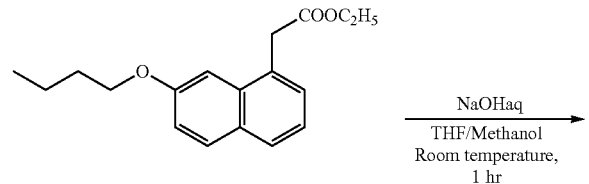

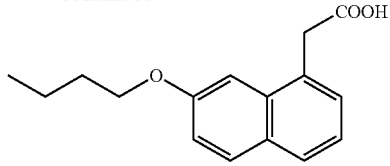

α-(7-Butoxy-1-naphthalenyl)-acetic acid ethyl ester (75 mg, 0.26 mmol) was dissolved in a mixed solution of tetrahydrofuran:methanol:2 M aqueous sodium hydroxide solution=2:2:1 (1.5 ml), and the solution was stirred at room temperature for 1 hour. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-(7-butoxy-1-naphthalenyl)-acetic acid (compound #33) (67 mg, yield: 98%); Melting point: 102 to 104° C.; $^1$H NMR (400 MHz, CDCl$_3$): δ 7.75 (d, J=8.9 Hz, 1H), 7.71 (d, J=8.1 Hz, 1H), 7.34 (d, J=6.9 Hz, 1H), 7.26 (dd, J=8.1, 6.9 Hz, 1H), 7.23 (d, J=2.0 Hz, 1H), 7.16 (q, J=8.9, 2.0 Hz, 1H), 4.05 (t, J=6.5 Hz, 2H), 4.00 (s, 2H), 1.51 (m, 2H), 1.80 (m, 2H), 0.98 (t, J=7.4 Hz, 3H); $^{13}$C NMR (100 MHz, CDCl$_3$): δ 177.6, 157.6, 133.2, 130.2, 129.1, 128.6, 127.9 (2C), 123.0, 118.7, 103.1, 67.7, 39.2, 31.2, 19.3, 13.8; IR (neat): 3021, 2931, 1699, 1457, 1138 cm$^{-1}$; HREI-MS found m/z 258.1268 [M]$^+$, calcd for 258.1256 (C$_{16}$H$_{18}$O$_3$).

Synthesis of Compound #34

α-(7-Pentoxy-1-naphthalenyl)-acetic Acid Ethyl Ester

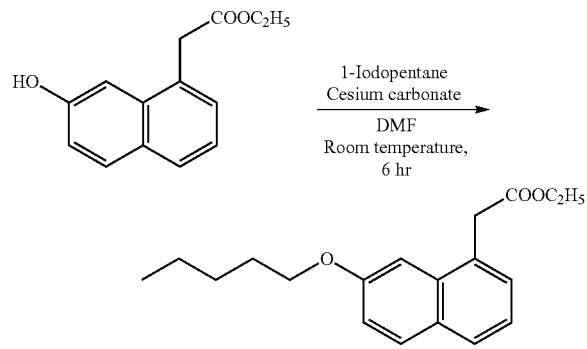

α-(7-Hydroxy-1-naphthalenyl)-acetic acid ethyl ester (90 mg, 0.39 mmol) was dissolved in N,N-dimethylformamide (5 ml). To this solution, 1-iodopentane (116 mg, 0.58 mmol) was added dropwise, then cesium carbonate (127 mg, 0.39 mmol) was added, and the mixture was stirred at room temperature for 6 hours. After the reaction was confirmed by TLC to be complete, water (5 ml) was added to the reaction solution, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain α-(7-pentoxy-1-naphthalenyl)-acetic acid ethyl ester as a colorless oil (103 mg, yield: 88%): $^1$H NMR (400 MHz, CDCl$_3$): δ 1.00 (t, J=7.2 Hz, 3H), 1.26 (t, J=7.1 Hz, 3H), 1.48 (m, 2H), 1.55 (m, 2H), 1.91 (m, 2H), 4.03 (s, 2H), 4.13 (t, J=6.5 Hz, 2H), 4.19 (q, J=7.1 Hz, 2H), 7.20 (dd, J=8.9, 2.5 Hz, 1H), 7.31 (dd, J=8.1, 7.0 Hz, 1H), 7.33 (d, J=2.5 Hz, 1H), 7.41 (d, J=7.0 Hz, 1H), 7.74 (d, J=8.1 Hz, 1H), 7.78 (d, J=8.9 Hz, 1H); $^{13}$C NMR (100 MHz, CDCl$_3$): δ 171.5, 157.4, 133.2, 130.0, 129.3, 129.1, 128.4, 127.6, 123.0, 118.5, 103.2, 67.8, 60.8, 39.6, 28.9, 28.2, 22.4, 14.1, 14.0; IR (neat): 2969, 1734, 1509, 1459, 1160 cm$^{-1}$; HREI-MS found m/z 300.1727 [M]$^+$, calcd for 300. 1725 (C$_{19}$H$_{24}$O$_3$).

α-(7-Pentoxy-1-naphthalenyl)-acetic Acid (Compound #34)

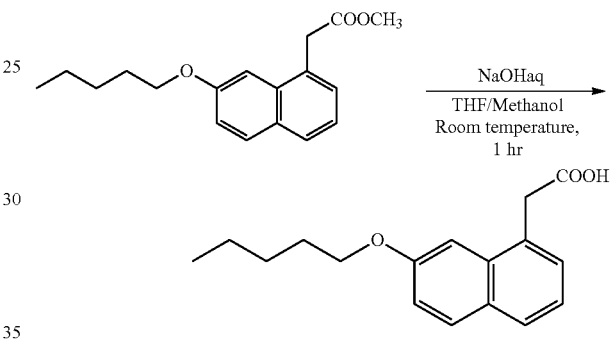

α-(7-Pentoxy-1-naphthalenyl)-acetic acid ethyl ester (90 mg, 0.30 mmol) was dissolved in a mixed solution of tetrahydrofuran:methanol:2 M aqueous sodium hydroxide solution=2:2:1 (1.5 ml), and the solution was stirred at room temperature for 1 hour. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (chloroform:methanol=6:1) to obtain α-(7-pentoxy-1-naphthalenyl)-acetic acid (compound #34) (75 mg, yield: 92%); Melting point: 104 to 106° C.; $^1$H NMR (400 MHz, CDCl$_3$): δ 7.71 (d, J=8.1 Hz, 1H), 7.39 (d, J=6.9 Hz, 1H), 7.26 (t, J=8.1, 6.9 Hz, 1H), 7.21 (d, J=2.1 Hz, 1H), 7.15 (dd, J=8.9, 2.1 Hz, 1H), 4.03 (t, J=6.5 Hz, 2H), 4.00 (s, 2H), 3.87 (d, J=8.9 Hz, 1H), 1.82 (m, 2H), 1.45 (m, 2H), 1.39 (m, 2H), 0.93 (t, J=7.1 Hz, 3H); $^{13}$C NMR (100 MHz, CDCl$_3$): δ 177.6, 157.6, 133.2, 130.2, 129.1, 128.6, 128.4, 128.0, 123.0, 118.7, 103.1, 68.0, 39.1, 28.9, 28.2, 22.5, 14.0; IR (neat): 3014, 2945, 1689, 1463, 1169 cm$^{-1}$; HREI-MS found m/z 272.1378 [M]$^+$, calcd for 272.1412 (C$_{17}$H$_{20}$O$_3$).

Compounds #35 to 37 were each synthesized with 5-hydroxy-3-indoleacetic acid methyl ester as a key intermediate.

5-Hydroxy-3-indoleacetic Acid Methyl Ester

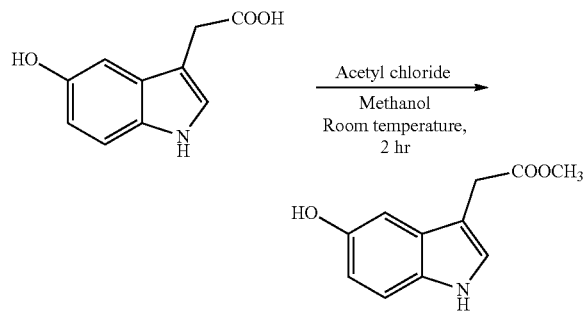

5-Hydroxy-3-indoleacetic acid (1.00 g) was dissolved in methanol (25 ml). To the solution, acetyl chloride (1.0 ml) was slowly added dropwise, and the mixture was stirred at room temperature for 2 hours. After the reaction was confirmed by TLC to be complete, the reaction was terminated by the addition of a saturated aqueous solution of sodium bicarbonate, and the solvent was distilled off under reduced pressure. Then, water (20 ml) was added to the residue, followed by extraction with ethyl acetate (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=3:2) to obtain 5-hydroxy-3-indoleacetic acid methyl ester (1.05 g, yield: 98%); $^1$H NMR (400 MHz, CDCl$_3$): δ 7.20 (s, J=8.7 Hz, 1H), 7.13 (d, J=2.4 Hz, 1H), 7.00 (d, J=2.4 Hz, 1H), 6.78 (dd, J=8.8, 2.4 Hz, 1H), 3.72 (s, 2H), 3.70 (s, 3H); $^{13}$C NMR (100 MHz, CDCl$_3$): δ 172.6, 149.6, 131.4, 127.9, 124.2, 112.1, 111.9, 103.4, 107.8, 52.0, 31.2; IR (neat): 3411, 3000, 2952, 1728, 1459, 1459, 1154 cm$^{-1}$; EI-MS m/z [M]$^+$205, 146; HREI-MS found m/z 205.0761 [M]$^+$, calcd for 205.0739 ($C_{11}H_{11}NO_3$).

Synthesis of Compound #35

5-(3,5-Dimethoxybenzyloxy)-3-indoleacetic Acid Methyl Ester

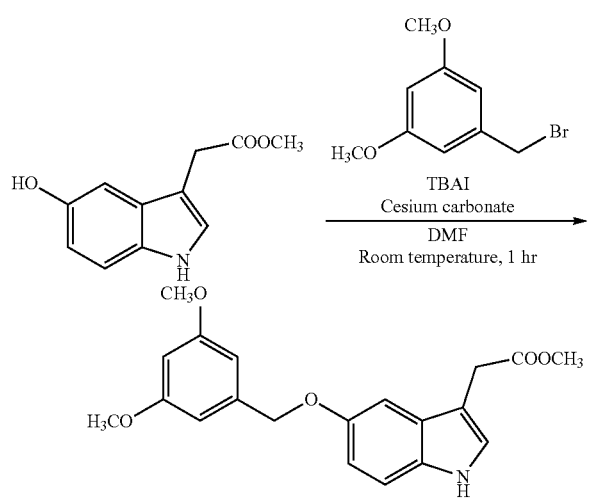

5-Hydroxy-3-indoleacetic acid methyl ester (42.9 mg, 0.21 mmol) was dissolved in N,N-dimethylformamide (DMF). To this solution, 3,5-dimethoxybenzyl bromide (82.2 mg, 0.36 mmol) was added dropwise, then tetra-N-butylammonium iodide (83.0 mg, 2.00 mmol) and cesium carbonate (136.37 mg, 0.42 mmol) put aside in another container were added, and the mixture was stirred at room temperature for 1 hour. After the reaction was confirmed by TLC to be complete, the reaction was terminated by the addition of an aqueous sodium bicarbonate solution, followed by extraction with ethyl acetate (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=3:2) to obtain 5-(3,5-dimethoxybenzyloxy)-3-indoleacetic acid methyl ester (81.5 mg, yield: 94%); $^1$H NMR (400 MHz, CDCl$_3$): δ 7.17 (d, J=2.2 Hz, 1H), 7.12 (d, J=8.7 Hz, 1H), 7.04 (s, 2H), 6.92 (dd, J=8.7, 2.2 Hz, 1H), 6.64 (d, J=2.2, 2H), 6.41 (t, J=2.2 Hz, 1H), 5.13 (s, 2H), 3.78 (s, 6H), 3.72 (s, 2H), 3.67 (s, 3H); $^{13}$C NMR (100 MHz, CDCl$_3$): δ 172.5, 160.9 (2C), 153.2, 140.0, 131.4, 124.0, 127.5, 113.0, 111.9, 107.9, 105.2 (2C), 102.2, 99.8, 70.8, 55.3 (2C), 51.9, 31.2; IR (neat): 3396, 2948, 1734, 1449, 1159 cm$^{-1}$.

5-(3,5-Dimethoxybenzyloxy)-3-indoleacetic Acid (Compound #35)

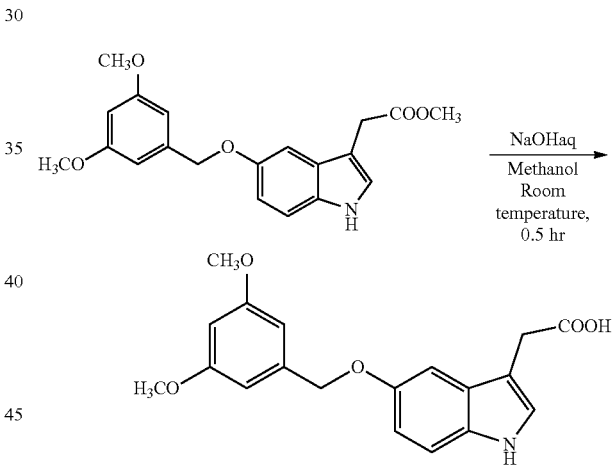

5-(3,5-Dimethoxybenzyloxy)-3-indoleacetic acid methyl ester (81.5 mg, 0.23 mmol) was dissolved in tetrahydrofuran (0.5 ml). To this solution, methanol (0.5 ml) and a 2 N aqueous sodium hydroxide solution (0.25 ml) were added, and the mixture was stirred at room temperature for 0.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain 5-(3,5-dimethoxybenzyloxy)-3-indoleacetic acid (compound #35) (55.2 mg, yield: 100%); Melting point: 146.1 to 148.6° C.; $^1$H NMR (400 MHz, CDCl$_3$): δ 7.19 (d, J=8.8 Hz, 1H), 7.12 (d, J=2.2 Hz, 1H), 7.06 (s, 1H), 6.92 (dd, J=8.8, 2.2 Hz, 1H), 6.68 (d, J=2.2 Hz, 2H), 6.40 (t, J=2.2 Hz, 1H), 5.01 (S, 2H), 3.77 (S, 6H), 3.73 (s, 2H); $^{13}$C NMR (100 MHz, CDCl$_3$): δ 177.5, 160.8 (2C), 153.3, 140.0, 131.4, 127.5, 124.1, 113.1, 112.0, 107.4, 105.3 (2C), 102.2, 99.9, 70.9, 55.3 (2C), 31.1; IR (neat): 3406, 2957, 2926, 1702, 1458, 1155 cm$^{-1}$ Synthesis of Compound #36

5-Methoxy-3-indoleacetic Acid Methyl Ester

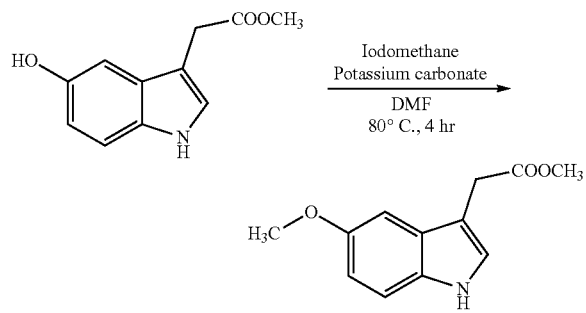

5-Hydroxy-3-indoleacetic acid methyl ester (99.3 mg, 0.48 mmol) was dissolved in N,N-dimethylformamide (2 ml). To this solution, iodomethane (206.2 mg, 1.45 mmol) was added dropwise, then potassium carbonate (200.8 mg, 1.45 mmol) put aside in another container was added, and the mixture was stirred overnight at room temperature and subsequently stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-methoxy-3-indoleacetic acid methyl ester (58.6 mg, yield: 55.2%); $^1$H NMR (400 MHz, CDCl$_3$): δ 7.22 (1H, d. J=8.8), 7.11 (d, J=2.3 Hz, 1H), 7.05 (d, J=1.3 Hz, 1H), 6.93 (dd, J=8.8, 2.3 Hz, 1H), 3.70 (s, 3H), 3.85 (s, 3H), 3.74 (s, 2H); $^{13}$C NMR (100 MHz, CDCl$_3$): δ 172.5, 154.2, 131.2, 127.6, 123.8, 112.5, 111.9, 108.1, 100.6, 55.9, 51.9, 31.2; IR (neat): 3403, 2951, 1729, 1486, 1213, 1154 cm$^{-1}$; EI-MS m/z [M]$^+$219, 160; HREI-MS found m/z 219.0886 [M]$^+$, calcd for 219.0895 (C$_{12}$H$_{13}$NO$_3$).

5-Methoxy-3-indoleacetic Acid (Compound #36)

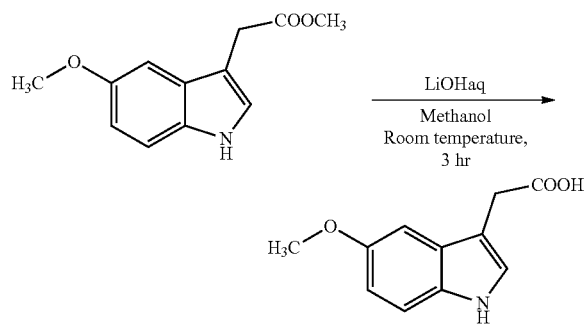

5-Methoxy-3-indoleacetic acid methyl ester (60.0 mg, 0.27 mmol) was dissolved in methanol (2 ml). To the solution, lithium hydroxide (19.7 mg, 0.82 mmol) was added, and the mixture was stirred at room temperature for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-methoxy-3-indoleacetic acid (compound #36) (15.3 mg, yield: 27.2%); Melting point: 147.0 to 149.8° C.; $^1$H NMR (400 MHz, CDCl$_3$): δ 7.28 (d, J=8.8 Hz, 1H), 7.26 (s, 1H), 7.11 (d, J=2.3 Hz, 1H), 6.77 (dd, J=8.8, 2.3 Hz, 1H), 3.80 (s, 3H), 3.71 (s, 1H); $^{13}$C NMR (100 MHz, CDCl$_3$): δ 173.3, 154.8, 132.6, 128.9, 125.2, 112.7, 112.4, 108.8, 101.4, 55.8, 31.5; IR (neat): 3359, 2996, 2851, 1705, 1456, 1137 cm$^{-1}$; EI-MS m/z [M]$^+$205 (75%), 160; HREI-MS found m/z 205.0737 [M]$^+$, calcd for 205.0739 (C$_{11}$H$_{11}$NO$_3$).

Synthesis of Compound #37

5-Ethoxy-3-indoleacetic Acid Methyl Ester

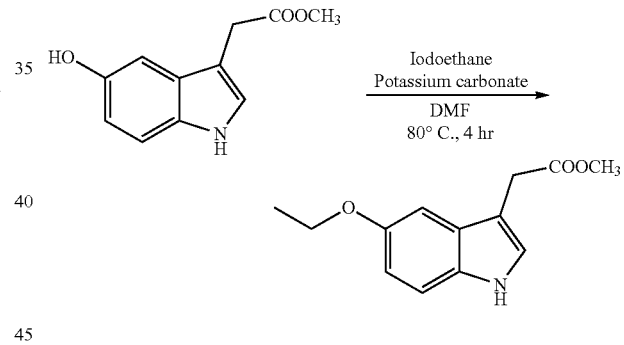

5-Hydroxy-3-indoleacetic acid methyl ester (109.0 mg, 0.53 mmol) was dissolved in N,N-dimethylformamide (2 ml). To this solution, iodoethane (248.74 mg, 1.60 mmol) was added dropwise, then potassium carbonate (220.5 mg, 1.60 mmol) put aside in another container was added, and the mixture was stirred at room temperature for 2 hours and stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-ethoxy-3-indoleacetic acid methyl ester (100.7 mg, yield: 81.2%); $^1$H NMR (400 MHz, CDCl$_3$): δ 7.86 (q, J=7.0 Hz, 2H), 7.23 (d, J=8.8 Hz, 1H), 7.05 (d, J=2.3 Hz, 1H), 7.12 (d, J=2.0 Hz, 1H), 6.87 (dd, J=8.8, 2.3 Hz, 1H), 3.75 (s, 2H), 3.70 (s, 3H), 1.45 (t, J=7.0 Hz, 3H); $^{13}$C NMR (100 MHz, CDCl$_3$): δ 172.5, 153.4, 131.2, 127.6, 123.7, 113.0, 111.8, 108.1, 101.8, 64.2, 52.0, 31.2, 15.0; IR (neat): 3404, 2978, 1729, 1474, 1211, 1154 cm$^{-1}$; HREI-MS found m/z 233.1034 [M]$^+$, calcd for 233.1052 ($C_{13}H_{15}NO_3$).

5-Ethoxy-3-indoleacetic Acid (Compound #37)

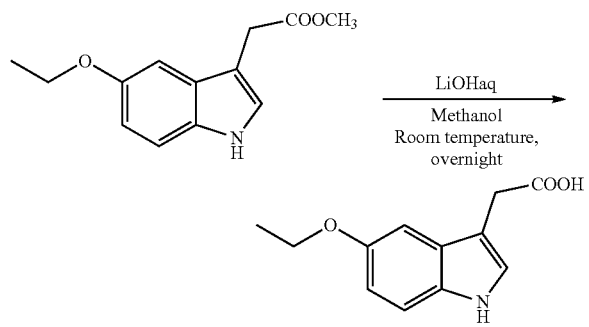

5-Ethoxy-3-indoleacetic acid methyl ester (90.2 mg, 0.27 mmol) was dissolved in methanol (4 ml). To the solution, lithium hydroxide (13.9 mg, 0.58 mmol) was added, and the mixture was stirred overnight at room temperature. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-ethoxy-3-indoleacetic acid (compound #37) (83.8 mg, yield: 98.9%); Melting point: 86.0 to 92.7° C.; $^1$H NMR (400 MHz, CDCl$_3$): δ 7.23 (d, J=8.8 Hz, 1H), 7.12 (d, J=1.9 Hz, 1H), 7.04 (d, J=2.3 Hz, 1H), 6.86 (dd. J=8.8, 2.3 Hz, 1H), 4.09 (q, J=7.0 Hz, 2H), 3.80 (s, 2H), 1.42 (t, J=7.0 Hz, 3H); $^{13}$C NMR (100 MHz, CDCl$_3$): δ 177.4, 153.5, 131.2, 127.5, 124.0, 113.2, 111.9, 107.7, 101.7, 64.2, 31.1, 15.0; IR (neat): 3354, 3066, 2930, 1695, 1457, 1112 cm$^{-1}$; EI-MS m/z [M]+219, 205 (40%), 190, 174, 162 (70%), 160 (50%); HREI-MS found m/z 219.0886 [M]$^+$, calcd for 219.0895 ($C_{12}H_{13}NO_3$).

Synthesis of Compound #38

5-(1-Propoxy)-3-indoleacetic Acid Methyl Ester

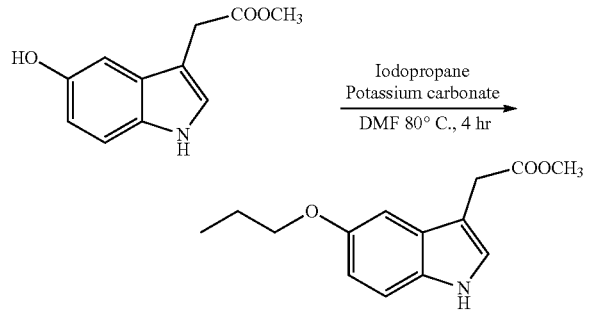

5-Hydroxy-3-indoleacetic acid methyl ester (108.4 mg, 0.53 mmol) was dissolved in N,N-dimethylformamide (2 ml). To this solution, iodopropane was added dropwise, then potassium carbonate (219.3 mg, 1.59 mmol) put aside in another container was added, and the mixture was stirred at room temperature for 2 hours and stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-(1-propoxy)-3-indoleacetic acid methyl ester (78.6 mg, yield: 60.1%); Melting point: 38.6 to 41.0° C.; $^1$H NMR (400 MHz, CDCl$_3$): δ 7.21 (d, J=8.8 Hz, 1H), 7.10 (d, J=2.3 Hz, 1H), 7.05 (d, J=2.3 Hz, 1H), 6.86 (dd, J=8.8, 2.3 Hz, 1H), 4.01 (t, J=6.7 Hz, 2H), 3.74 (s, 2H), 3.70 (s, 3H), 1.82 (m, 2H), 1.07 (t, J=6.7 Hz, 3H); $^{13}$C NMR (100 MHz, CDCl$_3$): δ 172.5, 153.6, 131.2, 127.6, 123.7, 113.0, 111.8, 108.0, 101.7, 70.4, 52.0, 31.2, 22.8, 10.6; IR (neat): 3355, 3061, 2961, 1695, 1457, 1126 cm$^{-1}$; EI-MS m/z [M]$^+$247 (70%), 188 (30%), 149, 131 (75%); HREI-MS found m/z 247.1225 [M]$^+$, calcd for 247.1208 ($C_{14}H_{17}NO_3$).

5-(1-Propoxy)-3-indoleacetic Acid (Compound #38)

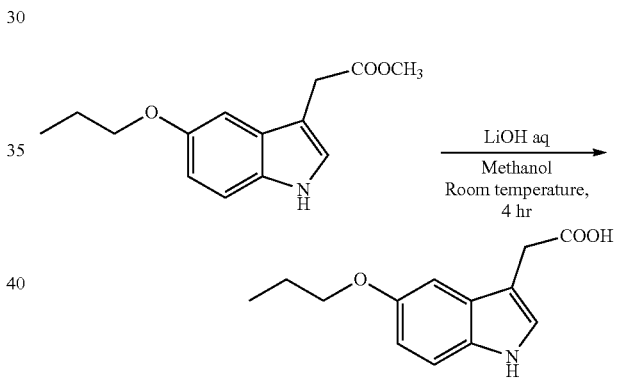

5-(1-Propoxy)-3-indoleacetic acid methyl ester (64.3 mg, 0.26 mmol) was dissolved in methanol (2 ml). To the solution, lithium hydroxide (9.35 mg, 0.39 mmol) was added, and the mixture was stirred at room temperature for 4 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-(1-propoxy)-3-indoleacetic acid (compound #38) (59.3 mg, yield: 97.7%); Melting point: 133.6 to 136.8° C.; $^1$H NMR (400 MHz, CDCl$_3$): δ 7.23 (d, J=8.8 Hz, 1H), 7.13 (s, 1H), 7.04 (d, J=2.2 Hz, 1H), 6.87 (dd, J=8.1, 2.2 Hz, 1H), 3.96 (t, J=6.6 Hz, 2H), 3.76 (s, 3H), 1.82 (m, 2H), 1.05 (t. J=7.4 Hz, 3H); $^{13}$C NMR (100 MHz, CDCl$_3$): δ 177.4, 153.7, 131.2, 127.5, 123.9, 113.2, 111.9, 107.5, 101.7, 70.4, 31.0, 22.8, 10.6, 10.6; IR (neat): 3407, 2954, 1728, 1456, 1213, 1160 cm$^{-1}$; EI-MS m/z [M]$^+$233, 191 (50%); HREI-MS found m/z 233.1043 [M]$^+$, calcd for 233.1052 ($C_{12}H_{15}NO_3$).

Synthesis of Compound #39

5-(1-Butoxy)-3-indoleacetic Acid Methyl Ester

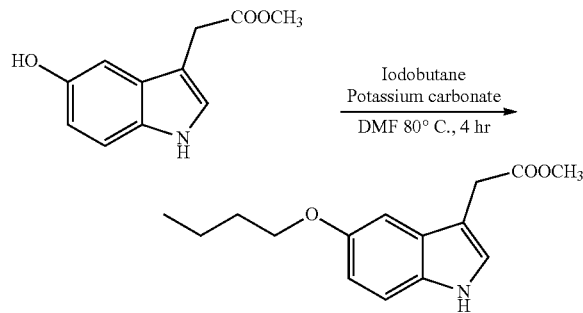

5-Hydroxy-3-indoleacetic acid methyl ester (108.4 mg, 0.53 mmol) was dissolved in N,N-dimethylformamide (2 ml). To this solution, iodobutane was added dropwise, then potassium carbonate (184.2 mg, 1.33 mmol) put aside in another container was added, and the mixture was stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-(1-butoxy)-3-indoleacetic acid methyl ester (140.2 mg, yield: 80.5%); $^1$H NMR (400 MHz, CDCl$_3$): δ 7.21 (d, J=7.2 Hz, 1H), 7.10 (d, J=2.3 Hz, 1H), 7.05 (d, J=2.3 Hz, 1H), 6.86 (dd, J=8.8, 2.3 Hz, 1H), 4.01 (t, J=6.5 Hz, 2H), 3.74 (s, 2H), 3.70 (s, 3H), 1.82 (m, 2H), 1.52 (m, 2H), 0.98 (t, J=7.4 Hz, 3H); $^{13}$C NMR (100 MHz, CDCl$_3$): δ 172.5, 153.6, 131.2, 127.6, 123.7, 113.0, 111.8, 108.0, 101.7, 68.5, 51.9, 31.9, 31.2, 19.3, 13.9; IR (neat): 3355, 2957, 1694, 1459, 1127 cm$^{-1}$; HREI-MS found m/z 261.137 [M]$^+$, calcd for 261.1365 ($C_{15}H_{19}NO_3$).

5-(1-Butoxy)-3-indoleacetic Acid (Compound #39)

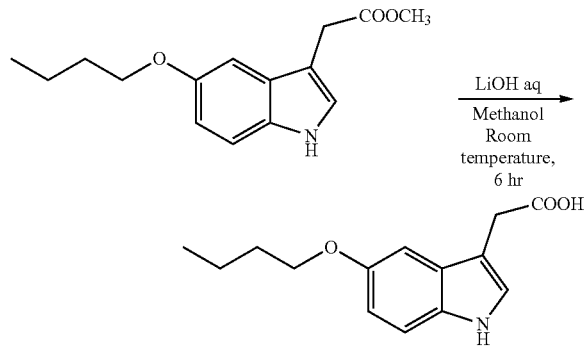

5-(1-Butoxy)-3-indoleacetic acid methyl ester (91.0 mg, 0.35 mmol) was dissolved in methanol (2 ml). To the solution, lithium hydroxide (12.5 mg, 0.52 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-(1-butoxy)-3-indoleacetic acid (compound #39) (43.8 mg, yield: 51.0%); Melting point: 137.8 to 141.1° C.; $^1$H NMR (400 MHz, CDCl$_3$): δ 7.24 (d, J=8.8 Hz, 1H), 7.14 (s, 1H), 7.04 (d, J=2.0 Hz, 1H), 6.87 (dd, J=8.8, 2.0 Hz, 1H), 4.01 (t, J=6.6 Hz, 2H), 3.76 (s, 2H), 1.78 (m, 2H), 1.05 (t. J=7.4 Hz, 3H); $^{13}$C NMR (100 MHz, CDCl$_3$): δ 173.3, 153.8, 131.2, 123.9, 113.2, 111.6, 107.5, 101.6, 31.6, 29.7, 19.3, 13.9; IR (neat): 3407, 2954, 1728, 1456, 1213, 1160 cm$^{-1}$; EI-MS m/z [M]$^+$247, 191 (60%); HREI-MS found m/z 247.1189 [M]$^+$, calcd for 247.1208 ($C_{14}H_{17}NO_3$).

Synthesis of Compound of Formula (1)

Synthesis of 4-(2,4-difluorophenyl)-2-(6-fluoro-1H-indol-3-yl)-4-oxo-butanoic Acid (Compound (4-1))

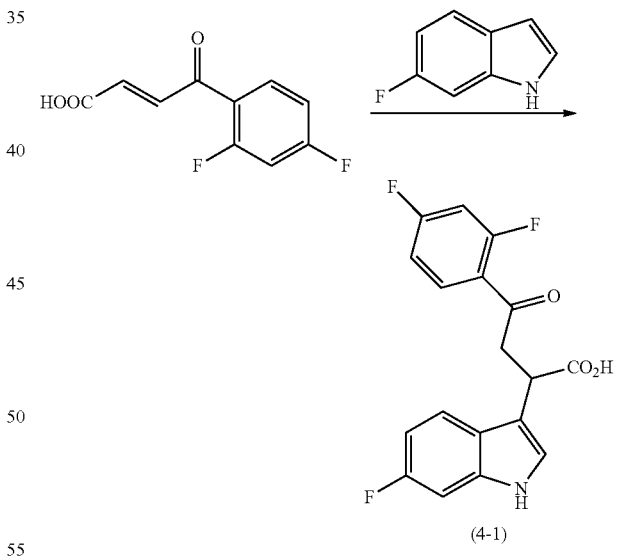

In a 50-mL round-bottomed flask, 6-fluoroindole (485 mg, 3.59 mmol) was added and (E)-4-(2,4-difluorophenyl)-4-oxo-2-butenoic acid (508 mg, 2.39 mmol) was dissolved in benzene (20 mL) and the mixture was heated at 80° C. for 7 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was purified using silica gel column chromatography (hexane:acetone=2:1) to obtain 4-(2,4-Difluorophenyl)-2-(6-fluoro-1H-indol-3-yl)-4-oxo-butanoic acid (433 mg, yield: 52%) as a colorless crystal.

Melting point: 210 to 214° C.;

$^1$H-NMR (400 MHz, CDCl$_3$) δ 10.31 (s, 1H), 8.01 (m, 1H), 7.47 (dd, J=8.8, 5.2, 1H), 7.34 (d, J=2.0, 2H), 7.12-7.20 (m, 3H), 6.92 (td, J=9.6, 2.4, 1H), 4.54 (dd, J=10.4, 4.0, 1H), 4.01 (ddd, J=18.8, 10.8, 3.2, 1H), 3.38 (td, J=18.8, 3.2, 1H); $^{13}$C-NMR (100 MHz, CDCl$_3$) δ 195.18, 174.85, 166.28 $J_{C-F}$(dd, 254, 13 Hz), 163.42 $J_{C-F}$ (dd, 254, 13 Hz), 161.74, 159.4, 137.54 $J_{C-F}$ (d, 13 Hz), 133.47 $J_{C-F}$ (dd, 11.3 Hz), 123.35 $J_{C-F}$ (d, 4 Hz), 123.02 $J_{C-F}$ (dd, 13, 4 Hz), 120.97 $J_{C-F}$ (d, 11 Hz), 113.51, 112.94 $J_{C-F}$ (dd, 10, 2 Hz), 108.27 $J_{C-F}$ (d, 24 Hz), 105.59 $J_{C-F}$ (t, 27 Hz), 98.27 $J_{C-F}$ (d, 26 Hz), 46.68 $J_{C-F}$ (d, 7 Hz), 38.47;

FAB-MS m/z=348 [M+H]$^+$

Synthesis of 4-(2,4-difluorophenyl)-2-(5-fluoro-1H-indol-3-yl)-4-oxo-butanoic Acid (Compound (3-1))

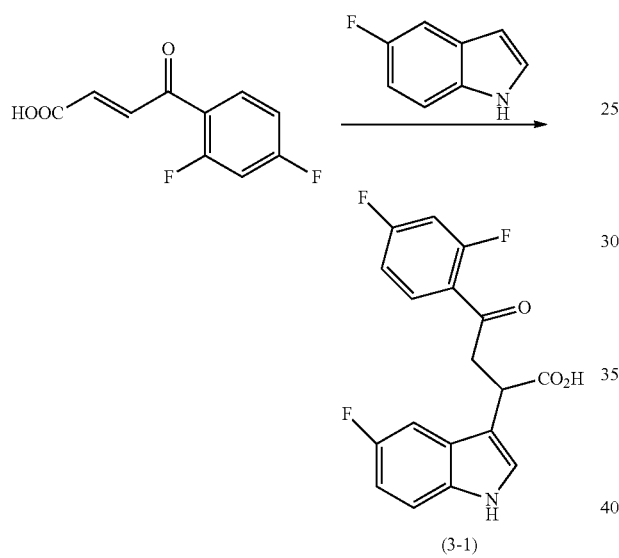

(3-1)

In a 50-mL round-bottomed flask, 5-fluoroindole (925 mg, 6.85 mmol) was added and (E)-4-(2,4-difluorophenyl)-4-oxo-2-butenoic acid (969 mg, 4.57 mmol) was dissolved in benzene (20 mL) and the mixture was heated at 80° C. for 11 hours to reflux. Distilled water (50 mL) was added to the reaction mixture, and extracted twice with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from chloroform and ethyl acetate to obtain 4-(2,4-difluorophenyl)-2-(5-fluoro-1H-indol-3-yl)-4-oxo-butanoic acid (1122 mg, yield: 71%) as a colorless crystal.

Melting point: 207 to 208° C.;

$^1$H-NMR (400 MHz, acetone-d$_6$) δ 10.34 (s, 1H), 8.02 (m, 1H), 7.47 (dd, J=10.4, 2.8, 1H), 7.39-7.43 (m, 2H), 7.13-7.21 (m, 2H), 6.93 (td, J=9.2, 2.8, 1H), 4.52 (dd, J=10.4, 3.6, 1H), 4.03 (ddd, 18.4, 10.8, 3.6, 1H), 3.40 (td, 18.4, 3.6, 1H); $^{13}$C-NMR (100 MHz, acetone-d$_6$) δ 195.17, 174.86, 166.52 $J_{C-F}$ (dd, 254, 13 Hz), 163.58 $J_{C-F}$ (dd, 254, 13 Hz), 159.52, 157.21, 134.25, 133.46 $J_{C-F}$ (dd, 11, 4 Hz), 127.66 $J_{C-F}$ (d, 11 Hz), 123.01 $J_{C-F}$ (dd, 10, 4 Hz), 113.42 $J_{C-F}$ (d, 5 Hz), 113.28 $J_{C-F}$(d, 10 Hz), 113.51 $J_{C-F}$ (dd, 21, 4 Hz), 110.56 $J_{C-F}$(d, 27 Hz), 105.61 $J_{C-F}$ (t, 27 Hz), 104.65 $J_{C-F}$ (d, 24 Hz), 46.68 $J_{C-F}$ (d, 8 Hz), 38.48;

FAB-MS m/z=348 [M+H]$^+$

Synthesis of 2-(7-chloro-1H-indol-3-yl)-4-(2,4-difluorophenyl)-4-oxo-butanoic Acid (Compound (5-1))

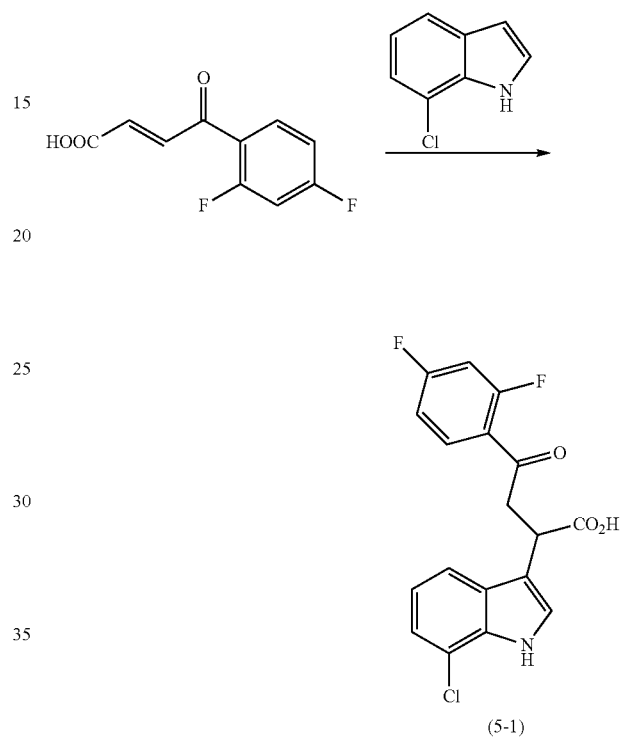

(5-1)

In a 50-mL round-bottomed flask, 7-chloroindole (1094 mg, 5.16 mmol) was added and (E)-4-(2,4-difluorophenyl)-4-oxo-2-butenoic acid (935 mg, 4.41 mmol) was dissolved in benzene (20 mL) and the mixture was heated at 80° C. for 10 hours to reflux. Distilled water (50 mL) was added to the reaction mixture, and extracted twice with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 2-(7-chloro-1H-indol-3-yl)-4-(2,4-difluorophenyl)-4-oxo-butanoic acid (1017 mg, yield: 54%) as a colorless crystal.

Melting point: 225 to 227° C.;

$^1$H-NMR (400 MHz, acetone-d$_6$) δ 10.55 (s, 1H), 8.01 (m, 1H), 7.75 (d, J=8.4, 1H), 7.45 (d, J=2.8, 1H), 7.06-7.14 (m, 4H), 7.08 (t. J=7.6, 1H), 4.57 (dd, J=10.4, 3.6, 1H), 4.03 (ddd, 18.4, 10.8, 3.6, 1H), 3.41 (td, 18.4, 3.6, 1H);

$^{13}$C-NMR (100 MHz, acetone-d$_6$) δ 195.06, 74.67, 166.53, $J_{C-F}$ (dd, 252, 12 Hz), 163.63 $J_{C-F}$ (dd, 252, 12 Hz), 134.45, 133.46 $J_{C-F}$ (dd, 11, 5 Hz), 129.25, 124.97, 122.98 $J_{C-F}$ (dd, 13, 4 Hz), 121.91, 120.84, 119.03, 117.22, 114.73, 112.99 $J_{C-F}$ (dd, 21, 3 Hz), 105.61 $J_{C-F}$(t, 27 Hz), 46.71 $J_{C-F}$ (d, 8 Hz), 38.50;

FAB-MS m/z=364 [M+H]$^+$

Synthesis of 2-(5-chloro-1H-indol-3-yl)-4-(2,4-difluorophenyl)-4-oxo-butanoic Acid (Compound (3-2))

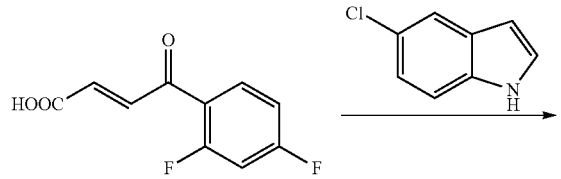

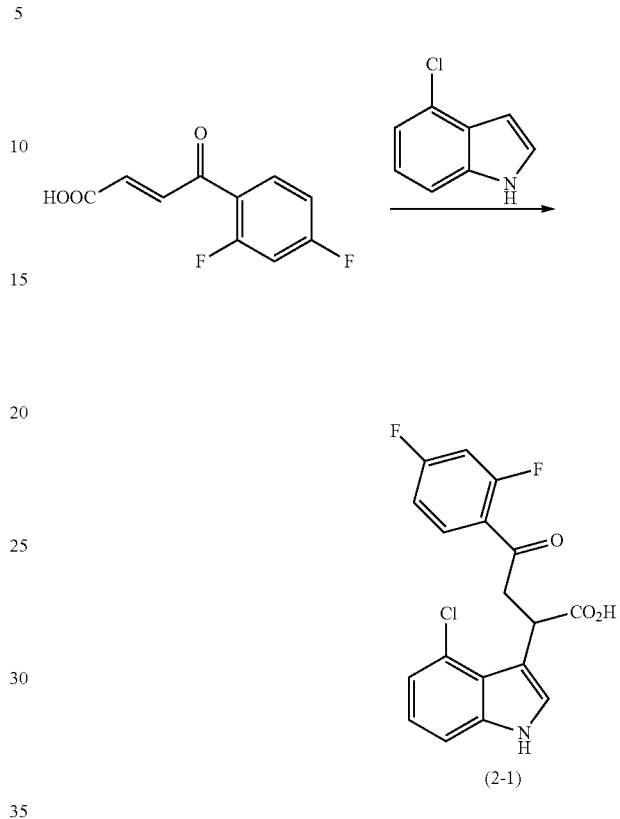

(3-2)

In a 50-mL round-bottomed flask, 5-chloroindole (1000 mg, 6.61 mmol) was added and (E)-4-(2,4-difluorophenyl)-4-oxo-2-butenoic acid (935 mg, 4.41 mmol) was dissolved in benzene (20 mL) and the mixture was heated at 80° C. for 7 hours to reflux. Distilled water (50 mL) was added to the reaction mixture, and extracted twice with ethyl acetate (50 mL). The organic layer was washed twice with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 2-(5-chloro-1H-indol-3-yl)-4-(2,4-difluorophenyl)-4-oxo-butanoic acid (1084 mg, yield: 63%) as a light yellow crystal.

Melting point: 236 to 239° C.;

$^1$H-NMR (400 MHz, acetone-$d_6$) δ 10.45 (s, 1H), 8.02 (q, J=8.3, 1H), 7.80 (d, J=1.6, 1H), 7.44 (m, 2H), 7.11-7.22 (m, 3H), 4.54 (dd, J=10.4, 3.8, 1H), 4.01 (ddd, J=18.7, 10.7, 3.2, 1H), 3.41 (td, J=18.7, 3.2, 1H);

$^{13}$C-NMR (100 MHz, acetone-$d_6$) δ 195.10, 174.76, 166.52 $J_{C-F}$ (dd, 253, 12 Hz), 163.62 $J_{C-F}$ (dd, 253, 12 Hz), 136.06, 133.44 $J_{C-F}$ (dd, 12, 4 Hz), 128.47, 125.62, 122.96 $J_{C-F}$ (dd, 13, 4 Hz), 122.48, 119.33, 113.77, 113.12, 112.96 $J_{C-F}$ (dd, 22, 3 Hz), 105.61 $J_{C-F}$(t, 27 Hz), 46.72 $J_{C-F}$ (d, 8 Hz), 38.35;

FAB-MS m/z=364 [M+H]$^+$

Synthesis of 2-(4-chloro-1H-indol-3-yl)-4-(2,4-difluorophenyl)-4-oxo-butanoic Acid (Compound (2-1))

(2-1)

In a 50-mL round-bottomed flask, 4-chloroindole (903 mg, 5.98 mmol) was added and (E)-4-(2,4-difluorophenyl)-4-oxo-2-butenoic acid (842 mg, 3.97 mmol) was dissolved in benzene (20 mL) and the mixture was heated at 80° C. for 7 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product was purified using silica gel column chromatography (chloroform:methanol=9:1), and the residue was then recrystallized from benzene and acetone to obtain 2-(4-chloro-1H-indol-3-yl)-4-(2,4-difluorophenyl)-4-oxo-butanoic acid (602 mg, yield: 51%) as a colorless crystal.

Melting point: 203 to 204° C.;

$^1$H-NMR (400 MHz, acetone-$d_6$) δ 10.24 (s, 1H), 8.01 (m, 1H), 7.77 (d, J=8.4, 1H), 7.42 (d, J=8.0, 1H), 7.21~7.03 (m, 4H), 4.57 (dd, J=10.8, 3.6, 1H), 4.03 (ddd 18.8, 10.8, 3.2, 1H), 3.38 (td, 18.8, 3.2, 1H); $^{13}$C-NMR (100 MHz, acetone-$d_6$) δ 195.28, 174.97, 166.55 $J_{C-F}$ (dd, 254, 12 Hz), 163.62 $J_{C-F}$ (dd, 254, 12 Hz), 137.646, 137.49, 133.46 $J_{C-F}$ (dd, 11, 4 Hz), 127.37, 123.70, 123.54, 123.05 $J_{C-F}$ (dd, 13, 4 Hz), 122.39, 119.88, 119.79, 112.95 $J_{C-F}$ (dd, 22, 4 Hz), 105.58 $J_{C-F}$ (t, 26 Hz), 46.95 $J_{C-F}$ (d, 8 Hz), 38.47;

FAB-MS m/z=364 [M+H]$^+$

Synthesis of 4-(2,4-difluorophenyl)-2-(5-methyl-1H-indol-3-yl)-4-oxo-butanoic Acid (Compound (3-3))

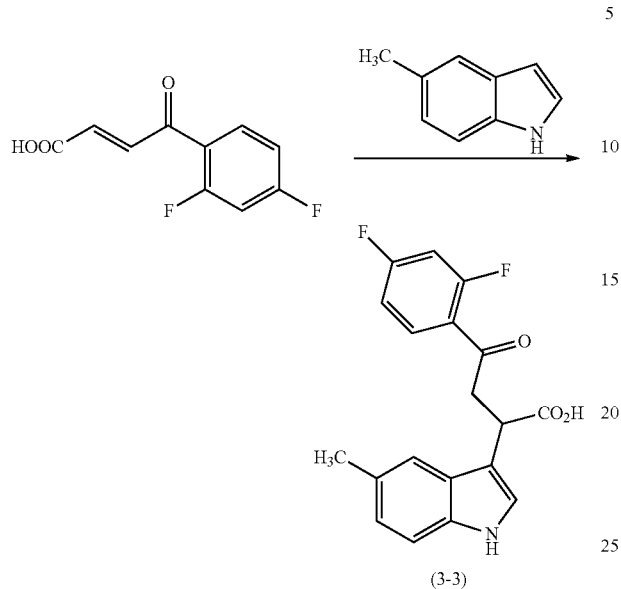

(3-3)

In a 50-mL round-bottomed flask, 5-methylindole (171 mg, 1.31 mmol) was added and (E)-4-(2,4-difluorophenyl)-4-oxo-2-butenoic acid (185 mg, 0.87 mmol) was dissolved in benzene (20 mL) and the mixture was heated at 80° C. for 7 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 4-(2,4-difluorophenyl)-2-(5-methyl-1H-indol-3-yl)-4-oxo-butanoic acid (200 mg, yield: 67%) as a colorless crystal.

Melting point: 200 to 202° C.;

$^1$H-NMR (400 MHz, acetone-$d_6$) δ 10.10 (s, 1H), 8.01 (m, 1H), 7.54 (s, 1H), 7.20-7.31 (m, 2H), 7.13-7.20 (m, 1H), 7.96 (d, J=6.8, 1H), 4.53 (dd, J=10.6, 3.6, 1H), 4.01 (ddd 18.8, 10.6, 3.2, 1H), 3.36 (td, 18.8, 3.2, 1H), 2.40 (s, 3H);

$^{13}$C-NMR (100 MHz, acetone-$d_6$) δ 195.33, 175.08, 166.54 $J_{C-F}$ (dd, 254, 12 Hz), 163.49 $J_{C-F}$ (dd, 254, 12 Hz), 136.01, 133.45 $J_{C-F}$ (dd, 11, 4 Hz), 128.59, 127.63, 124.02, 123.72, 123.05 $J_{C-F}$ (dd, 13, 4 Hz), 119.43, 112.94 $J_{C-F}$ (dd, 22, 4 Hz), 112.74, 112.03, 105.59 $J_{C-F}$(t, 26 Hz), 47.01 $J_{C-F}$(d, 7 Hz), 38.45, 21.64;

FAB-MS m/z=344 [M+H]$^+$

Synthesis of 4-(2,4-difluorophenyl)-2-(1-methyl-1H-indol-3-yl)-4-oxo-butanoic Acid (Compound (6-1))

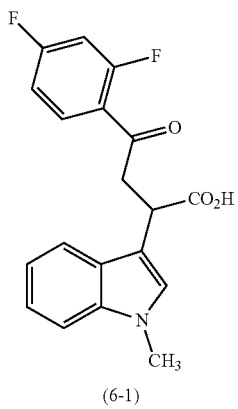

(6-1)

In a 50-mL round-bottomed flask, 1-methylindole (2512 mg, 19.17 mmol) was added and (E)-4-(2,4-difluorophenyl)-4-oxo-2-butenoic acid (2710 mg, 12.78 mmol) was dissolved in benzene (20 mL) and the mixture was heated at 80° C. for 1 hour to reflux. Distilled water (50 mL) was added to the reaction mixture, and extracted twice with ethyl acetate (50 mL). The organic layer was washed twice with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 4-(2,4-difluorophenyl)-2-(1-methyl-1H-indol-3-yl)-4-oxo-butanoic acid (3898 mg, yield: 89%) as a colorless crystal.

Melting point: 192 to 193° C.;

$^1$H-NMR (400 MHz, acetone-$d_6$) δ 8.00 (m, 1H), 7.75 (d, J=7.6, 1H), 7.37 (d, J=8.4, 1H), 7.12-7.22 (m, 4H), 7.07 (t, J=7.6, 1H), 4.54 (dd, J=10.8, 3.6, 1H), 4.00 (ddd, 18.8, 10.4, 3.6, 1H), 3.79 (s, 3H), 3.36 (td, 18.8, 3.6, 1H);

$^{13}$C-NMR (100 MHz, acetone-$d_6$) δ 195.22, 174.94, 166.52 $J_{C-F}$ (dd, 253, 13 Hz), 163.57 $J_{C-F}$ (dd, 253, 13 Hz), 138.08, 133.46 $J_{C-F}$ (dd, 11, 4 Hz), 128.00, 127.79, 123.03 $J_{C-F}$ (dd, 13, 4 Hz), 122.36, 120.07, 119.72, 112.94 $J_{C-F}$(d, 22, 4 Hz), 112.33, 110.32, 105.60 $J_{C-F}$(t, 27 Hz), 47.01 $J_{C-F}$ (d, 8 Hz), 38.36, 32.72;

FAB-MS m/z=344 [M+H]$^+$

Synthesis of 4-(2,4-difluorophenyl)-2-(7-methoxy-1H-indol-3-yl)-4-oxo-butanoic Acid (Compound (5-2))

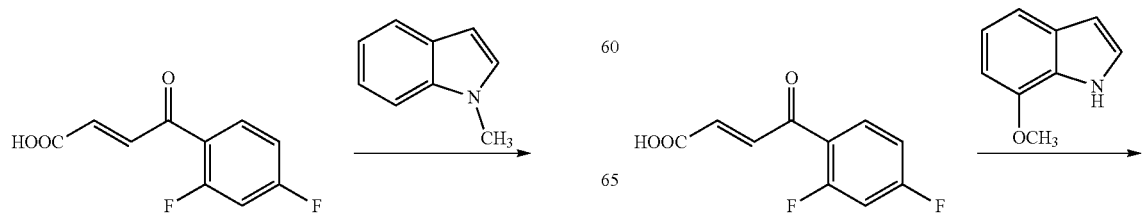

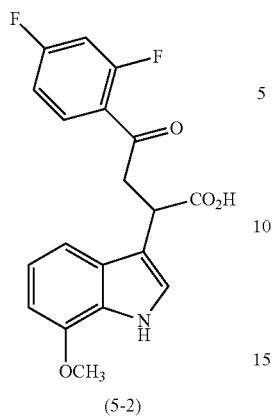

(5-2)

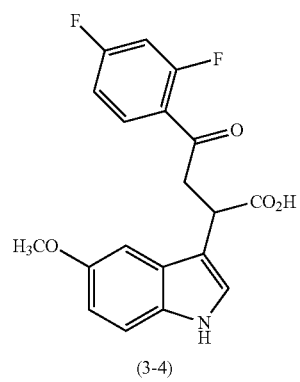

(3-4)

In a 50-mL round-bottomed flask, 7-methoxyindole (1083 mg, 7.36 mmol) was added and (E)-4-(2,4-difluorophenyl)-4-oxo-2-butenoic acid (1041 mg, 4.90 mmol) was dissolved in benzene (20 mL) and the mixture was heated at 80° C. for 14 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 4-(2,4-difluorophenyl)-2-(7-methoxy-1H-indol-3-yl)-4-oxo-butanoic acid (1179 mg, yield: 67%) as a colorless crystal.

Melting point: 181 to 183° C.;

$^1$H-NMR (400 MHz, acetone-$d_6$) δ 10.26 (s, 1H), 8.01 (m, 1H), 7.35 (d, J=8.0, 1H), 7.28 (d, J=2.8, 1H), 7.12-7.20 (m, 2H), 6.98 (t, J=7.8, 1H), 6.67 (d, J=7.8, 1H), 4.54 (dd, J=10.8, 3.6, 1H), 4.03 (ddd 18.8, 10.6, 3.3, 1H), 3.92 (s, 3H), 3.36 (td, 18.6, 3.2, 1H);

$^{13}$C-NMR (100 MHz, acetone-$d_6$) δ 1195.28, 174.98, 166.54 $J_{C-F}$ (dd, 252, 12 Hz), 163.48 $J_{C-F}$ (dd, 252, 12 Hz), 147.35, 133.44 $J_{C-F}$ (dd, 11, 4 Hz), 128.81, 127.83, 123.22, 123.05 $J_{C-F}$ (dd, 13, 4 Hz), 120.43, 113.76, 112.94 $J_{C-F}$ (dd, 22, 4 Hz), 112.7, 105.59 $J_{C-F}$(t, 27 Hz), 102.52, 55.52, 46.97 $J_{C-F}$(d, 8 Hz), 38.59;

FAB-MS m/z=360 [M+H]$^+$

Synthesis of 4-(2,4-difluorophenyl)-2-(5-methoxy-1H-indol-3-yl)-4-oxo-butanoic Acid (Compound (3-4))

In a 50-mL round-bottomed flask, 5-methoxyindole (1166 mg, 7.93 mmol) was added and (E)-4-(2,4-difluorophenyl)-4-oxo-2-butenoic acid was dissolved in benzene (20 mL) and the mixture was heated at 80° C. for 10 hours to reflux. Distilled water (50 mL) was added to the reaction mixture, and extracted twice with ethyl acetate (50 mL). The organic layer was washed twice with saturated saline (30 mL), and dried over anhydrous sodium sulfate, and concentrated under reduced pressure. The product obtained by the concentration was filtrated with a Hirsch funnel, and the residue was recrystallized from benzene and acetone following by recrystallizing from chloroform to obtain 4-(2,4-difluorophenyl)-2-(5-methoxy-1H-indol-3-yl)-4-oxo-butanoic acid (1478 mg, yield: 75%) as a colorless crystal.

Melting point: 205 to 206° C.;

$^1$H-NMR (400 MHz, acetone-$d_6$) δ 10.09 (s, 1H), 8.02 (m, 1H), 7.27-7.31 (m, 3H), 7.13-7.20 (m, 2H), 6.79 (dd, J=8.8, 2.4, 1H), 4.52 (dd, J=10.8, 3.6, 1H), 4.00 (ddd, 18.8, 10.4, 3.4, 1H), 3.80 (s, 3H), 3.38 (td, 18.6, 3.4, 1H;

$^{13}$C-NMR (100 MHz, acetone-$d_6$) δ 195.35, 175.03, 166.53, $J_{C-F}$ (dd, 253, 12 Hz), 163.61 $J_{C-F}$ (dd, 253, 12 Hz), 154.84, 133.45 $J_{C-F}$ (dd, 11, 4 Hz), 132.72, 127.78, 124.22, 123.04 $J_{C-F}$ (dd, 12, 4 Hz), 112.95 $J_{C-F}$ (dd, 22, 4 Hz), 112.96, 112.68, 105.61 $J_{C-F}$ (t, 26 Hz), 101.58, 55.79, 46.9 $J_{C-F}$ (d, 8 Hz), 38.67;

FAB-MS m/z=360 [M+H]$^+$

Synthesis of 2-(6-benzyloxy-1H-indol-3-yl)-4-(2,4-difluorophenyl)-4-oxo-butanoic Acid (Compound (4-2))

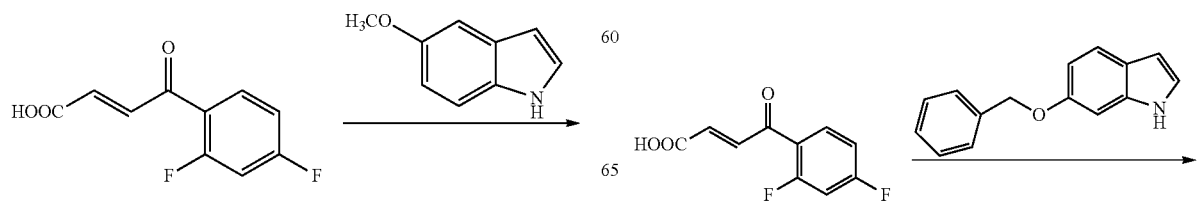

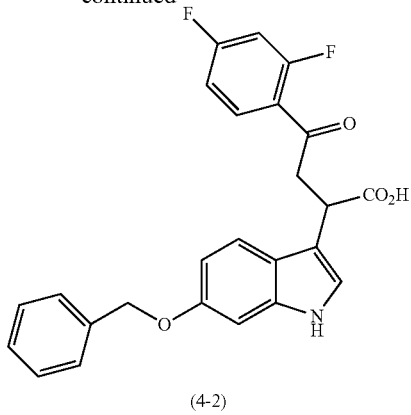

(4-2)

In a 50-mL round-bottomed flask, 6-benzyloxyindole (1255 mg, 5.62 mmol) was added and (E)-4-(2,4-difluorophenyl)-4-oxo-2-butenoic acid (795 mg, 3.74 mmol) was dissolved in benzene (20 mL) and the mixture was heated at 80° C. for 9 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from chloroform to obtain 2-(6-benzyloxy-1H-indol-3-yl)-4-(2,4-difluorophenyl)-4-oxo-butanoic acid (531 mg, yield: 33%) as a light yellow crystal.

Melting point: 177 to 178° C.;

$^1$H-NMR (400 MHz, acetone-$d_6$) δ 10.04 (s, 1H), 8.01 (m, 1H), 7.65 (d, J=8.8, 1H), 7.48 (d, J=7.6, 2H), 7.38 (t, J=7.2, 2H), 7.31 (m, 1H), 7.13-7.20 (m, 3H), 7.03 (d, J=2.0, 1H), 6.83 (dd, J=8.4, 2.0, 1H), 4.51 (dd, J=10.4, 3.6, 1H), 4.01 (ddd, 18.1, 10.4, 3.3, 1H), 3.36 (td, 18.1, 3.3, 1H);

$^{13}$C-NMR (100 MHz, acetone-$d_6$) δ 195.29, 175.00, 166.54 $J_{C-F}$ (dd, 254, 12 Hz), 163.52 $J_{C-F}$ (dd, 254, 12 Hz), 156.33, 138.85, 138.45, 133.45, $J_{C-F}$ (dd, 11, 4 Hz), 129.17, 128.37, 128.23, 123.01 $J_{C-F}$ (dd, 13, 4 Hz), 122.49, 121.97, 120.54, 113.24, 113.06 $J_{C-F}$ (dd, 21, 4 Hz), 110.73, 105.59 $J_{C-F}$(t, 27 Hz), 96.89, 70.70, 46.94 $J_{C-F}$(d, 8 Hz), 38.57;

FAB-MS m/z=436 [M+H]$^+$

Reference Example 1

(E)-4-(2,4-Difluorophenyl)-4-oxo-2-butenoic Acid

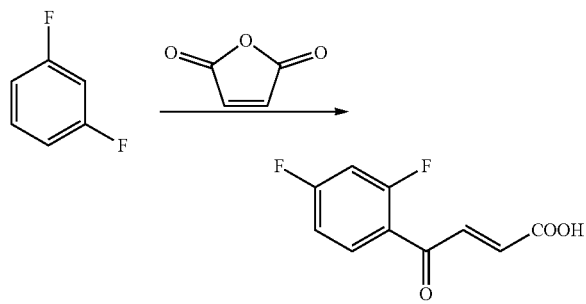

(E)-4-(2,4-Difluorophenyl)-4-oxo-2-butenoic acid which is used for the synthesize of the present compounds #1 to 10 was synthesized as follows. Specifically, in a 100-mL round-bottomed flask, 1,3-difluorobenzene (1300 mg, 11.39 mmol) and maleic anhydride (894 mg, 9.12 mmol) was added and dissolved in dichloromethane (40 mL) and stirred by a stirrer machine. While stirring, to the solution, anhydrous aluminum chloride (2279 mg, 17.09 mmol) were added little by little, and the mixture was stirred at room temperature for 6 hours. The reaction solution in the round-bottomed flask was added into iced water (100 mL) to terminate the reaction. Thereafter, the water layer was extracted with ethyl acetate (150 mL), and the organic layer was extracted with saturated saline (100 mL) for 2 times Thereafter, the organic layer was dried over anhydrous sodium sulfate, and then concentrated under reduced pressure to obtain a solid. The solid was purified by recrystallization from benzene and a little amount of acetone to obtain (E)-4-(2,4-difluorophenyl)-4-oxo-2-butenoic acid as a crystal with light yellow color by yield 48%.

Melting point: 136.0 to 139.0° C.;

$^1$H-NMR (400 MHz, acetone-$d_6$) δ 7.98 (m, 1H), 7.72 (dd, J=15.6, 3.6, 1H), 7.20-7.28 (m, 2H), 6.75 (d, J=15.6, 2H); $^{13}$C-NMR (100 MHz, acetone-$d_6$) δ 187.13, 166.86 $J_{C-F}$ (dd, 254, 12 Hz), 166.35, 163.33 $J_{C-F}$ (dd, 254, 12 Hz), 139.95 $J_{C-F}$(d, 7 Hz), 133.98 $J_{C-F}$ (dd, 66, 59 Hz), 132.91, 123.22 $J_{C-F}$(d, 9 Hz), 113.33 $J_{C-F}$ (dd, 22, 3 Hz), 105.76, $J_{C-F}$ (t, 22 Hz)

In the following Examples 2, 3, and 5, "m.1555A>G mutant" cells were obtained by skin reproductive to a patient having "m.1555A>G mutation" to obtain dermal fibroblasts, then 10% Primary culture was carried out in DMEM (low glucose) culture solution (manufactured by Nacalai Tesque, Inc) containing FBS (Fetal bovine serum) under the condition of 5% $CO_2$/20% $O_2$, at 37° C. and isolated. In the following Examples 4 and 5, the inner ear culture was carried out in DMEM (high glucose) culture medium containing 10% FBS (Fetal bovine serum) under the condition of 5% $CO_2$/20% $O_2$, at 37° C.

Example 2

2. Confirmation that the Compound Group of the Present Invention has an Effect of Suppressing Cell Death and Cytotoxicity of Cells Derived from Hearing Loss Patients by Oxidative Stress Treatment Patients with "m.1555A>G mutation" are known to cause hearing loss (see Usami et al., J Med Genet. 2000 January; 37 (1): 38-40.). Also, it is known that oxidative stress is related to the susceptibility to noise-induced hearing loss (see "Honkura et al., Sci Rep. 2016 Jan. 18; 6: 19329. doi: 10.1038/srep 19329") and by the oxidative stress it is known that cell death and cytotoxicity of auditory system cells are related to senile hearing loss (see the reference "Journal of Otolaryngology of Japan, 112: 414-421, 2009). Therefore, in order to confirm the preventive or improving effect of hearing loss by the compound of the present invention, when the "m.1555A>G mutant" cell subjected to oxidative stress treatment was cultured in the presence of the compound group of the present invention, whether or not the cell survival level and the cytotoxicity level recovered was analyzed.

2-1 Method

[1] 2000 cells of "m.1555A>G mutant" cells were plated per well in a 96-well cell culture plate and cultured for 24 hours.

[2] Glutathione synthesis inhibitor BSO (L-Buthionine sulphoximine) (manufactured by Sigma-Aldrich) was mixed in the culture solution to be 100 μM and cultured for 24 hours (BSO-treated group). As a control, "m.1555A>G mutant" cells were cultured for 24 hours in the absence of BSO (control treatment group).

[3] For the BSO-treated group, the compound #5 synthesized in Example 1 was mixed into the culture solution so as to be at various concentrations (0.3, 1, 3, 10, and 30 μM) and cultured for 48 hours (N=4). As a control, the cells were cultured in the absence of compound #5 (DMSO was added so as to be 0.01%.).

[4] Cell survival level was measured by MTT assay using Cell Counting Kit-8 (manufactured by Dojindo Laboratories). That is, 100 μL of Cell Count Reagent SF was added to each well, incubated for 2 hours, and after 3 seconds of stirring with a microplate reader, the absorbance was measured at 450 nm (reference 750 nm). In addition, the level of cytotoxicity was detected by measuring lactate dehydrogenase (LDH) activity released extracellularly using Cytotoxicity LDH Assay Kit-WST (manufactured by Dojindo Laboratories). That is, 100 μL each of Working Solution prepared in each well was added, incubated for 30 minutes, Stop Solution was added in 50 μL each, and after stirring for 3 seconds with a microplate reader, the absorbance was measured at 490 nm (reference 750 nm).

2-2 Results

First, when "m.1555A>G mutant" cells were cultured in the presence of BSO ("BSO-treated group DMSO" in FIG. 1), compared with when cultured in the absence of BSO ("control group" in FIG. 1), it was confirmed that the cell survival level decreased (see FIG. 1A) and the cytotoxicity level increased (see FIG. 1B). Next, when compound #5 was added under the conditions, the decrease in cell survival level was inhibited at a concentration of at least 1 μM and was significantly suppressed at a concentration of 10 μM (see FIG. 1A). In addition, the increase in the level of cytotoxicity is suppressed in the presence of at least 0.3 μM of compound #5, and furthermore, in the presence of compound #5 of at least 1 μM, it is reduced to a level almost unchanged from that of the control group, a significant difference was observed in the presence of 3 μM of compound #5 (see FIG. 1B).

These results indicate that the compound group of the present invention such as compound #5 has an effect of suppressing cell death and cytotoxicity caused by oxidative stress in hearing-impaired patients, and it is expected to have preventive or improving effects on hearing loss caused by oxidative stress.

Example 3

3. Confirmation that the Compound Group of the Present Invention has an Effect of Suppressing Cell Death of Cells Derived from Hearing Loss Patients by Drug Treatment Patients with "m.1555A>G mutation" are highly susceptible to drugs and are known to easily cause hearing loss (drug-induced hearing loss) (see the reference "Prezant et al., Nat Genet. 1993 July; 4 (3): 289-94."). Therefore, in order to confirm the preventive or improving effect of the compound of the present invention, when "m.1555A>G mutant" cells are cultured in the presence of the compound group of the present invention together with a drug, whether or not the cell survival level is restored was analyzed.

3-1 Method

[1] 2000 cells of "m.1555A>G mutant" cells were plated per well in a 96-well cell culture plate and cultured for 24 hours.

[2] Cisplatin (manufactured by Yakult Corporation) or gentamicin (manufactured by Nacalai Tesque, Inc.) was mixed into the culture solution to be 100 μM and 2000 μM, respectively, and the compound #5 synthesized in Example 1 was mixed with various concentrations (1 and 10 μM), and cultured for 24 hours (cisplatin-treated group and gentamicin-treated group). As a control, "m.1555A>G mutant" cells were cultured in the absence of cisplatin (control group) or cisplatin-treated group in the absence of compound #5 (DMSO was added to 0.01%) for 24 hours.

[3] Cell survival level was measured by MTT assay using Cell Counting Kit-8 (manufactured by Dojindo laboratories). Specifically, 100 μL of Cell Count Reagent SF was added to each well, followed by incubation for 2 hours, and then stirred with a microplate reader for 3 seconds. Then the absorbance with 450 nm (reference 750 nm) was measured.

3-2 Result

Figure 2A:
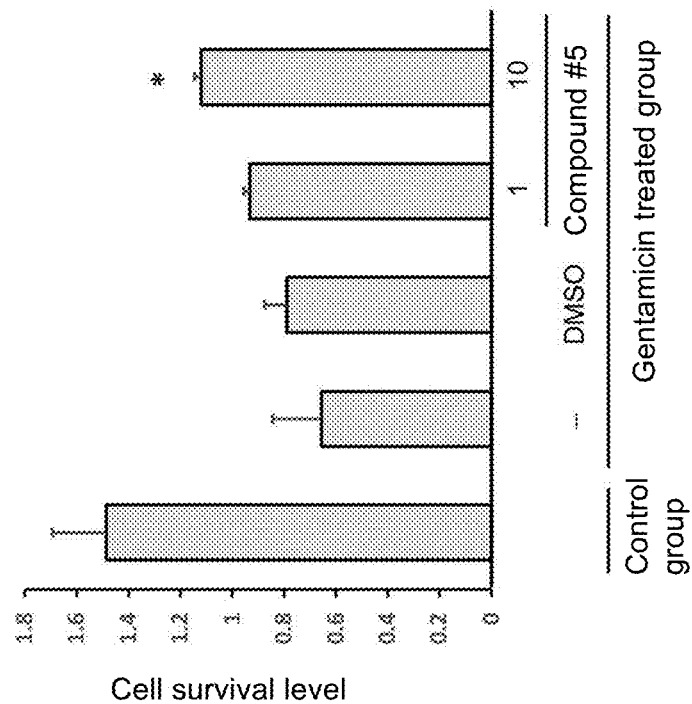
FIG. 2A is a diagram showing the results of analyzing the cell survival level of "m.1555A>G mutant" cells in various cisplatin-treated group and control group.
Figure 2B:
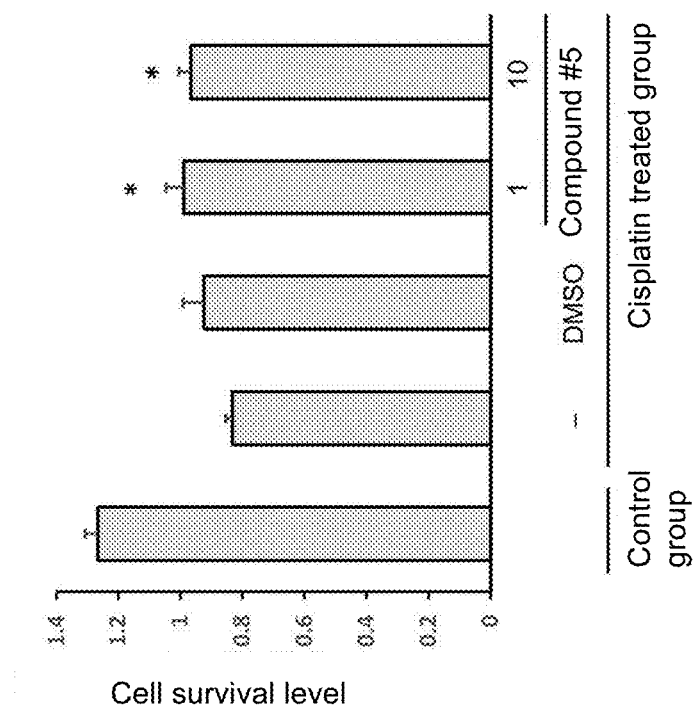
FIG. 2B is a diagram showing the results of analyzing the cell survival level of "m.1555A>G mutant" cells in various gentamicin-treated group and control group.

First, when "m.1555A>G mutant" cells were cultured in the presence of cisplatin or gentamicin ("DMSO of cisplatin-treated group" in FIG. 2A and DMSO of "gentamicin-treated group" of FIG. 2B), cisplatin or gentamicin confirmed that the cell survival level was reduced (see FIGS. 2A and 2B) as compared to cultures in the absence of cisplatin or gentamicin ("control group" in FIGS. 2A and 2B). Next, when compound #5 was added under such conditions, the decrease in cell survival level due to cisplatin treatment was significantly suppressed at a concentration of at least 1 to 10 μM (see FIG. 2A). In addition, the reduction of the cell survival level by gentamicin was also suppressed by at least 1 μM of compound #5 and significantly suppressed by 10 μM of compound #5 (see FIG. 2B).

These results indicate that the compound group of the present invention such as compound #5 has an effect of suppressing cell death caused by drugs of hearing loss patients (e.g., cisplatin, gentamicin), and it is expected to have a preventive or improving effect against drug-induced hearing loss.

Example 4

4. Confirmation that the Compound Group of the Present Invention has an Effect of Suppressing Cell Death of Inner Ear Cell by Drug Treatment In order to confirm that the compound group of the present invention has an effect of suppressing cell death of the inner ear cell by drug treatment, when the inner ear was isolated from the mouse and cultured in the presence of the compound group of the present invention together with the drug, whether the survival level of the inner ear cell recovered or not is analyzed.

4-1 Method

In the experiment, two experiments were carried out, one in the case of changing the concentration of the drug (cisplatin) and the other in the case of changing the concentration of the compound group of the present invention (compound #5).

(When the Drug Concentration is Changed)

[1] The inner ear of C57BL/6J mouse (hereinafter referred to as "P3 mouse") on the third day after birth was isolated and cultured in a culture solution for 24 hours.

[2] Cisplatin was mixed in the culture solution to various concentrations (0, 5, 7.5, 10, 15, and 20 μM), and the compound #5 synthesized in Example 1 was changed to 10 μM mixed in the culture medium and cultured for 48 hours (compound #5-treated group). As a control, the inner ear was cultured for 48 hours in the culture solution (containing 0.01% DMSO) containing the various concentrations of cisplatin and not containing compound #5 (DMSO-treated group).

[3] The cultured sample was fixed in a 4% paraformaldehyde (PFA) solution for 2 hours at room temperature, and in a Tris buffer solution (TBS) containing 0.3% Triton X-100, after immersion for 10 minute, F-actin was stained with rhodamine-labeled phalloidin (1:100, Invitrogen) for 30 minutes at room temperature under light-shielding conditions. Thereafter, washing with TBS (TBST) solution containing 0.3% Triton X-100 for 5 minutes was repeated twice, followed by taking photograph with a fluorescence microscope (BZ-9000, manufactured by Keyence) and observed using BZ-H1 software (manufactured by Keyence). From the obtained image, the number of cells and the number of damaged cells, each of which has a shape of 200 µm each corresponding to each part of the apex turn, the media turn, and the basilar turn, were measured and 3 parts of the cochlea (apex, media, basilar) were calculated from the survival rate (%) of the outer hair cells and the inner hair cells.

(when the Concentration of the Compound Group of the Present Invention is Changed)

[1] The inner ear of P3 mice was isolated and cultured in culture solution for 24 hours.

[2] Cisplatin was mixed in the culture solution to be 10 µM, and the compound #5 synthesized in Example 1 was added to the culture medium (0, 1, 5, 10, and 50 µM) at various concentrations and cultured for 48 hours.

[3] By the method described in [3] above (in the case of changing the drug concentration), histologically the number of outer hair cells and inner hair cells in 3 parts (apex, media, and basilar) of the cell survival rate (%) was calculated.

4-2 Results (When the Drug Concentration is Changed)

Figures 3A, 3B, 3C, 3D, 3E, 3F:
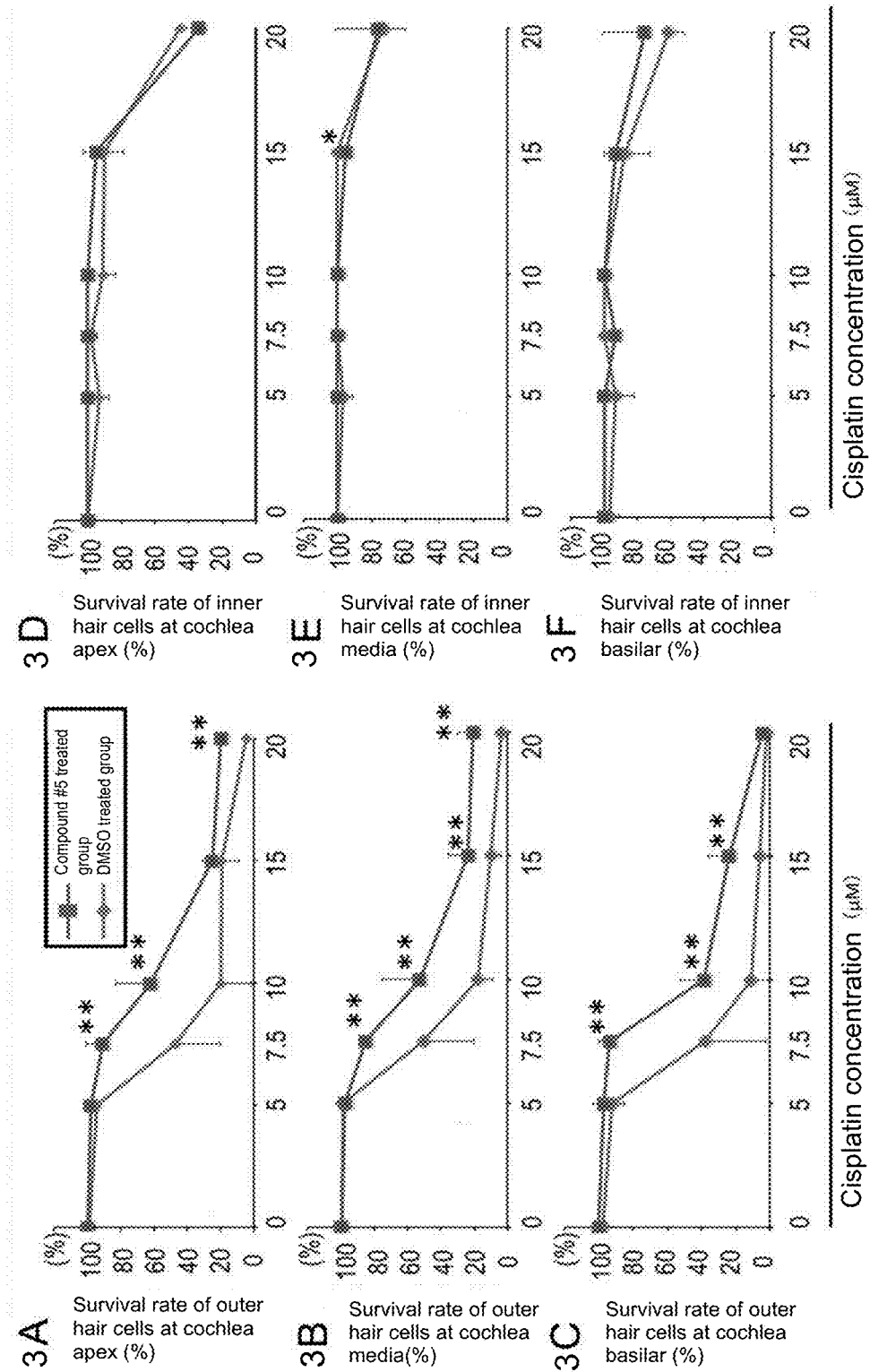
FIGS. 3A-3F are diagrams showing the results of analyzing the survival rates of outer hair cells (FIGS. 3A to C) and inner hair cells (FIGS. 3D to F) at three parts of cochlea (apex, media, and basilar), when an inner ear was cultured in a culture medium containing various concentrations (0, 5, 7.5, 10, 15, and 20 μM) of cisplatin or 10 μM of Compound #5 (Compound #5-treated group) or 0.01% DMSO (DMSO-treated group). "**" in the figure indicates that there is a statistically significant difference ($p<0.01$) between the compound #5-treated group of the same cisplatin concentration and the DMSO-treated groups.

It was confirmed that the survival rate of the outer hair cells in the DMSO-treated group decreased with the concentration of cisplatin in a concentration-dependent manner (see FIGS. 3A to C). On the other hand, it was shown that the survival rate of the outer hair cells in the compound #5-treated group was increased as compared with the DMSO-treated group (see FIGS. 3A to C). This result indicates that the compound group of the present invention such as compound #5 has an effect of suppressing cell death of inner ear cells by drug treatment such as cisplatin. As to the survival rate of the inner hair cells, since there was hardly any decrease in the cell survival rate due to cisplatin in the DMSO-treated group in the first place, there was hardly any difference from the compound #5-treated group (FIGS. 3D to F).

(When the Compound Group Concentration of this Compound Group is Changed)

Figures 4A, 4B, 4C, 4D, 4E, 4F:
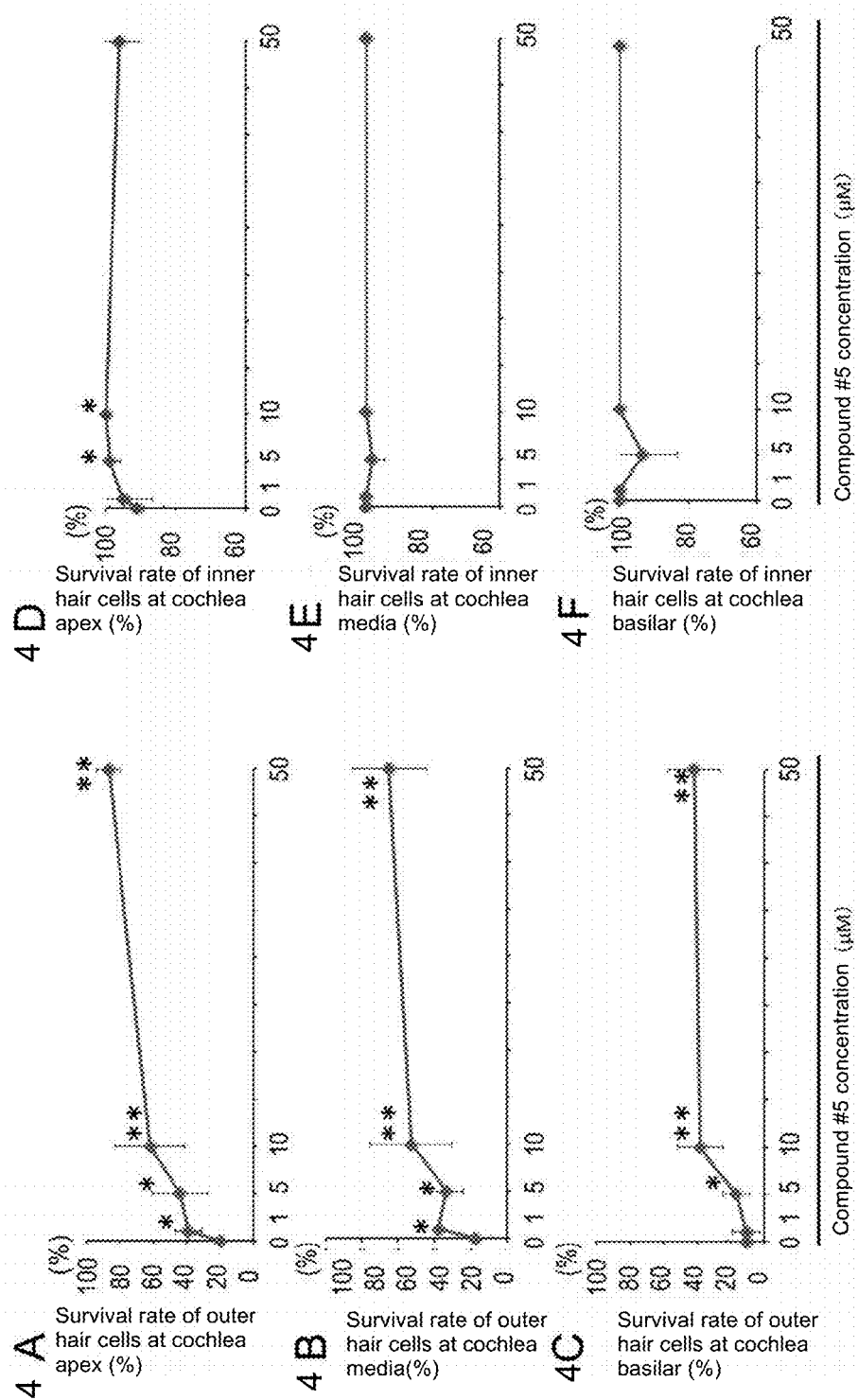
FIGS. 4A-4F are diagrams showing the results of analyzing the survival rates of outer hair cells (FIGS. 4A to C) and inner hair cells (FIGS. 4D to F) at three parts of cochlea (apex, media, and basilar), when an inner ear was cultured in a culture medium containing 10 μM of cisplatin or various concentrations (0, 1, 5, 10, and 50 μM) of Compound #5. "*" or "**" in the figure indicate that there are statistically significant differences ($p<0.05$, and $p<0.01$ each) against the cell survival rates cultured without compound #5 (0 μM of Compound #5).

It was shown that the survival rate of the outer hair cells increases in a concentration-dependent manner of compound #5 (see FIGS. 4A to 4 C). From this result, it is shown that the compound group of the present invention such as compound #5 can suppress the cell death of inner ear cells by drug treatment such as cisplatin in a concentration-dependent manner. Regarding the survival rate of the inner hair cells, since there was hardly any decrease in cell survival rate due to cisplatin in the first place, almost no change in survival rate due to the difference in the concentration of compound #5 was observed (see FIGS. 4D to 4 F).

Example 5

5. Confirmation that the Compound Group of the Present Invention has an Effect of Increasing the Amount of ATP Production in Cells Derived from Hearing Loss Patients and Inner Ear Cells In order to analyze the mechanism of the cell death inhibitory effect of the group of compounds of the present invention by cell derived from hearing loss patients and inner ear cells, "m.1555A>G mutant" cells and inner ear cells were cultured in the presence of compound #5, and the amount of ATP produced was measured.

5-1 Method (About Cells Derived from Hearing Loss Patients)

[1] Three thousand "m.1555A>G mutant" cells were seeded per well in a 96-well cell culture plate and cultured for 24 hours.

[2] Compound #5 synthesized in Example 1 was mixed into the culture solution to be 10 µM and cultured for 12 hours (compound-treated group). As a control, "m.1555A>G mutant" cells were cultured in a culture medium in the absence of compound #5 (control group) or in a culture medium containing 0.01% DMSO (DMSO-treated group) for 12 hours.

[3] The concentration of ATP in the culture solution was measured with "cellular" ATP assay reagent (manufactured by Toyo Binet).

(about Inner Ear Cells)

[1] The inner ear of P3 mice was isolated and cultured in culture solution for 24 hours.

[2] The compound #5 synthesized in Example 1 was mixed in the culture solution to be 10 µM and cultured for various times (3 hours, 6 hours, and 12 hours). Since the inner ear cells do not divide and proliferate, considering that they gradually weaken after the dissection, the time to add compound #5 is adjusted so that the amount of ATP production can be measured at 36 hours after removal.

[3] The concentration of ATP in the culture solution was measured with "cellular" ATP assay reagent (manufactured by Toyo Binet).

5-2 Result

Figures 5A, 5B:
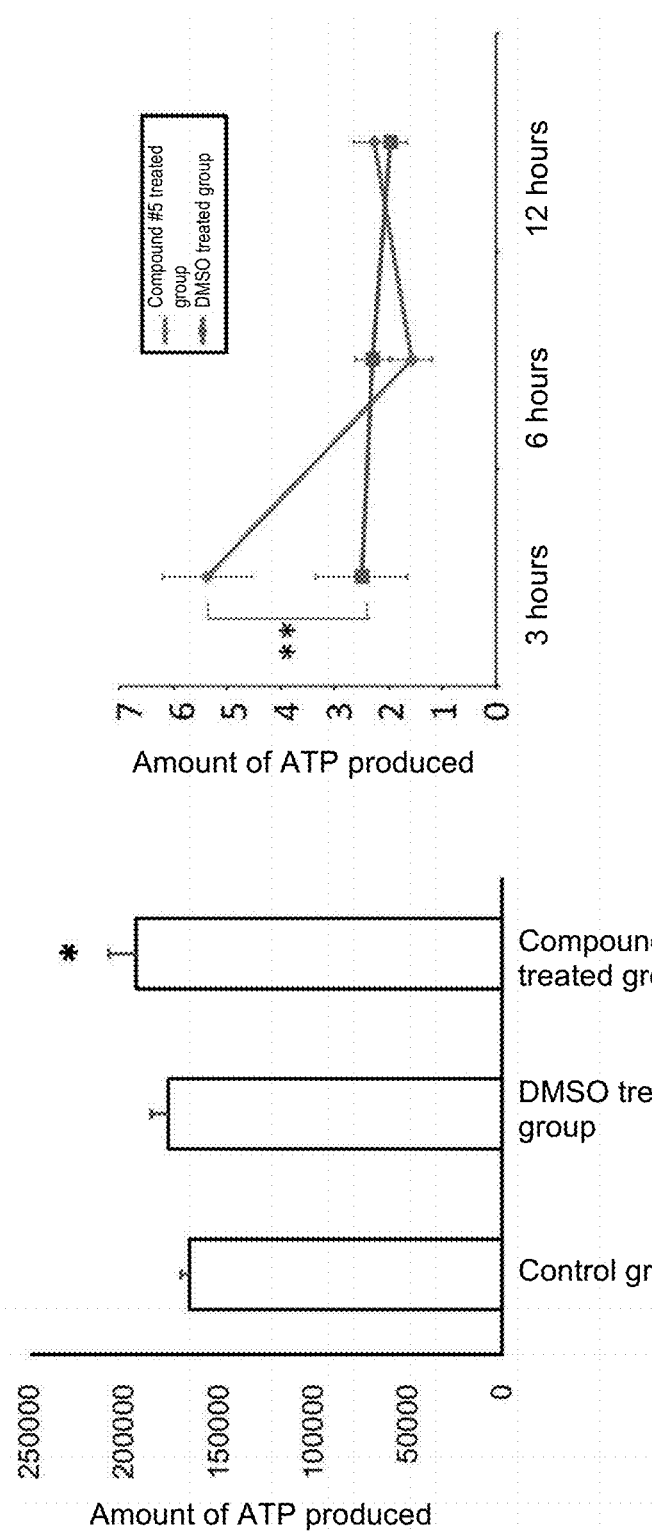
FIG. 5A is a diagram showing the results of measuring the amount of ATP produced in "m.1555A>G mutant" cells in three groups (control group, DMSO-treated group, and compound #5-treated group). "*" in the figure indicates that there is a statistically significant difference ($p<0.05$) against the control group.
FIG. 5B shows that the results of measuring the amount of ATP produced, when an inner ear was cultured in a culture solution containing 10 μM of the compound #5 (compound #5-treated group), or 0.01% of DMSO (DMSO-treated group) for 3 hours, 6 hours, or 12 hours. "**" in the figure indicates that there is a statistically significant difference ($p<0.01$) between the compound #5-treated group and the DMSO-treated group.

It was shown that culturing in the presence of compound #5 increases the amount of ATP production in both "m.1555A>G mutant" cells and inner ear cells (see "3 hour results" in FIGS. 5A and 5B). This result suggests that the compound group of the present invention such as compound #5 increased the amount of ATP production in cells derived from hearing loss patients and inner ear cells, and as a result, cell death of these cells was suppressed by oxidative stress and drug treatment. Also in skin cells derived from hearing loss patients attributable to other inherited diseases (POU4F3 gene mutation, MELAS [m.3243A>G mutation], and Alport syndrome) other than "m.1555A>G mutation", "m.1555A>G mutant" cells was confirmed.

Example 6

6. Confirmation that the Compound Group of the Present Invention has an Effect of Improving Hearing Impairment 1

Figures 6A, 6B:
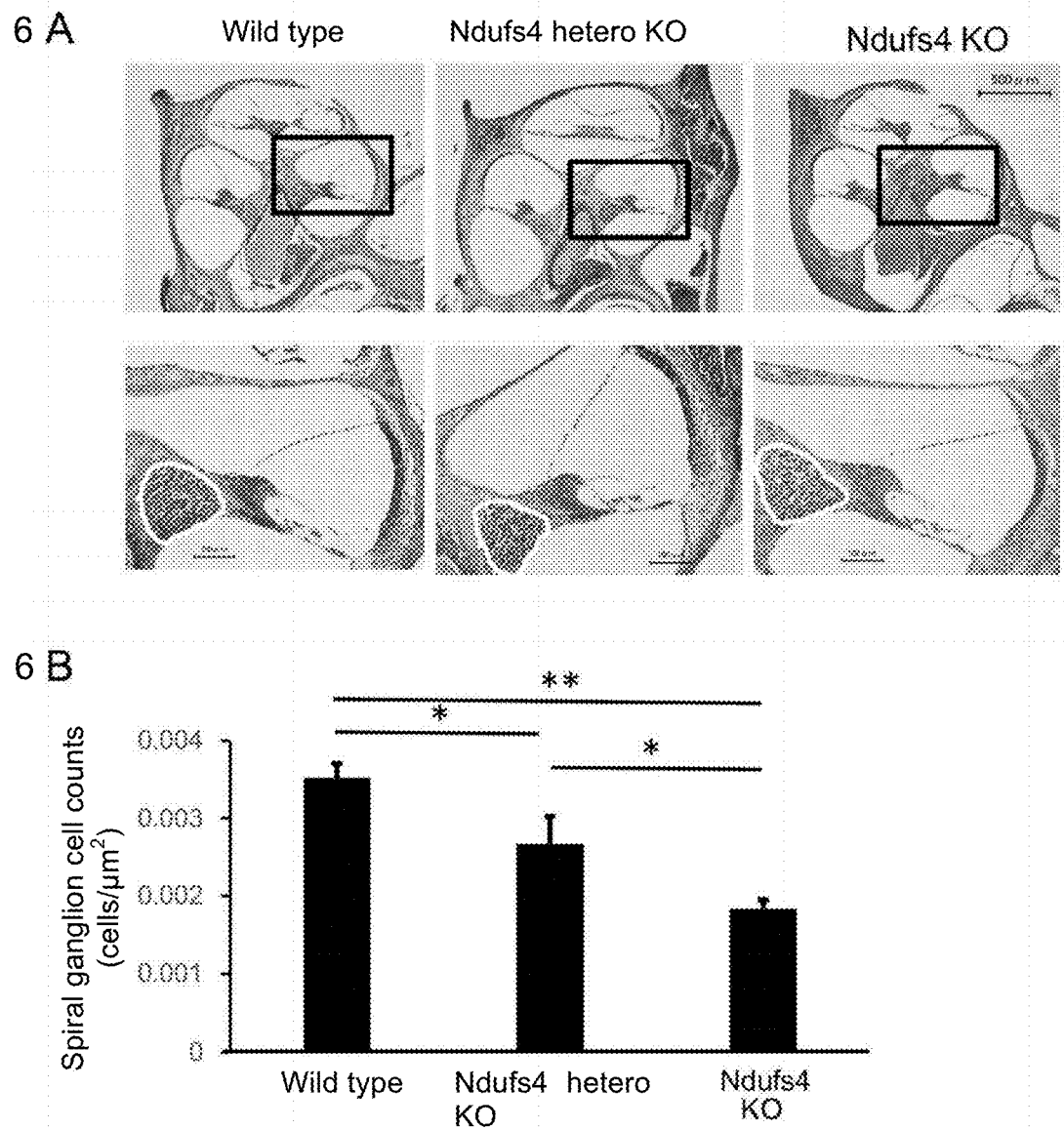
FIGS. 6A-B are diagrams showing the results of analysis of cochlear tissue of 3 types of mice (wild type mouse, Ndufs4 hetero KO mouse, Ndufs4 KO mouse). In the upper part of FIG. 6A, an enlarged image of a region enclosed by a black square is shown in the lower part of each. In the lower part of FIG. 6A, a region surrounded by a white line indicates a Spiral ganglion cell. "Spiral ganglion cell counts" in FIG. 6B is a diagram showing the results of measurement of the cell density (mean value±standard deviation [SE]) in the helical ganglion surrounded by a white line in the image of the lower part of FIG. 6A. "*" and "" in FIG. 6B** indicate statistically significant differences ($p<0.05$ and $p<0.01$), respectively.

From mice knocked out Ndufs 4 (NADH dehydrogenase iron-sulfur protein 4) which is a constituent protein of the respiratory chain complex I present in the inner membrane of mitochondria (Ndufs 4 KO mice), cochlear tissues were isolated at the age of 60 days, and 4% PFA-fixed paraffin-embedded specimens were prepared, followed by staining with hematoxylin and eosin (HE), and the number of helical ganglion cells was counted (n=4). As a result, it was shown that the density of helical ganglion cells responsible for "listening" was significantly smaller than that of wild-type mice and hetero-deficient mice of Ndufs 4 (Ndufs 4 hetero KO mice) (see FIG. 6). This result suggests that Ndufs 4 KO mice may develop hearing loss due to decreased function of the inner ear (especially the cochlea), i.e., inner ear (cochlear) hearing loss. Therefore, in order to confirm the preventive or improving effect of the compound of the present invention, the compound group of the present invention was administered to Ndufs 4 KO mice to analyze whether or not the hearing impairment level recovered.

6-1 Method

Ndufs 4 KO mice (mutant mice due to the substitution of the second exon of the Ndufs 4 gene with Neo sandwiched between loxP sequences) were purchased from Jacson Laboratory. The genetic background of the mouse was C57BL/6, and 60 days old (body weight 10 to 13 g) was used. Compound #5 (1 mg/kg body weight/day) synthesized in Example 1 was orally administered to Ndufs 4 KO mice (administration group of Ndufs 4 KO mice, n=5), between 28 and 60 days of age, at 60 days of age, the hearing ability of the compound #5 administration group was evaluated by auditory brainstem response (ABR). As a control, the hearing ability of Nudfs 4 KO mice not received compound #5 (non-administration group of Ndufs 4 KO mice, n=4), wild type mice not received compound #5 (non-administration group of wild type mice, n=3) and Ndufs 4 hetero KO mice not received compound N #5 (non-administration group of Ndufs 4 hetero KO mice, n=4) was assessed by ABR at 60 days of age. In measuring the hearing ability, a mixture of ketamine (100 mg/kg body weight) and xylazine (20 mg/kg body weight) were anesthetized by intraperitoneal injection of mice. ABR was also analyzed using TDT System 3 workstation and BioSigRP software (Tucker-Davis Technologies). The averaging (1000 times) of the evoked response to the tone burst sound of each frequency (4, 8, 12, 16, and 32 kHz) was recorded. Stimuli sounds were presented at 5 dB intervals from each frequency, 100 dB SPL (Sound Pressure Level) to 10 dB SPL. The threshold value of ABR was set as the minimum sound pressure threshold value at which at least one waveform was confirmed with reproducibility.

6-2 Results

Figure 7:
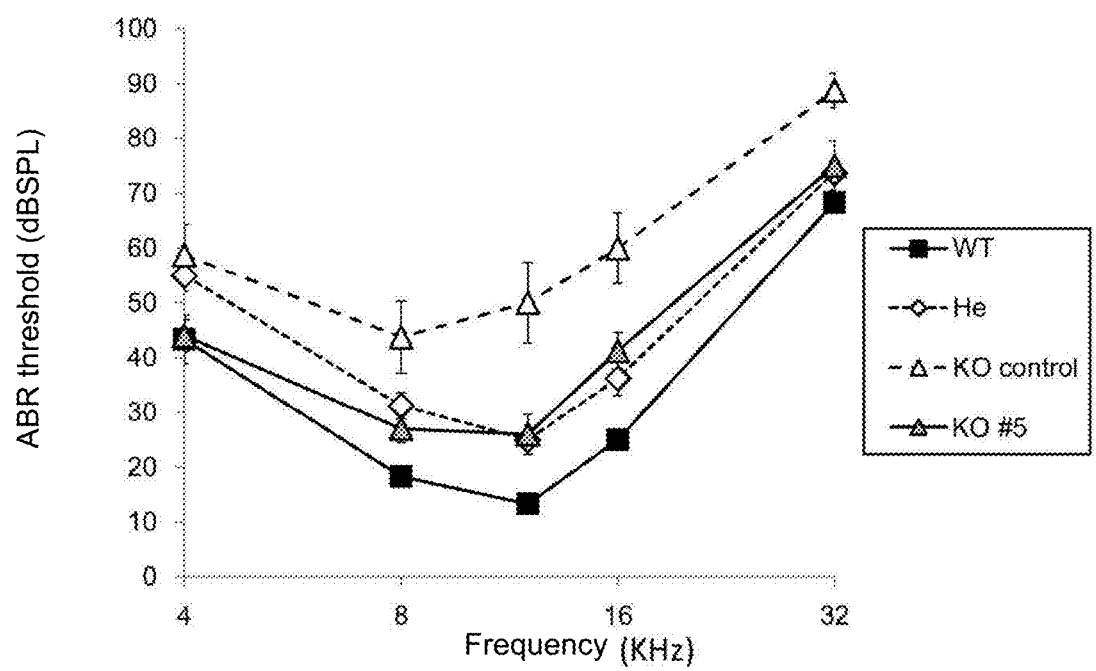
FIG. 7 is a diagram showing the results of evaluations of hearing abilities of four groups (non-administration group of wild type mice ["WT" in the figure], non-administration group of Ndufs4 hetero KO mice ["He" in the figure], non-administration group of Ndufs4 KO mice ["KO control" in the figure] and administration group of Nudfs4 KO mice ["KO #5" in the figure]) based on the auditory brainstem response (ABR; Auditory brainstem responses).

It was shown that the ABR threshold in the non-administration group of Ndufs 4 KO mice increased as compared with the ABR threshold in the non-administration group of wild type mice or the non-administration group of Ndufs 4 hetero KO mice (see FIG. 7). This result indicates that the hearing ability of Ndufs 4 KO mouse is decreasing. On the other hand, it was shown that the ABR threshold in the administration group of Ndufs 4 KO mice was lower than the ABR threshold in the non-administration group of Ndufs 4 KO mice (see FIG. 7). The results indicated that administration of compound #5 to Ndufs 4 KO mice decreased the level of elevation of the ABR threshold (see FIG. 7). This result indicates that hearing loss of Ndufs 4 KO mice is alleviated by administration of compound #5. Because the hearing loss of Ndufs 4 KO mice, a genetic disorder, is caused by a decrease in function of the inner ear and develops with age, the compound group of the present invention is effective against hearing loss caused by genetic diseases, functional deterioration of the inner ear, and age.

Example 7

7. Confirmation that the Compound Group of the Present Invention has an Effect of Improving Hearing Impairment 2

7-1 Method

Using Ndufs 4 KO mice and their littermate wild type mice (littermate wild type mice), the hearing power of littermate wild type mice not received compound #5 (non-administration group of wild-type mice, n=5), Ndufs 4 KO mice not received compound #5 (non-administration group of Ndufs 4 KO mice, n=5) and Ndufs 4 KO mice received compound #5 (administration group of Ndufs 4 KO mice, n=5) were evaluated by ABR at 28 days of age and 60 days of age according to the method described in the item "6-1" of Example 6.

7-2 Results

Figures 8A, 8B, 8C:
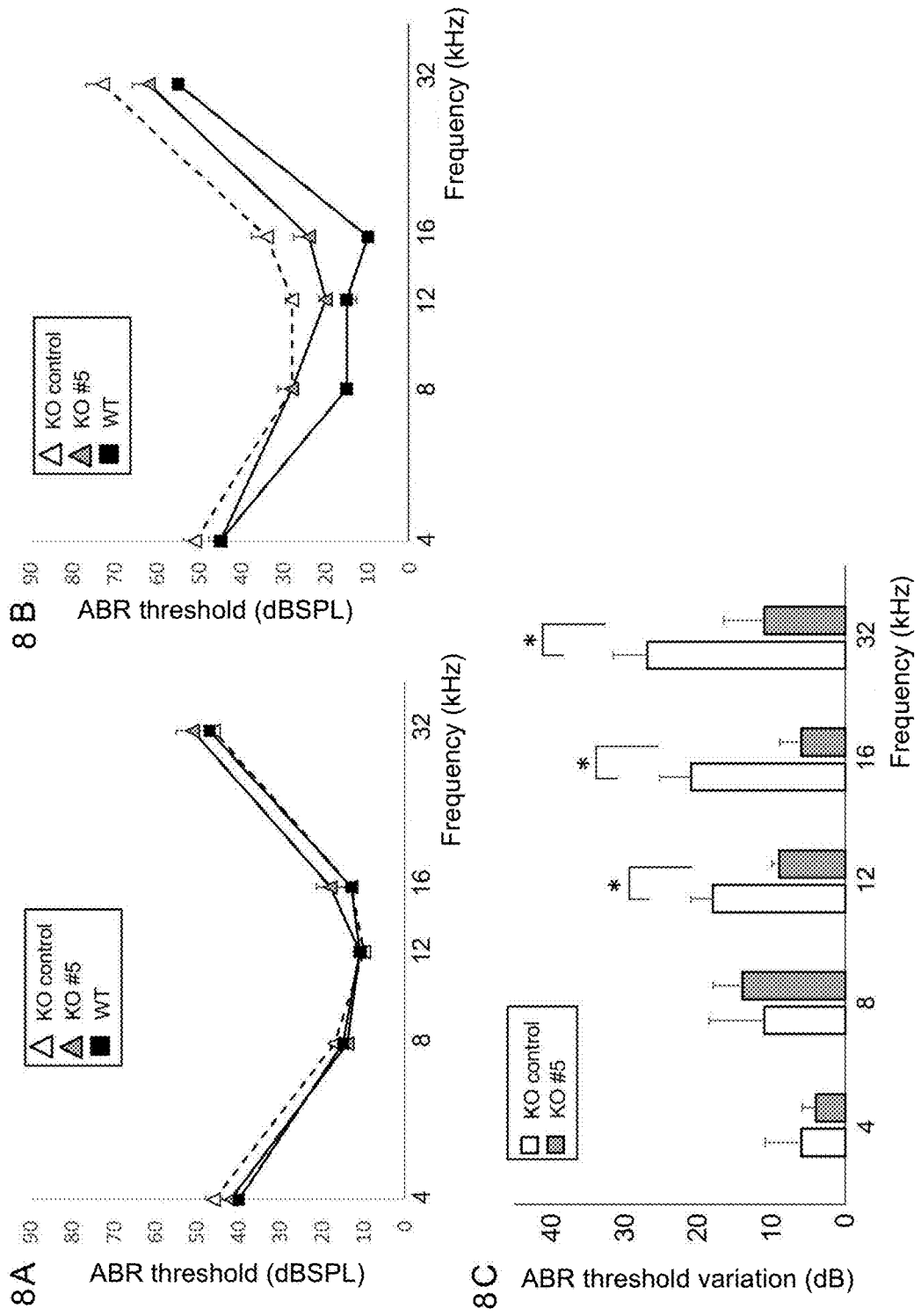
FIGS. 8A-C is a diagram showing the results of evaluations of hearing abilities of three groups (non-administration group of wild type mice ["WT" in the figure], non-administration group of Ndufs4 KO mice ["KO control" in the figure], and administration group of Ndufs4 KO mice ["KO #5" in the figure]) based on ABR.

The ABR threshold of the non-administration group of Ndufs 4 KO mice was shown to be at the same level as the ABR threshold of the non-administration group of wild type mice at 28 days of age (see FIG. 8A). This result indicates that the hearing ability of Ndufs 4 KO mice at a relatively young age is normal.

On the other hand, at the time of 60 days of age, the ABR threshold value of the non-administration group of Ndufs 4 KO mice was elevated as compared with the ABR threshold value of the non-administration group of the wild type mice, whereas the ABR threshold value of the administration group of Ndufs 4 KO mice is decreased, compared with the ABR threshold value of the non-administration group of Ndfs 4 KO mouse (see FIGS. 8B and 8 C). This result showed that the hearing loss of Ndufs 4 KO mice was relieved by administering compound #5 and the results of Example 6 above were reproduced.

Example 8

8. Confirmation that the Compound Group of the Present Invention has an Effect of Improving Hearing Impairment 3

8-1 Method

The dose of compound #5 (1 mg/kg body weight/day) was reduced to 0.3 mg/kg body weight/day. According to the method described in the item "6-1" of Example 6, the hearing power of littermate wild type mice that had not received compound #5 (non-administration group of wild-type mice, n=4), Nudfs 4 KO mice not received compound #5 (non-administration group of Ndufs 4 KO mice, n=4) and Ndufs 4 KO mice received compound #5 (administration group of Ndufs 4 KO mice, n=4) were evaluated by ABR at 28 days of age and 64 days of age.

8-2 Results

Figures 9A, 9B, 9C:
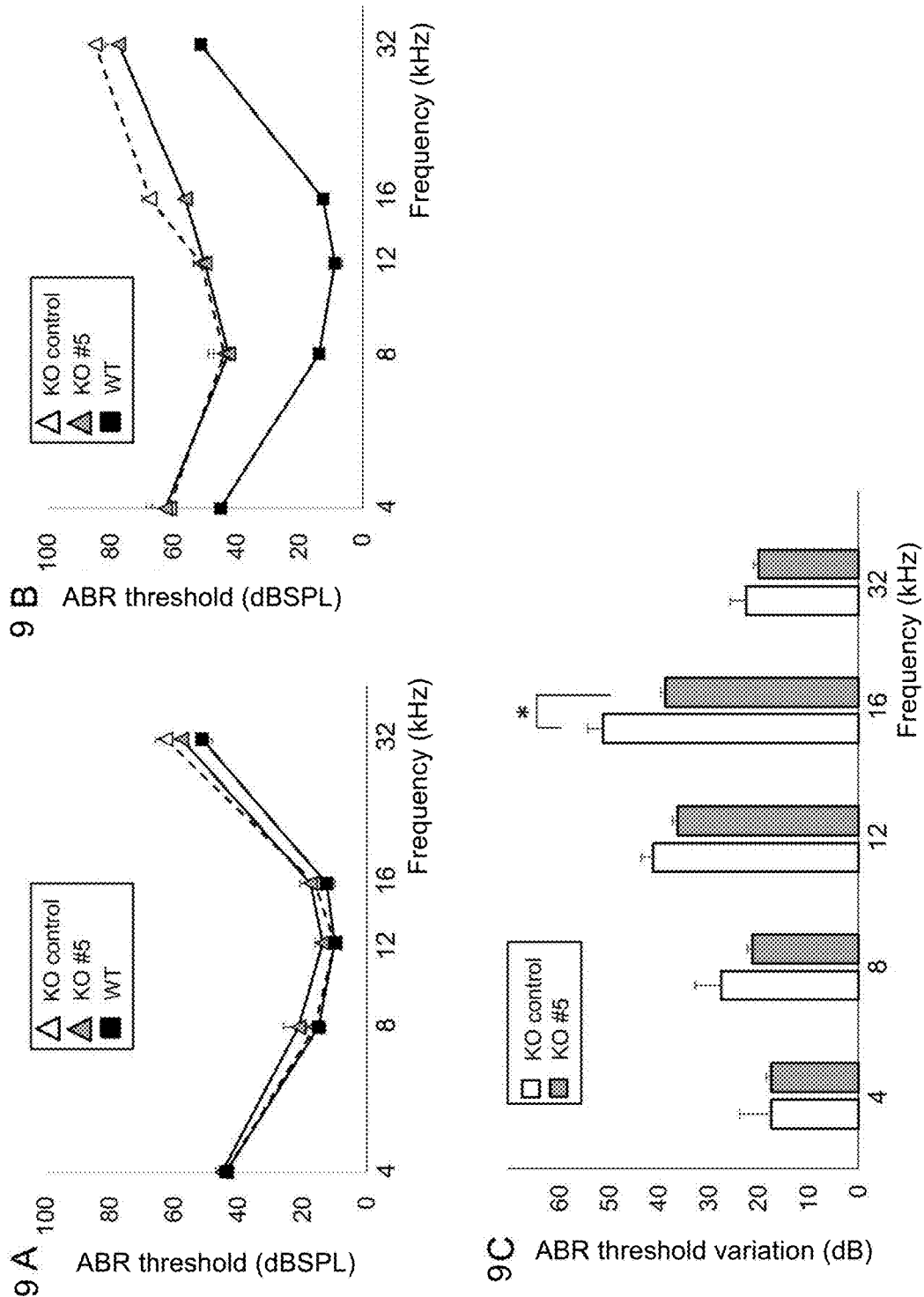
FIGS. 9A-9C are diagrams showing results of evaluations of hearing abilities of three groups (non-administration group of wild type mice ["WT" in the figure], non-administration group of Ndufs4 KO mice ["KO control" in the figure], and administration group of Ndufs4 KO mice ["KO #5" in the figure]) based on ABR.

Similar to the results shown in Example 7, at the 28th day of age at the time point, there was little difference in the ABR threshold between the non-administration group of wild-type mice and the non-administration group of Ndufs 4 KO mice, but at 60 days of age at the time point, the ABR threshold of the non-administration group of Nudfs 4 KO mice compared to the ABR threshold of the non-administration group of wild type mice, whereas the ABR threshold of the administration group of Ndufs 4 KO mice was decreased compared to the ABR threshold of non-administration group of Ndufs 4 KO mice (see FIGS. 9B and 8C). This result indicates that even when the dose of compound #5 (1 mg/kg body weight/day) was reduced to 0.3 mg/kg body weight/day, similarly, compound #5 had the effect of reducing hearing loss.

Example 9

9. Confirmation that the Compound Group of the Present Invention has an Effect of Improving Hearing Loss 4

Next, in order to confirm the effect of preventing or improving hearing loss by the compound of the present invention, the compound group of the present invention was administered to mice exposed to strong sound and inducing short-term hearing impairment to analyze whether or not the hearing impairment level recovered.

9-1 Method

Six male wild-type male mice (C57BL/6) were inoculated into each of three groups (non-administration group of wild type mice, administration (1) group of wild type mice and administration (10) group of wild type mice). Compound #5 (1 mg/kg body weight/day) was orally administered to the administration (1) group of wild type mice for 1 week, compound group #5 (10 mg/kg body weight/day) for 1 week. Compound #5 was not administered to the non-administration group of wild-type mice. After oral administration for 1 week, each group of mice was placed in a chamber for strong acoustic exposure in an awake state, and octave band noise of sound pressure level 100 dB SPL, 8 to 16 kHz was exposed for 2 hours. Noise was generated with a noise generator (SF-06, Random Noise Generator; manufactured by RION), then amplified with an amplifier (D-75A; manufactured by Crown), and the audio was filtered with an audio filter (Multifunction Filter; manufactured by NF Corporation). The frequency band was set and outputted by a speaker (2446H; manufactured by JBL) attached to the center of the ceiling in the chamber. The sound pressure level was measured and confirmed with a sound pressure measuring device (2250L; manufactured by Bruel & Kjar) for each experiment. Hearing power was evaluated by ABR according to the method described in item "6-1" of Example 6 before strong-acoustic exposure and 4 hours after exposure.

9-2 Result

Figures 10A, 10B, 10C:
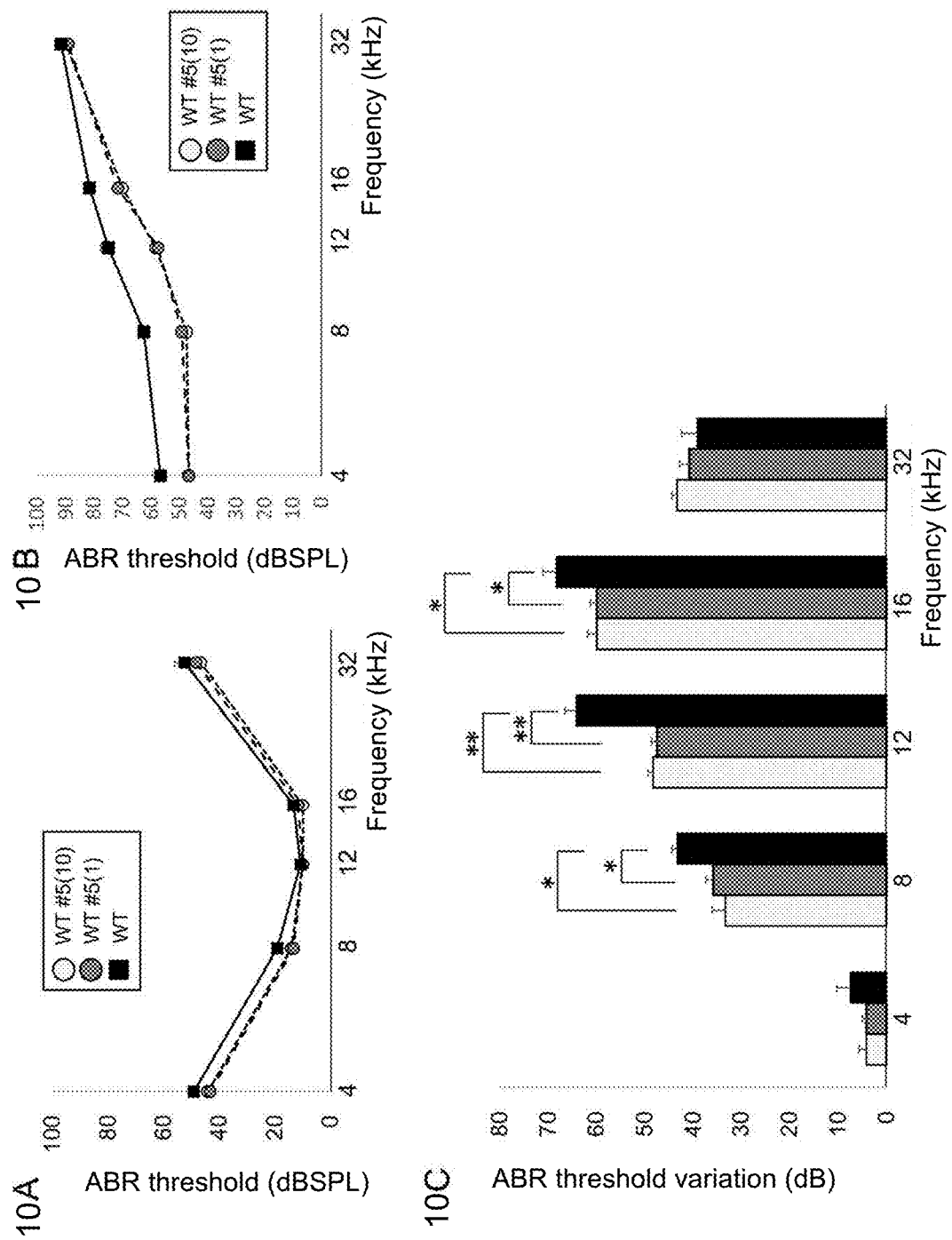
FIGS. 10A-10C are diagrams showing results of evaluations of hearing abilities of three groups (non-administration group of wild type mice ["WT" in the figure], administration (1) group of wild type mice ["WT #5(1)" in the figure], and administration (10) group of wild type mice ["WT #5(10)" in the figure]) based on ABR.

There was no difference between the above three groups of ABR threshold values before strong acoustic exposure (see FIG. 10A). On the other hand, ABR threshold value after 4 hours of strong acoustic exposure was shown to be lower in the administration (1) group of wild type mice and administration (10) group of wild type mice than in the non-administration group of wild type mice (See FIG. 10B). In addition, the ABR threshold change before and after strong acoustic exposure was shown to be decreased in the administration (1) group of wild-type mice and the administration (10) group of wild-type mice compared to the non-administration group of wild-type mice (see FIG. 10C).

These results show that short-term hearing impairment induced by strong acoustic exposure is alleviated by the administration of compound #5. Therefore, the compound group of the present invention is particularly useful for hearing loss caused by noise.

INDUSTRIAL APPLICABILITY

The present invention contributes to prevention or improvement (treatment) of hearing loss.

---

The invention claimed is:
1. A method for treating a hearing loss, comprising the step of administering, to a patient in need thereof, suffering from one or more hearing losses selected from inner ear hearing loss, drug-induced hearing loss, noise-induced hearing loss and age-related hearing loss, a compound represented by the following formula (1-2) or a pharmaceutically acceptable salt thereof: Formula (1-2):

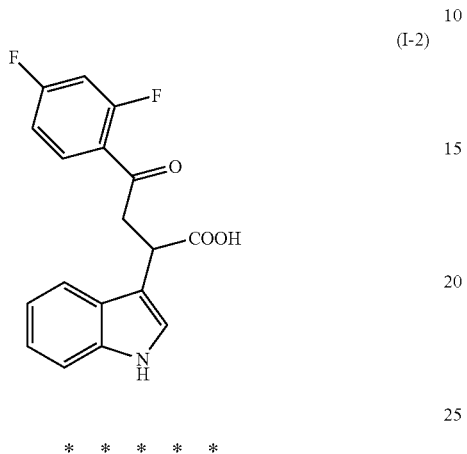

(I-2)

* * * * *

SEQUENCE LISTING

```
<160> NUMBER OF SEQ ID NOS: 1

<210> SEQ ID NO 1
<211> LENGTH: 16569
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3107)..(3107)
<223> OTHER INFORMATION: n is a, c, g or t

<400> SEQUENCE: 1
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
aaccccccct cccccgcttc tggccacagc acttaaacac atctctgcca aaccccaaaa     360
acaaagaacc ctaacaccag cctaaccaga tttcaaattt tatctttttgg cggtatgcac     420 ttttaacagt cacccccaa ctaacacatt atttcccct cccactccca tactactaat     480
ctcatcaata caacccccgc ccatcctacc cagcacacac acaccgctgc taacccata     540 ccccgaacca accaaacccc aaagacaccc cccacagttt atgtagctta cctcctcaaa     600
gcaatacact gaaaatgttt agacgggctc acatcacccc ataaacaaat aggtttggtc     660
ctagcctttc tattagctct tagtaagatt acacatgcaa gcatccccgt tccagtgagt     720
tcaccctcta aatcaccacg atcaaaagga acaagcatca agcacgcagc aatgcagctc     780
```

```
aaaacgctta gcctagccac accccacgg gaaacagcag tgattaacct ttagcaataa    840
acgaaagttt aactaagcta tactaacccc agggttggtc aatttcgtgc cagccaccgc    900
ggtcacacga ttaacccaag tcaatagaag ccggcgtaaa gagtgtttta gatcaccccc    960
tccccaataa agctaaaact cacctgagtt gtaaaaaact ccagttgaca caaaatagac   1020
tacgaaagtg gctttaacat atctgaacac acaatagcta agacccaaac tgggattaga   1080
taccccacta tgcttagccc taaacctcaa cagttaaatc aacaaaactg ctcgccagaa   1140
cactacgagc cacagcttaa aactcaaagg acctggcggt gcttcatatc cctctagagg   1200
agcctgttct gtaatcgata aacccccgatc aacctcacca cctcttgctc agcctatata   1260
ccgccatctt cagcaaaccc tgatgaaggc tacaaagtaa gcgcaagtac ccacgtaaag   1320
acgttaggtc aaggtgtagc ccatgagctg gcaagaaatg ggctacattt tctaccccag   1380
aaaactacga tagcccttat gaaacttaag ggtcgaaggt ggatttagca gtaaactaag   1440
agtagagtgc ttagttgaac agggccctga agcgcgtaca caccgcccgt caccctcctc   1500
aagtatactt caaaggacat ttaactaaaa cccctacgca tttatataga ggagacaagt   1560
cgtaacatgg taagtgtact ggaaagtgca cttggacgaa ccagagtgta gcttaacaca   1620
aagcacccaa cttacactta ggagatttca acttaacttg accgctctga gctaaaccta   1680
gccccaaacc cactccacct tactaccaga caaccttagc caaaccatttt acccaaataa   1740
agtataggcg atagaaattg aaacctggcg caatagatat agtaccgcaa gggaaagatg   1800
aaaaattata accaagcata atatagcaag gactaacccc tataccttct gcataatgaa   1860
ttaactagaa ataactttgc aaggagagcc aaagctaaga cccccgaaac cagacgagct   1920
acctaagaac agctaaaaga gcacacccgt ctatgtagca aaatagtggg aagatttata   1980
ggtagaggcg acaaacctac cgagcctggt gatagctggt tgtccaagat agaatcttag   2040
ttcaacttta aatttgccca cagaaccctc taaatcccct tgtaaattta actgttagtc   2100
caaagaggaa cagctctttg gacactagga aaaaaccttg tagagagagt aaaaaattta   2160
acacccatag taggcctaaa agcagccacc aattaagaaa gcgttcaagc tcaacaccca   2220
ctacctaaaa aatcccaaac atataactga actcctcaca cccaattgga ccaatctatc   2280
accctataga agaactaatg ttagtataag taacatgaaa acattctcct ccgcataagc   2340
ctgcgtcaga ttaaaacact gaactgacaa ttaacagccc aatatctaca atcaaccaac   2400
aagtcattat taccctcact gtcaacccaa cacaggcatg ctcataagga aaggttaaaa   2460
aaagtaaaag gaactcggca aatcttaccc cgcctgttta ccaaaaacat cacctctagc   2520
atcaccagta ttagaggcac cgcctgccca gtgacacatg tttaacggcc gcggtaccct   2580
aaccgtgcaa aggtagcata atcacttgtt ccttaaatag ggacctgtat gaatggctcc   2640
acgagggttc agctgtctct tacttttaac cagtgaaatt gacctgcccg tgaagaggcg   2700
ggcataacac agcaagacga gaagacccta tggagcttta atttattaat gcaaacagta   2760
cctaacaaac ccacaggtcc taaactacca aacctgcatt aaaaatttcg gttggggcga   2820
cctcggagca gaacccaacc tccgagcagt acatgctaag acttcaccag tcaaagcgaa   2880
ctactatact caattgatcc aataacttga ccaacggaac aagttaccct agggataaca   2940
gcgcaatcct attctagagt ccatatcaac aatagggttt acgacctcga tgttggatca   3000
ggacatcccg atggtgcagc cgctattaaa ggttcgtttg ttcaacgatt aaagtcctac   3060
gtgatctgag ttcagaccgg agtaatccag gtcggtttct atctacnttc aaattcctcc   3120
```

```
ctgtacgaaa ggacaagaga aataaggcct acttcacaaa gcgccttccc ccgtaaatga    3180
tatcatctca acttagtatt atacccacac ccacccaaga acagggtttg ttaagatggc    3240
agagcccggt aatcgcataa aacttaaaac tttacagtca gaggttcaat tcctcttctt    3300
aacaacatac ccatggccaa cctcctactc tcattgtac  ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc tcccccatac caacccccct ggtcaacctc    3600
aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aacccccttc    3900
gaccttgccg aaggggagtc cgaactagtc tcaggcttca acatcgaata cgccgcaggc    3960
cccttcgccc tattcttcat agccgaatac acaaacatta ttataataaa cacccctcacc   4020 actacaatct tcctaggaac aacatatgac gcactctccc ctgaactcta cacaacatat    4080
tttgtcacca agaccctact tctaacctcc ctgttcttat gaattcgaac agcatacccc    4140
cgattccgct acgaccaact catacaccctc ctatgaaaaa acttcctacc actcaccctca   4200 gcattactta tatgatatgt ctccataccc attacaatct ccagcattcc ccctcaaacc    4260
taagaaatat gtctgataaa agagttactt tgatagagta aataatagga gcttaaaccc    4320
ccttatttct aggactatga gaatcgaacc catccctgag aatccaaaat tctccgtgcc    4380
acctatcaca ccccatccta aagtaaggtc agctaaataa gctatcgggc ccataccccg    4440
aaaatgttgg ttatacccctt cccgtactaa ttaatcccct ggcccaaccc gtcatctact   4500
ctaccatctt tgcaggcaca ctcatcacag cgctaagctc gcactgattt tttacctgag    4560
taggcctaga aataaacatg ctagctttta ttccagttct aaccaaaaaa ataaaccctc    4620
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagcccccct    4800 ttcacttctg agtcccagag gttacccaag gcacccctct gacatccggc ctgcttcttc    4860
tcacatgaca aaaactagcc cccatctcaa tcatatacca aatctctccc tcactaaacg    4920
taagccttct cctcactctc tcaatcttat ccatcatagc aggcagttga ggtggattaa    4980 accaaacccca gctacgcaaa atcttagcat actcctcaat tacccacata ggatgaataa    5040
tagcagttct accgtacaac cctaacataa ccattcttaa tttaactatt tatattatcc    5100
taactactac cgcattccta ctactcaact taaactccag caccacgacc ctactactat    5160
ctcgcacctg aaacaagcta acatgactaa caccccttaat tccatccacc ctcctctccc    5220
taggaggcct gccccccgcta accggctttt tgcccaaatg ggccattatc gaagaattca    5280
caaaaaacaa tagcctcatc atccccacca tcatagccac catcaccctc cttaacctct    5340
acttctacct acgcctaatc tactccaccct caatcacact actccccata tctaacaacg    5400
taaaaataaa atgacagttt gaacatacaa aacccacccc attcctcccc acactcatcg    5460
cccttaccac gctactccta cctatctccc ctttttatact aataatctta tagaaattta    5520
```

```
ggttaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700
aagcacccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaagaggcc taaccccgt ctttagattt acagtccaat gcttcactca    5880 gccatttac ctcacccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaacccca    6120 tcataatcgg aggctttggc aactgactag ttcccctaat aatcggtgcc cccgatatgg    6180 cgttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccaccct ggagcctccg tagacctaac catcttctcc ttacacctag    6360
caggtgtctc ctctatctta ggggccatca atttcatcac aacaattatc aatataaaac    6420
cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgacccg ccggaggagg agaccccatt ctataccaac    6600
acctattctg attttcggt caccctgaag tttatattct tatcctacca ggcttcggaa    6660
taatctccca tattgtaact tactactccg gaaaaaaga accatttgga tacataggta    6720
tggtctgagc tatgatatca attggcttcc tagggtttat cgtgtgagca caccatatat    6780
ttacagtagg aatagacgta gacacacgag catatttcac ctccgctacc ataatcatcg    6840 ctatcccac cggcgtcaaa gtatttagct gactcgccac actccacgga agcaatatga    6900
aatgatctgc tgcagtgctc tgagccctag gattcatctt tcttttcacc gtaggtggcc    6960
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttccccta ttctcaggct acaccctaga ccaaacctac gccaaaatcc    7140
atttcactat catattcatc ggcgtaaatc taactttctt cccacaacac tttctcggcc    7200
tatccggaat gccccgacgt tactcggact acccccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccacccctacc acacattcga agaacccgta tacataaaat    7440
ctagacaaaa aaggaaggaa tcgaaccccc caaagctggt ttcaagccaa ccccatggcc    7500
tccatgactt tttcaaaaag gtattagaaa aaccatttca taactttgtc aaagttaaat    7560
tataggctaa atcctatata tcttaatggc acatgcagcg caagtaggtc tacaagacgc    7620
tacttcccct atcatagaag agcttatcac ctttcatgat cacgccctca taatcatttt    7680
ccttatctgc ttcctagtcc tgtatgccct tttcctaaca ctcacaacaa aactaactaa    7740
tactaacatc tcagacgctc aggaaataga aaccgtctga actatcctgc ccgccatcat    7800
cctagtcctc atcgccctcc catccctacg catcctttac ataacagacg aggtcaacga    7860
```

```
tccctcccctt accatcaaat caattggcca ccaatggtac tgaacctacg agtacaccga    7920
ctacggcgga ctaatcttca actcctacat acttcccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag gcttaaaaac    8100
agatgcaatt cccggacgtc taaaccaaac cactttcacc gctacacgac cggggggtata    8160
ctacggtcaa tgctctgaaa tctgtggagc aaaccacagt ttcatgccca tcgtcctaga    8220
attaattccc ctaaaaatct ttgaaatagg gcccgtattt accctatagc accccctcta    8280
cccctctag agcccactgt aaagctaact tagcattaac cttttaagtt aaagattaag    8340
agaaccaaca cctctttaca gtgaaatgcc ccaactaaat actaccgtat ggcccaccat    8400
aattacccc atactcctta cactattcct catcacccaa ctaaaaatat aaacacaaa    8460
ctaccaccta cctccctcac caaagcccat aaaaataaaa aattataaca aaccctgaga    8520
accaaaatga cgaaaatct gttcgcttca ttcattgccc ccacaatcct aggcctaccc    8580
gccgcagtac tgatcattct atttcccct ctattgatcc ccacctccaa atatctcatc    8640
aacaaccgac taatcaccac ccaacaatga ctaatcaaac taacctcaaa acaaatgata    8700
accatacaca acactaaagg acgaacctga tctcttatac tagtatccttt aatcattttt    8760
attgccacaa ctaacctcct cggactcctg cctcactcat ttacaccaac cacccaacta    8820
tctataaaacc tagccatggc catccccttta tgagcgggca cagtgattat aggctttcgc    8880
tctaagatta aaaatgccct agcccacttc ttaccacaag gcacacctac acccctatc    8940
cccatactag ttattatcga aaccatcagc ctactcattc aaccaatagc cctggccgta    9000
cgcctaaccg ctaacattac tgcaggccac ctactcatgc acctaattgg aagcgccacc    9060
ctagcaatat caaccattaa ccttccctct acacttatca tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgaccccta acaggggccc tctcagccct cctaatgacc tccggcctag    9300
ccatgtgatt tcacttccac tccataacgc tcctcatact aggcctacta accaacacac    9360
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
ttttcttcgc aggatttttc tgagcctttt accactccag cctagcccct accccccaat    9540
taggagggca ctggccccca acaggcatca ccccgctaaa tccctagaa gtcccactcc    9600
taaacacatc cgtattactc gcatcaggag tatcaatcac ctgagctcac catagtctaa    9660
tagaaaacaa ccgaaaccaa ataattcaag cactgcttat tacaattta ctgggtctct    9720
atttacccct cctacaagcc tcagagtact tcgagtctcc cttcaccatt tccgacggca    9780
tctacggctc aacattttt gtagccacag gcttccacgg acttcacgtc attattggct    9840
caactttcct cactatctgc ttcatccgcc aactaatatt tcactttaca tccaaacatc    9900
actttggctt cgaagccgcc gcctgatact ggcattttgt agatgtggtt tgactatttc    9960
tgtatgtctc catctattga tgagggtctt actcttttag tataaatagt accgttaact   10020
tccaattaac tagttttgac aacattcaaa aaagagtaat aaacttcgcc ttaatttaa   10080
taatcaacac cctcctagcc ttactactaa taattattac attttgacta ccacaactca   10140
acggctacat agaaaaatcc acccttacg agtgcggctt cgaccctata tccccgccc   10200
gcgtcccttt ctccataaaa ttcttcttag tagctattac cttcttatta tttgatctag   10260
```

```
aaattgccct ccttttaccc ctaccatgag ccctacaaac aactaacctg ccactaatag   10320
ttatgtcatc cctcttatta atcatcatcc tagccctaag tctggcctat gagtgactac   10380
aaaaaggatt agactgaacc gaattggtat atagtttaaa caaaacgaat gatttcgact   10440
cattaaatta tgataatcat atttaccaaa tgcccctcat ttacataaat attatactag   10500
catttaccat ctcacttcta ggaatactag tatatcgctc acacctcata tcctccctac   10560
tatgcctaga aggaataata ctatcgctgt tcattatagc tactctcata accctcaaca   10620
cccactccct cttagccaat attgtgccta ttgccatact agtctttgcc gcctgcgaag   10680
cagcggtggg cctagcccta ctagtctcaa tctccaacac atatggccta gactacgtac   10740
ataacctaaa cctactccaa tgctaaaact aatcgtccca acaattatat tactaccact   10800
gacatgactt tccaaaaaac acataaatttg aatcaacaca accacccaca gcctaattat   10860
tagcatcatc cctctactat tttttaacca aatcaacaac aacctattta gctgttcccc   10920
aaccttttcc tccgacccc taacaacccc cctcctaata ctaactacct gactcctacc   10980
cctcacaatc atggcaagcc aacgccactt atccagtgaa ccactatcac gaaaaaaact   11040
ctacctctct atactaatct ccctacaaat ctccttaatt ataacattca cagccacaga   11100
actaatcata ttttatatct tcttcgaaac cacacttatc cccaccttgg ctatcatcac   11160
ccgatgaggc aaccagccag aacgcctgaa cgcaggcaca tacttcctat tctacaccct   11220
agtaggctcc cttcccctac tcatcgcact aatttacact cacaacaccc taggctcact   11280
aaacattcta ctactcactc tcactgccca agaactatca aactcctgag ccaacaactt   11340
aatatgacta gcttacacaa tagcttttat agtaaagata cctctttacg gactccactt   11400
atgactccct aaagcccatg tcgaagcccc catcgctggg tcaatagtac ttgccgcagt   11460
actcttaaaa ctaggcggct atggtataat acgcctcaca ctcattctca accccctgac   11520
aaaacacata gcctacccct tccttgtact atccctatga ggcataatta taacaagctc   11580
catctgccta cgacaaacag acctaaaatc gctcattgca tactcttcaa tcagccacat   11640
agccctcgta gtaacagcca ttctcatcca accccctga agcttcaccg gcgcagtcat   11700
tctcataatc gcccacgggc ttacatcctc attactattc tgcctagcaa actcaaacta   11760
cgaacgcact cacagtcgca tcataatcct ctctcaagga cttcaaactc tactcccact   11820 aatagcttt tgatgacttc tagcaagcct cgctaacctc gccttacccc ccactattaa   11880
cctactggga gaactctctg tgctagtaac cacgttctcc tgatcaaata tcactctcct   11940
acttacagga ctcaacatac tagtcacagc cctatactcc ctctacatat ttaccacaac   12000
acaatggggc tcactcaccc accacattaa caacataaaa ccctcattca cacgagaaaa   12060
caccctcatg ttcatacacc tatcccccat tctcctccta tccctcaacc ccgacatcat   12120
taccgggttt tcctcttgta aatatagttt aaccaaaaca tcagattgtg aatctgacaa   12180
cagaggctta cgaccccta tttaccgaga agctcacaa gaactgctaa ctcatgcccc   12240
catgtctaac aacatggctt tctcaacttt taaaggataa cagctatcca ttggtcttag   12300
gccccaaaaa ttttggtgca actccaaata aaagtaataa ccatgcacac tactataacc   12360
accctaaccc tgacttccct aattccccc atccttacca cctcgttaa ccctaacaaa   12420 aaaactcat accccccatta tgtaaaatcc attgtcgcat ccacctttat tatcagtctc   12480
ttccccacaa caatattcat gtgcctagac caagaagtta ttatctcgaa ctgacactga   12540
gccacaaccc aaacaaccca gctctcccta agcttcaaac tagactactt ctccataata   12600
```

```
ttcatccctg tagcattgtt cgttacatgg tccatcatag aattctcact gtgatatata  12660
aactcagacc caaacattaa tcagttcttc aaatatctac tcatcttcct aattaccata  12720
ctaatcttag ttaccgctaa caacctattc caactgttca tcggctgaga gggcgtagga  12780
attatatcct tcttgctcat cagttgatga tacgcccgag cagatgccaa cacagcagcc  12840
attcaagcaa tcctatacaa ccgtatcggc gatatcggtt tcatcctcgc cttagcatga  12900
tttatcctac actccaactc atgagaccca caacaaatag cccttctaaa cgctaatcca  12960
agcctcaccc cactactagg cctcctccta gcagcagcag gcaaatcagc ccaattaggt  13020
ctccacccct gactccccte agccatagaa ggccccaccc cagtctcagc cctactccac  13080
tcaagcacta tagttgtagc aggaatcttc ttactcatcc gcttccaccc cctagcagaa  13140
aatagcccac taatccaaac tctaacacta tgcttaggcg ctatcaccac tctgttcgca  13200
gcagtctgcg cccttacaca aaatgacatc aaaaaaatcg tagccttctc cacttcaagt  13260
caactaggac tcataatagt tacaatcggc atcaaccaac cacacctagc attcctgcac  13320
atctgtaccc acgccttctt caaagccata ctatttatgt gctccgggtc catcatccac  13380
aaccttaaca atgaacaaga tattcgaaaa ataggaggac tactcaaaac catacctctc  13440
acttcaacct ccctcaccat tggcagccta gcattagcag gaataccttt cctcacaggt  13500
ttctactcca aagaccacat catcgaaacc gcaaacatat catacacaaa cgcctgagcc  13560
ctatctatta ctctcatcgc tacctccctg acaagcgcct atagcactcg aataattctt  13620
ctcaccctaa caggtcaacc tcgcttcccc acccttacta acattaacga aaataacccc  13680
accctactaa accccattaa acgcctggca gccggaagcc tattcgcagg atttctcatt  13740
actaacaaca tttcccccgc atccccttc caaacaacaa tcccctcta cctaaaactc  13800 acagccctcg ctgtcacttt cctaggactt ctaacagccc tagacctcaa ctacctaacc  13860
aacaaactta aaataaaatc cccactatgc acattttatt tctccaacat actcggattc  13920
taccctagca tcacacaccg cacaatcccc tatctaggcc ttcttacgag ccaaaacctg  13980
cccctactcc tcctagacct aacctgacta gaaaagctat tacctaaaac aatttcacag  14040
caccaaatct ccacctccat catcacctca acccaaaaag gcataattaa actttacttc  14100
ctctctttct tcttcccact catcctaacc ctactcctaa tcacataacc tattccccg  14160 agcaatctca attacaatat atacaccaac aaacaatgtt caaccagtaa ctactactaa  14220
tcaacgccca taatcataca aagcccccgc accaatagga tcctcccgaa tcaaccctga  14280 ccctctcct tcataaatta ttcagcttcc tacactatta aagtttacca caaccaccac  14340
cccatcatac tctttcaccc acagcaccaa tcctacctcc atcgctaacc ccactaaaac  14400
actcaccaag acctcaaccc ctgacccca tgcctcagga tactcctcaa tagccatcgc  14460
tgtagtatat ccaaagacaa ccatcattcc ccctaaataa attaaaaaaa ctattaaacc  14520
catataacct cccccaaaat tcagaataat aacacaccg accacaccgc taacaatcaa  14580
tactaaaccc ccataaatag gagaaggctt agaagaaaac cccacaaacc ccattactaa  14640
acccacactc aacagaaaca aagcatacat cattattctc gcacggacta caaccacgac  14700
caatgatatg aaaaaccatc gttgtatttc aactacaaga acaccaatga cccccaatacg  14760 caaaactaac ccctaataa aattaattaa ccactcattc atcgacctcc caccccatc  14820 caacatctcc gcatgatgaa acttcggctc actccttggc gcctgcctga tcctccaaat  14880
caccacagga ctattcctag ccatgcacta ctcaccagac gcctcaaccg ccttttcatc  14940
aatcgcccac atcactcgag acgtaaatta tggctgaatc atccgctacc ttcacgccaa  15000
```

```
tggcgcctca atattcttta tctgcctctt cctacacatc gggcgaggcc tatattacgg    15060
atcatttctc tactcagaaa cctgaaacat cggcattatc ctcctgcttg caactatagc    15120
aacagccttc ataggctatg tcctcccgtg aggccaaata tcattctgag gggccacagt    15180
aattacaaac ttactatccg ccatcccata cattgggaca gacctagttc aatgaatctg    15240
aggaggctac tcagtagaca gtcccaccct cacacgattc tttaccttttc acttcatctt    15300 gcccttcatt attgcagccc tagcaacact ccacctccta ttcttgcacg aaacgggatc    15360
aaacaacccc ctaggaatca cctcccattc cgataaaatc accttccacc cttactacac    15420
aatcaaagac gccctcggct tacttctctt ccttctctcc ttaatgacat taacactatt    15480
ctcaccagac ctcctaggcg acccagacaa ttatacccta gccaacccct taaacacccc    15540
tccccacatc aagcccgaat gatatttcct attcgcctac acaattctcc gatccgtccc    15600
taacaaacta ggaggcgtcc ttgccctatt actatccatc ctcatcctag caataatccc    15660
catcctccat atatccaaac aacaaagcat aatatttcgc ccactaagcc aatcactta    15720 ttgactccta gccgcagacc tcctcattct aacctgaatc ggaggacaac cagtaagcta    15780 ccctttttacc atcattggac aagtagcatc cgtactatac ttcacaacaa tcctaatcct    15840
aataccaact atctccctaa ttgaaaacaa aatactcaaa tgggcctgtc cttgtagtat    15900
aaactaatac accagtcttg taaaccggag atgaaaacct ttttccaagg acaaatcaga    15960
gaaaaagtct ttaactccac cattagcacc caaagctaag attctaatt aaactattct    16020 ctgttctttc atggggaagc agatttgggt accacccaag tattgactca cccatcaaca    16080
accgctatgt atttcgtaca ttactgccag ccaccatgaa tattgtacgg taccataaat    16140
acttgaccac ctgtagtaca taaaaaccca atccacatca aaaccccctc ccatgcttac    16200
caagcaagta cagcaatcaa ccctcaacta tcacacatca actgcaactc caaagccacc    16260
cctcacccac taggatacca acaaacctac ccacccttaa cagtacatag tacataaagc    16320
catttaccgt acatagcaca ttacagtcaa atcccttctc gtcccatgg atgaccccc     16380 tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                            16569
```